United States Patent
Champion et al.

(10) Patent No.: US 11,208,637 B2
(45) Date of Patent: Dec. 28, 2021

(54) VARIANTS OF TERMINAL DEOXYNUCLEOTIDYL TRANSFERASE AND USES THEREOF

(71) Applicants: DNA Script, Paris (FR); Institut Pasteur, Paris (FR)

(72) Inventors: Elise Champion, Paris (FR); Mikhael Soskine, Franconville (FR); Thomas Ybert, Paris (FR); Marc Delarue, Versailles (FR)

(73) Assignees: DNA Script SAS, Le Kremlin-Bicêtre (FR); Institut Pasteur, Paris (FR); National Center for Scientific Research (CNRS), Paris (FR)

( * ) Notice: Subject to any disclaimer, the term of this patent is extended or adjusted under 35 U.S.C. 154(b) by 0 days.

(21) Appl. No.: 16/925,785

(22) Filed: Jul. 10, 2020

(65) Prior Publication Data

US 2021/0009970 A1    Jan. 14, 2021

Related U.S. Application Data

(63) Continuation of application No. 16/423,972, filed on May 28, 2019, now Pat. No. 10,752,887, which is a continuation-in-part of application No. 16/242,904, filed on Jan. 8, 2019, now Pat. No. 10,435,676.

(30) Foreign Application Priority Data

Jan. 8, 2018   (EP) .................................. 18305006

(51) Int. Cl.
   *C12P 21/02*    (2006.01)
   *C12N 9/12*     (2006.01)
   *C12N 15/70*    (2006.01)

(52) U.S. Cl.
   CPC ........... *C12N 9/1264* (2013.01); *C12N 15/70* (2013.01); *C12Y 207/07031* (2013.01)

(58) Field of Classification Search
   CPC ......... C12N 9/1264; C12P 21/02; C12P 19/34
   See application file for complete search history.

(56) References Cited

U.S. PATENT DOCUMENTS

| | | |
|---|---|---|
| 4,448,883 A | 5/1984 | Case |
| 4,772,691 A | 9/1988 | Herman |
| 5,436,143 A | 7/1995 | Hyman |
| 5,516,664 A | 5/1996 | Hyman |
| 5,602,000 A | 2/1997 | Hyman |
| 5,656,745 A | 8/1997 | Bischofberger |
| 5,744,595 A | 4/1998 | Srivastava |
| 5,763,594 A | 6/1998 | Hiatt |
| 5,808,045 A | 9/1998 | Hiatt |
| 5,872,244 A | 2/1999 | Hiatt |
| 5,917,031 A | 6/1999 | Miura |
| 5,935,527 A | 8/1999 | Andrus |
| 5,990,300 A | 11/1999 | Hiatt |
| 6,214,987 B1 | 4/2001 | Hiatt |
| 6,232,465 B1 | 5/2001 | Hiatt |
| 6,623,929 B1 | 9/2003 | Densham |
| 6,777,189 B2 | 8/2004 | Wei |
| 7,057,026 B2 | 1/2006 | Barnes |
| 7,078,499 B2 | 7/2006 | Odedra |
| 7,125,671 B2 | 10/2006 | Sood |
| 7,270,951 B1 | 9/2007 | Stemple |
| 7,407,757 B2 | 8/2008 | Brenner |
| 7,494,797 B2 | 2/2009 | Mueller |
| 7,544,794 B1 | 6/2009 | Benner |
| 7,939,259 B2 | 5/2011 | Kokoris |
| 8,034,923 B1 | 10/2011 | Benner |
| 8,212,020 B2 | 7/2012 | Benner |
| 8,263,335 B2 | 9/2012 | Carr |
| 8,674,086 B2 | 3/2014 | Liu |
| 8,808,988 B2 | 8/2014 | Zhao |
| 8,808,989 B1 | 8/2014 | Efcavitch |
| 9,896,709 B2 | 2/2018 | Makarov |
| 10,059,929 B2 | 8/2018 | Efcavitch |
| 10,435,676 B2 | 10/2019 | Champion et al. |
| 2006/0240439 A1 | 10/2006 | Smith et al. |
| 2014/0363851 A1 | 12/2014 | Efcavitch |
| 2014/0363852 A1 | 12/2014 | Efcavitch |
| 2016/0108382 A1 | 4/2016 | Efcavitch et al. |
| 2018/0016609 A1 | 1/2018 | Chen et al. |
| 2018/0023108 A1 | 1/2018 | Chen |
| 2018/0274001 A1 | 9/2018 | Efcavitch et al. |

(Continued)

FOREIGN PATENT DOCUMENTS

| | | |
|---|---|---|
| WO | WO2016/064880 | 4/2016 |
| WO | WO2016/128731 | 8/2016 |

(Continued)

OTHER PUBLICATIONS

Li et al. (1998) "Crystal structures of open and closed forms of binary and ternary complexes of the large fragment of Thermus aquaticus DNA polymerase I: structural basis for nucleotide incorporation" EMBO J. 17(24): 7514-7525.

Patel et al. (2000) "DNA polymerase active site is highly mutable: Evolutionary consequences" Proc. Natl. Acad. Sci. USA 97(10): 5095-5100.

Schultz et al. (2015) "Taq DNA Polymerase Mutants and 2'-Modified Sugar Recognition" Biochemistry 54: 5999-6008.

(Continued)

*Primary Examiner* — Tekchand Saidha
(74) *Attorney, Agent, or Firm* — Edward J. Baba; Bozicevic, Field & Francis LLP

(57) ABSTRACT

The present invention relates to variants of Terminal deoxynucleotidyl Transferase (TdT), each of which (i) has an amino acid sequence similarity to SEQ ID NO: 2. 11, 13, 15, 17, 19, 21, 23, 25, 27, 29, 31, 33 or 35 with corresponding amino acid substitutions, (ii) is capable of synthesizing a nucleic acid fragment without a template and (iii) is capable of incorporating a modified nucleotide into the nucleic acid fragment.

22 Claims, 2 Drawing Sheets

Specification includes a Sequence Listing.

(56) References Cited

U.S. PATENT DOCUMENTS

2018/0312820 A1 11/2018 Pomerantz et al.
2020/0002690 A1 1/2020 Ybert et al.

FOREIGN PATENT DOCUMENTS

| WO | 2017075421 | 5/2017 |
|----|------------|--------|
| WO | WO2017/216472 | 12/2017 |
| WO | WO2018/215803 | 11/2018 |

OTHER PUBLICATIONS

Uniprot, Accession No. 075417 (2016) www.uniprot.org. 8 pages.
Yousefzadeh et al. (2014) "Mechanism of Suppression of Chromosomal Instability by DNA Polymerase POLQ" PLOS Genetics 10(10): e1004654, 15 pages.
Accession No. A4PCE2, (2007).
Aoufouchi et al. (2000) "Two novel human and mouse DNA polymerases of the polX family," Nucleic Acids Research, 28(18): 3684-3693.
Beabealashvilli et al. (1986) "Nucleoside 5'-triphosphates modified at sugar residues as substrates for calf thymus terminal deoxynucleotidyl transferase and for AMV reverse transcriptase," Biochim. Biophys. Acta., 868(2-3): 136-144.
Bentoila et al. (1995) "The two isoforms of mouse terminal deoxynucleotidyl transferase differ in both the ability to add N regions and subcellular localization," The EMBO Journal, 14(17): 4221-4229.
Boule et al. (1998) "High-level expression of murine terminal deoxynucleotidyl transferase in *Escherichia coli* grown at low temperature and overexpressing argU tRNA," Molecular Biotechnology, 10: 199-208.
Database EPO Proteins, (2016) "Sequence 8 from Patent WO2016128731", XP002779827.
Database UniProt, (2017) SubName: Full=DNA nucleotidylexotransferase isoform X1{EC0:0000313:RefSeq:XP_008057295.1}, XP002779838.
Delarue et al. (2002) "Crystal structures of a template-independent DNA polymerase: murine terminal deoxynucleotidyltransferase," The EMBO Journal, 21(3): 427-439.
Dominguez et al. (2000) "DNA polymerase mu (Pol µ), homologous to TdT, could act as a DNA mutator in eukaryotic cells," The EMBO Journal, 19(17): 1731-1742.
Flickinger et al. (1992) "Differential incorporation of biotinylated nucleotides by terminal deoxynucleotidyl transferase," Nucleic Acids Research, 20(9): 2382.
Gouge et al. (2013) "Structures of intermediates along the catalytic cycle of terminal deoxynucleotidyltransferase: dynamical aspects of the two-metal ion mechanism," J. Mol. Biol., 425: 4334-4352.
International Search Report from PCT International Application No. PCT/FR2017/051519 dated Jan. 18, 2018.
International Search Report from PCT International Application No. PCT/EP2019/050334 dated Feb. 22, 2019.
Koiwai et al. (1986) "Isolation and characterization of bovine and mouse terminal deoxynucleotidyltransferase cDNAS expressible in mammalian cells," Nucleic Acids Research, 14(14): 5777-5792.
Michelson et al. (1982) "Characterization of the homopolymer tailing reaction catalyzed by terminal deoxynucleotidyl transferase," J. Biol. Chem., 257(24): 14773-14782.
Motea et al. (2010) "Terminal deoxynucleotidyl transferase: The story of a misguided DNA polymerase," Biochim Biophys Acta, 1804(5): 1151-1166.
Romain et al. (2009) "Conferring a template-dependent polymerase activity to terminal deoxynucleotidyltransferase by mutations in the Loop1 region," Nucleic Acids Research, 37(14): 4642-4656.
Schmitz et al. (1999) "Solid-phase enzymatic synthesis of oligonucleotides," Organic Lett., 1(11): 1729-1731.
Schott et al. (1984) "Single-step elongation of oligodeoxynucleotides using terminal deoxynucleotidyl transferase," Eur. J. Biochem., 143: 613-620.
Troshchynsky et al. (2015) "Functional analyses of polymorphic variants of human terminal deoxynucleotidyl transferase," Genes and Immunity, 16: 388-398.
UD-DEAN, (2008) "A theoretical model for template-free synthesis of long DNA sequence," Syst. Synth. Biol., 2: 67-73.
Written Opinion from PCT International Application No. PCT/FR2017/051519 dated Jan. 18, 2018.
Yamtich et al. (2010) "DNA polymerase family X: function, structure, and cellular roles," Biochim. Biophys. Acta., 1804(5): 1136-1150.
Yang et al. (1994) "Mutational analysis of residues in the nucleotide binding domain of human terminal deoxynucleotidyl transferase," Journal of Biological Chemistry, 269(16): 11859-11868.
Yang et al. (1995) "T-cell specific avian TdT: characterization of the cDNA and recombinant ezyme," Nucleic Acids Research, 23(11): 2041-2048.
Arana et al. (2008) "Low-fidelity DNA synthesis by human DNA polymerase theta" Nucleic Acids Research 36(11): 3847-3856.
Database Refseq (2016) Predicted: DNA polymerase theta isoform X1 [Rhinolophus sinicus], XP-002776331, 2 pages.
Hogg et al. (2012) "Promiscuous DNA synthesis by human DNA polymerase θ" Nucleic Acids Research 40(6): 2611-2622.
International Search Report from PCT International Application No. PCT/EP2018/071217 dated Feb. 14, 2019.
PIR Accession No. WXHU, published Dec. 4, 1986 (Year: 1986).
PIR Accession No. A23595, published Sep. 10, 1999 (Year: 1999).
PIR Accession No. S55786, published Oct. 27, 1995 (Year: 1995).
PIR Accession No. 151658, published Sep. 13, 1996 (Year: 1996).
Shima et al. (2003) "Phenotype-Based Identification of Mouse Chromosome Instability Mutants" Genetics 163: 1031-1040.
Singapore Patent Office, Written Opinion in Singapore Patent Application No. 11201809961T (dated Apr. 24, 2020).
Written Opinion from PCT International Application No. PCT/EP2018/071217 dated Feb. 14, 2019.
Zahn et al. (2015) "Human DNA polymerase θgrasps the primer terminus to mediate DNA repair" Nat Struc Mol Biol 22(4): 304-3011.

SEQUENCE LISTING

```
<160> NUMBER OF SEQ ID NOS: 9

<210> SEQ ID NO 1
<211> LENGTH: 510
<212> TYPE: PRT
<213> ORGANISM: artificial sequence
<220> FEATURE:
<223> OTHER INFORMATION: murine TdT

<400> SEQUENCE: 1

Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140
```

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
            165                 170                 175

Glu Asn Asp Glu Leu Arg Glu Asn Glu Gly Ser Cys Leu Ala Phe Met
        180                 185                 190

Arg Ala Ser Ser Val Leu Lys Ser Leu Pro Phe Pro Ile Thr Ser Met
    195                 200                 205

Lys Asp Thr Glu Gly Ile Pro Cys Leu Gly Asp Lys Val Lys Ser Ile
210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
            245                 250                 255

Gly Val Gly Leu Lys Thr Ala Glu Lys Trp Phe Arg Met Gly Phe Arg
        260                 265                 270

Thr Leu Ser Lys Ile Gln Ser Asp Lys Ser Leu Arg Phe Thr Gln Met
    275                 280                 285

Gln Lys Ala Gly Phe Leu Tyr Tyr Glu Asp Leu Val Ser Cys Val Asn
290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
            325                 330                 335

Gly Lys Met Thr Gly His Asp Val Asp Phe Leu Ile Thr Ser Pro Glu
        340                 345                 350

Ala Thr Glu Asp Glu Glu Gln Gln Leu Leu His Lys Val Thr Asp Phe
    355                 360                 365

Trp Lys Gln Gln Gly Leu Leu Leu Tyr Cys Asp Ile Leu Glu Ser Thr
370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
            405                 410                 415

Ser Glu Lys Ser Gly Gln Gln Glu Gly Lys Gly Trp Lys Ala Ile Arg
        420                 425                 430

Val Asp Leu Val Met Cys Pro Tyr Asp Arg Arg Ala Phe Ala Leu Leu
    435                 440                 445

Gly Trp Thr Gly Ser Arg Gln Phe Glu Arg Asp Leu Arg Arg Tyr Ala
450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Glu Ile Phe Ala
            485                 490                 495

His Leu Gly Leu Asp Tyr Ile Glu Pro Trp Glu Arg Asn Ala
        500                 505                 510

<210> SEQ ID NO 2
<211> LENGTH: 381
<212> TYPE: PRT
<213> ORGANISM: artificial sequence
<220> FEATURE:
<223> OTHER INFORMATION: murine TdT catalytic domain (CTdT)

<400> SEQUENCE: 2

Asn Ser Ser Pro Ser Pro Val Gly Ser Gln Asn Val Pro Ala Pro
1               5                   10                  15

Ala Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
            35                  40                  45

Asn Asp Glu Leu Arg Glu Asn Glu Gly Ser Cys Leu Ala Phe Met Arg
50                      55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
                85                  90                  95

Glu Gly Ile Ile Glu Asp Gly Glu Ser Ser Glu Ala Lys Ala Val Leu
                100                 105                 110

Asn Asp Glu Arg Tyr Lys Ser Phe Lys Leu Phe Thr Ser Val Phe Gly
            115                 120                 125

Val Gly Leu Lys Thr Ala Glu Lys Trp Phe Arg Met Gly Phe Arg Thr
130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Cys Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Arg Gly
            195                 200                 205

Lys Met Thr Gly His Asp Val Asp Phe Leu Ile Thr Ser Pro Glu Ala
210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
            260                 265                 270

Gln Lys Cys Phe Leu Ile Leu Lys Leu Asp His Gly Arg Val His Ser
            275                 280                 285

Glu Lys Ser Gly Gln Gln Glu Gly Lys Gly Trp Lys Ala Ile Arg Val
290                 295                 300

Asp Leu Val Met Cys Pro Tyr Asp Arg Arg Ala Phe Ala Leu Leu Gly
305                 310                 315                 320

Trp Thr Gly Ser Arg Gln Phe Glu Arg Asp Leu Arg Arg Tyr Ala Thr
            325                 330                 335

His Glu Arg Lys Met Met Leu Asp Asn His Ala Leu Tyr Asp Arg Thr
            340                 345                 350

Lys Arg Val Phe Leu Glu Ala Glu Ser Glu Glu Glu Ile Phe Ala His
            355                 360                 365

Leu Gly Leu Asp Tyr Ile Glu Pro Trp Glu Arg Asn Ala
370                 375                 380

<210> SEQ ID NO 3
<211> LENGTH: 494
<212> TYPE: PRT
<213> ORGANISM: artificial sequence
<220> FEATURE:

<223> OTHER INFORMATION: Human Pol(mu)

<400> SEQUENCE: 3

```
Met Leu Pro Lys Arg Arg Ala Arg Val Gly Ser Pro Ser Gly Asp
1               5                   10                  15

Ala Ala Ser Ser Thr Pro Pro Ser Thr Arg Phe Pro Gly Val Ala Ile
            20                  25                  30

Tyr Leu Val Glu Pro Arg Met Gly Arg Ser Arg Arg Ala Phe Leu Thr
                35                  40                  45

Gly Leu Ala Arg Ser Lys Gly Phe Arg Val Leu Asp Ala Cys Ser Ser
    50                  55                  60

Glu Ala Thr His Val Val Met Glu Glu Thr Ser Ala Glu Glu Ala Val
65                  70                  75                  80

Ser Trp Gln Glu Arg Arg Met Ala Ala Pro Pro Gly Cys Thr Pro
                85                  90                  95

Pro Ala Leu Leu Asp Ile Ser Trp Leu Thr Glu Ser Leu Gly Ala Gly
            100                 105                 110

Gln Pro Val Pro Val Glu Cys Arg His Arg Leu Glu Val Ala Gly Pro
            115                 120                 125

Arg Lys Gly Pro Leu Ser Pro Ala Trp Met Pro Ala Tyr Ala Cys Gln
130                 135                 140

Arg Pro Thr Pro Leu Thr His His Asn Thr Gly Leu Ser Glu Ala Leu
145                 150                 155                 160

Glu Ile Leu Ala Glu Ala Ala Gly Phe Glu Gly Ser Glu Gly Arg Leu
                165                 170                 175

Leu Thr Phe Cys Arg Ala Ala Ser Val Leu Lys Ala Leu Pro Ser Pro
            180                 185                 190

Val Thr Thr Leu Ser Gln Leu Gln Gly Leu Pro His Phe Gly Glu His
            195                 200                 205

Ser Ser Arg Val Val Gln Glu Leu Leu Glu His Gly Val Cys Glu Glu
210                 215                 220

Val Glu Arg Val Arg Arg Ser Glu Arg Tyr Gln Thr Met Lys Leu Phe
225                 230                 235                 240

Thr Gln Ile Phe Gly Val Gly Val Lys Thr Ala Asp Arg Trp Tyr Arg
                245                 250                 255

Glu Gly Leu Arg Thr Leu Asp Asp Leu Arg Glu Gln Pro Gln Lys Leu
            260                 265                 270

Thr Gln Gln Gln Lys Ala Gly Leu Gln His His Gln Asp Leu Ser Thr
            275                 280                 285

Pro Val Leu Arg Ser Asp Val Asp Ala Leu Gln Gln Val Val Glu Glu
            290                 295                 300

Ala Val Gly Gln Ala Leu Pro Gly Ala Thr Val Thr Leu Thr Gly Gly
305                 310                 315                 320

Phe Arg Arg Gly Lys Leu Gln Gly His Asp Val Asp Phe Leu Ile Thr
                325                 330                 335

His Pro Lys Glu Gly Gln Glu Ala Gly Leu Leu Pro Arg Val Met Cys
            340                 345                 350

Arg Leu Gln Asp Gln Gly Leu Ile Leu Tyr His Gln His Gln His Ser
            355                 360                 365

Cys Cys Glu Ser Pro Thr Arg Leu Ala Gln Gln Ser His Met Asp Ala
370                 375                 380

Phe Glu Arg Ser Phe Cys Ile Phe Arg Leu Pro Gln Pro Gly Ala
385                 390                 395                 400
```

-continued

```
Ala Val Gly Gly Ser Thr Arg Pro Cys Pro Ser Trp Lys Ala Val Arg
                405                 410                 415

Val Asp Leu Val Val Ala Pro Val Ser Gln Phe Pro Phe Ala Leu Leu
            420                 425                 430

Gly Trp Thr Gly Ser Lys Leu Phe Gln Arg Glu Leu Arg Arg Phe Ser
        435                 440                 445

Arg Lys Glu Lys Gly Leu Trp Leu Asn Ser His Gly Leu Phe Asp Pro
450                 455                 460

Glu Gln Lys Thr Phe Phe Gln Ala Ala Ser Glu Glu Asp Ile Phe Arg
465                 470                 475                 480

His Leu Gly Leu Glu Tyr Leu Pro Pro Glu Gln Arg Asn Ala
                485                 490
```

<210> SEQ ID NO 4
<211> LENGTH: 401
<212> TYPE: PRT
<213> ORGANISM: artificial sequence
<220> FEATURE:
<223> OTHER INFORMATION: Tag TdT

<400> SEQUENCE: 4

```
Thr Met Gly Ser Ser His His His His His Ser Ser Gly Leu Val
1               5                   10                  15

Pro Arg Gly Ser His Met Ser Pro Ser Pro Val Pro Gly Ser Gln Asn
            20                  25                  30

Val Pro Ala Pro Ala Val Lys Lys Ile Ser Gln Tyr Ala Cys Gln Arg
        35                  40                  45

Arg Thr Thr Leu Asn Asn Tyr Asn Gln Leu Phe Thr Asp Ala Leu Asp
    50                  55                  60

Ile Leu Ala Glu Asn Asp Glu Leu Arg Glu Asn Glu Gly Ser Cys Leu
65                  70                  75                  80

Ala Phe Met Arg Ala Ser Ser Val Leu Lys Ser Leu Pro Phe Pro Ile
                85                  90                  95

Thr Ser Met Lys Asp Thr Glu Gly Ile Pro Cys Leu Gly Asp Lys Val
            100                 105                 110

Lys Ser Ile Ile Glu Gly Ile Ile Glu Asp Gly Glu Ser Ser Glu Ala
        115                 120                 125

Lys Ala Val Leu Asn Asp Glu Arg Tyr Lys Ser Phe Lys Leu Phe Thr
    130                 135                 140

Ser Val Phe Gly Val Gly Leu Lys Thr Ala Glu Lys Trp Phe Arg Met
145                 150                 155                 160

Gly Phe Arg Thr Leu Ser Lys Ile Gln Ser Asp Lys Ser Leu Arg Phe
                165                 170                 175

Thr Gln Met Gln Lys Ala Gly Phe Leu Tyr Tyr Glu Asp Leu Val Ser
            180                 185                 190

Cys Val Asn Arg Pro Glu Ala Glu Ala Val Ser Met Leu Val Lys Glu
        195                 200                 205

Ala Val Val Thr Phe Leu Pro Asp Ala Leu Val Thr Met Thr Gly Gly
    210                 215                 220

Phe Arg Arg Gly Lys Met Thr Gly His Asp Val Asp Phe Leu Ile Thr
225                 230                 235                 240

Ser Pro Glu Ala Thr Glu Asp Glu Glu Gln Gln Leu Leu His Lys Val
                245                 250                 255

Thr Asp Phe Trp Lys Gln Gln Gly Leu Leu Leu Tyr Cys Asp Ile Leu
            260                 265                 270
```

```
Glu Ser Thr Phe Glu Lys Phe Lys Gln Pro Ser Arg Lys Val Asp Ala
            275                 280                 285

Leu Asp His Phe Gln Lys Cys Phe Leu Ile Leu Lys Leu Asp His Gly
        290                 295                 300

Arg Val His Ser Glu Lys Ser Gly Gln Glu Gly Lys Gly Trp Lys
305                 310                 315                 320

Ala Ile Arg Val Asp Leu Val Met Cys Pro Tyr Asp Arg Arg Ala Phe
                325                 330                 335

Ala Leu Leu Gly Trp Thr Gly Ser Arg Gln Phe Glu Arg Asp Leu Arg
            340                 345                 350

Arg Tyr Ala Thr His Glu Arg Lys Met Met Leu Asp Asn His Ala Leu
        355                 360                 365

Tyr Asp Arg Thr Lys Arg Val Phe Leu Glu Ala Glu Ser Glu Glu Glu
    370                 375                 380

Ile Phe Ala His Leu Gly Leu Asp Tyr Ile Glu Pro Trp Glu Arg Asn
385                 390                 395                 400

Ala

<210> SEQ ID NO 5
<211> LENGTH: 20
<212> TYPE: DNA
<213> ORGANISM: artificial sequence
<220> FEATURE:
<223> OTHER INFORMATION: T7-pro primer

<400> SEQUENCE: 5
taatacgact cactataggg                                              20

<210> SEQ ID NO 6
<211> LENGTH: 19
<212> TYPE: DNA
<213> ORGANISM: artificial sequence
<220> FEATURE:
<223> OTHER INFORMATION: T7-ter primer

<400> SEQUENCE: 6
gctagttatt gctcagcgg                                               19

<210> SEQ ID NO 7
<211> LENGTH: 18
<212> TYPE: DNA
<213> ORGANISM: artificial sequence
<220> FEATURE:
<223> OTHER INFORMATION: primer

<400> SEQUENCE: 7
aaaaaaaaaa aaaagggg                                                18

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8 ttttttttttt ttaaataagg                                             20

<210> SEQ ID NO 9
<211> LENGTH: 401
<212> TYPE: PRT
<213> ORGANISM: artificial sequence
```

<220> FEATURE:
<223> OTHER INFORMATION: Reference TdT variant

<400> SEQUENCE: 9

```
Thr Met Gly Ser Ser His His His His His Ser Ser Gly Leu Val
1               5                   10                  15

Pro Arg Gly Ser His Met Ser Pro Ser Pro Val Pro Gly Ser Gln Asn
                20                  25                  30

Val Pro Ala Pro Ala Val Lys Lys Ile Ser Gln Tyr Ala Cys Gln Arg
            35                  40                  45

Arg Thr Thr Leu Asn Asn Tyr Asn Gln Leu Phe Thr Asp Ala Leu Asp
        50                  55                  60

Ile Leu Ala Glu Asn Asp Glu Leu Arg Glu Asn Glu Gly Ser Cys Leu
65                  70                  75                  80

Ala Phe Met Arg Ala Ser Ser Val Leu Lys Ser Leu Pro Phe Pro Ile
                85                  90                  95

Thr Ser Met Lys Asp Thr Glu Gly Ile Pro Cys Leu Gly Asp Lys Val
                100                 105                 110

Lys Ser Ile Ile Glu Gly Ile Ile Glu Asp Gly Glu Ser Ser Glu Ala
            115                 120                 125

Lys Ala Val Leu Asn Asp Glu Arg Tyr Lys Ser Phe Lys Leu Phe Thr
130                 135                 140

Ser Val Phe Gly Val Gly Leu Lys Thr Ala Glu Lys Trp Phe Arg Met
145                 150                 155                 160

Gly Phe Arg Thr Leu Ser Lys Ile Gln Ser Asp Lys Ser Leu Arg Phe
                165                 170                 175

Thr Gln Met Gln Lys Ala Gly Phe Leu Tyr Tyr Glu Asp Leu Val Ser
            180                 185                 190

Cys Val Asn Arg Pro Glu Ala Glu Ala Val Ser Met Leu Val Lys Glu
                195                 200                 205

Ala Val Val Thr Phe Leu Pro Asp Ala Leu Val Thr Met Thr Gly Gly
            210                 215                 220

Phe Arg Arg Gly Lys Met Thr Gly His Asp Val Asp Phe Leu Ile Thr
225                 230                 235                 240

Ser Pro Glu Ala Thr Glu Asp Glu Glu Gln Gln Leu Leu His Lys Val
                245                 250                 255

Thr Asp Phe Trp Lys Gln Gln Gly Leu Leu Leu Tyr Cys Asp Ile Leu
            260                 265                 270

Glu Ser Thr Phe Glu Lys Phe Lys Gln Pro Ser Arg Lys Val Asp Ala
        275                 280                 285

Leu Asp His Phe Gln Lys Cys Phe Leu Ile Leu Lys Leu Asp His Gly
    290                 295                 300

Arg Val His Ser Glu Lys Ser Gly Gln Gln Glu Gly Lys Gly Trp Lys
305                 310                 315                 320

Ala Ile Arg Val Asp Leu Val Met Cys Pro Tyr Asp Arg Arg Ala Phe
                325                 330                 335

Ala Leu Leu Gly Trp Thr Gly Ser Ala Gln Phe Ser Arg Asp Leu Arg
            340                 345                 350

Arg Tyr Ala Thr His Glu Arg Lys Met Met Leu Asp Asn His Ala Leu
        355                 360                 365
```

```
Tyr Asp Arg Thr Lys Arg Val Phe Leu Glu Ala Glu Ser Glu Glu Glu
        370             375             380

Ile Phe Ala His Leu Gly Leu Asp Tyr Ile Glu Pro Trp Glu Arg Asn
385             390             395             400

Ala
```

VARIANTS OF TERMINAL DEOXYNUCLEOTIDYL TRANSFERASE AND USES THEREOF

CROSS-REFERENCE TO RELATED APPLICATIONS

This application is a continuation of U.S. patent application Ser. No. 16/423,972, filed May 28, 2019, which application is a continuation-in-part of U.S. patent application Ser. No. 16/242,904, filed Jan. 8, 2019, issued as U.S. Pat. No. 10,435,676, which application claims priority to European Patent Application Serial No. 18305006.1, filed Jan. 8, 2018, which applications are incorporated by reference herein in their entirety.

INCORPORATION BY REFERENCE OF SEQUENCE LISTING PROVIDED AS A TEXT FILE

A sequence Listing is provided herewith as a text file, (DNAS-004CON_806US03_SeqList_ST25), created on (Sep. 28, 2020) and having a size of (19.8 KB). The contents of the text file are incorporated by reference herein in their entirety.

FIELD OF THE INVENTION

The invention relates to variants of Terminal deoxynucleotidyl Transferase (TdT) and uses thereof for the enzymatic synthesis of nucleic acid sequences without template. More particularly, the present invention relates to such variants suitable to incorporate modified nucleotides, for the synthesis of nucleic acid molecules with determined or controlled sequences.

BACKGROUND

Methods for de novo chemical synthesis of nucleic acids based on solid-phase phosphoramidite chemistry have been largely used and refined over the past 40 years. The technique consists of a four-step chain elongation cycle that adds one base per cycle onto a growing oligonucleotide chain attached to a solid support matrix. Although it has been the method of choice to synthesize nucleic acids during the past decades, this technology has some notable limitations: It requires the use of multiple solvents and reagents, and due to limitations in chemical reaction efficiency, the length of synthetic oligonucleotides typically do not exceed 150-200 bases. Moreover, these short fragments need to be further assembled to provide the desired DNA sequence.

One alternative to chemical synthesis consists in using template independent DNA polymerases that will add reversible terminator modified nucleotides to a growing single stranded chain of nucleic acids. This allows the addition of one type of nucleotide per cycle in a controlled fashion.

Some native enzymes are able to act on natural nucleotides in the absence of template and so can catalyze the synthesis of nucleic acids in an uncontrolled fashion. However, they are particularly inefficient to incorporate modified nucleotides and more particularly reversible terminator modified nucleotides. Efforts have been made to develop new DNA polymerases able to act on modified nucleotides but the resulting enzymes are not fully satisfactory in terms of performances for the synthesis of any type of nucleic acids.

So far, only few DNA polymerases that can act efficiently on single strand DNA (without the use of template) have been identified. The most characterized polymerase having such template-independent activity is the Terminal deoxynucleotidyl Transferase (TdT). TdT enzymes have been extensively used to modify single stranded DNA for various types of applications including biotechnology, biomedical research and synthetic biology. However, native TdT is poorly able to use modified nucleotides.

Several attempts to develop modified TdT with acceptable performance for the incorporation of modified nucleotides have been carried over. However, the performances of the incorporation of such modified nucleotides is still a limiting factor. Incorporation efficiency is the key parameter driving the overall purity and yield of synthesis. These two characteristics of the synthesis process have a significant impact of quality, turnaround time and cost of nucleic acid products.

There is therefore a need to develop improved TdT capable to use modified nucleotides in the absence of template, for developing efficient and cost-effective methods for the nucleic acid synthesis.

SUMMARY OF THE INVENTION

By working on TdT for de novo synthesis of polynucleotides with controlled sequence and without the use of a template, the inventors have discovered that some targeted amino acid residues of the catalytic domain of the TdT may be specifically modified to improve the ability of such modified TdT for synthesizing polynucleotides. More particularly, the inventors have developed modified TdTs with targeted amino acid substitution(s) that lead to improve the enzymatic synthesis of polynucleotides and to reduce the overall cost of synthesizing polynucleotides. In some embodiments, each of the modified TdTs presents one or more targeted amino acids substitution as compared to wild-type TdTs (such as SEQ ID NOs:1, 10, 12, 14, 16, 18, 20, 22, 24, 26, 28, 30, 32 or 34) and N-terminal truncated versions thereof that comprise a TdT catalytic domain. In some embodiments, each of the modified TdTs of the invention possesses an amino acid sequence having a specified percent sequence identity with a catalytic domain of a TdT (such as SEQ ID NOs:2, 11, 13, 15, 17, 19, 21, 23, 25, 27, 29, 31, 33 or 35) and having one or more specified amino acid substitution(s). The template-independent polymerases of the invention allow the enzymatic synthesis of polynucleotides at a faster rate, with less expense and higher quality.

It is therefore an object of the invention to provide variants of Terminal deoxynucleotidyl Transferase (TdT) which (i) comprise an amino acid sequence of a TdT catalytic domain or of a percent sequence identity of a TdT catalytic domain, such as set forth in SEQ ID NOs 2, 11, 13, 15, 17, 19, 21, 23, 25, 27, 29, 31, 33 or 35, with at least an amino acid substitution at position corresponding to residue C302 (with respect to the amino acid numbering of SEQ ID NO: 1), or functionally equivalent residue, (ii) is capable of synthesizing a nucleic acid fragment without template and (iii) is capable of incorporating a modified nucleotide, such as a 3'-O-modified nucleotide onto a free 3'-hydroxyl of a nucleic fragment.

More particularly, it is an object of the present invention to provide terminal deoxynucleotidyl transferase (TdT) variants comprising an amino acid sequence at least 90% identical to SEQ ID NO: 2, 11, 13, 15, 17, 19, 21, 23, 25, 27, 29, 31, 33 or 35 with a substitution at position corresponding to residue C173 with respect to SEQ ID NOs 2, 11, 13, 17, 19, 21, 29 or 31, or at position corresponding to residue C172 with respect to SEQ ID NO: 15, or at position corresponding to residue C178 with respect to SEQ ID NO: 23, or at position corresponding to residue C174 with respect to SEQ ID NO: 25, or at position corresponding to residue C171 with respect to SEQ ID NO: 27, or at position corresponding to residue C182 with respect to SEQ ID NO: 33, or at position corresponding to residue C176 with respect to SEQ ID NO: 35, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity.

Advantagesously, in regard to (iii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In a particular embodiment, the substitution is selected from:
C302G/R/P/A/V/S/N/Q/D with respect to SEQ ID NO:1; or C173G/R/P/A/V/S/N/Q/D with respect to SEQ ID NO:2; or
C313G/R/P/A/V/S/N/Q/D with respect to SEQ ID NO: 10; or C173G/R/P/A/V/S/N/Q/D with respect to SEQ ID NO:11; or C302G/R/P/A/V/S/N/Q/D with respect to SEQ ID NO:12; or C173G/R/P/A/V/S/N/Q/D with respect to SEQ ID NO: 13; or C302G/R/P/A/V/S/N/Q/D with respect to SEQ ID NO:14; or C172G/R/P/A/V/S/N/Q/D with respect to SEQ ID NO:15; or C304G/R/P/A/V/S/N/Q/D with respect to SEQ ID NO:16; or C173G/R/P/A/V/S/N/Q/D with respect to SEQ ID NO:17; or C304G/R/P/A/V/S/N/Q/D with respect to SEQ ID NO:18; or C173G/R/P/A/V/S/N/Q/D with respect to SEQ ID NO:19; or C293G/R/P/A/V/S/N/Q/D with respect to SEQ ID NO:20; or C174G/R/P/A/V/S/N/Q/D with respect to SEQ ID NO:21; or C282G/R/P/A/V/S/N/Q/D with respect to SEQ ID NO:22; or C173G/R/P/A/V/S/N/Q/D with respect to SEQ ID NO:23; or C304G/R/P/A/V/S/N/Q/D with respect to SEQ ID NO:24; or C174G/R/P/A/V/S/N/Q/D with respect to SEQ ID NO:25; or C300G/R/P/A/V/S/N/Q/D with respect to SEQ ID NO:26; or C171G/R/P/A/V/S/N/Q/D with respect to SEQ ID NO:27; or C305G/R/P/A/V/S/N/Q/D with respect to SEQ ID NO:28; or C173G/R/P/A/V/S/N/Q/D with respect to SEQ ID NO:29; or C302G/R/P/A/V/S/N/Q/D with respect to SEQ ID NO:30; or C173G/R/P/A/V/S/N/Q/D with respect to SEQ ID NO:31; or C313G/R/P/A/V/S/N/Q/D with respect to SEQ ID NO:32; or C182G/R/P/A/V/S/N/Q/D with respect to SEQ ID NO:33; or C271G/R/P/A/V/S/N/Q/D with respect to SEQ ID NO:34; or C176G/R/P/A/V/S/N/Q/D with respect to SEQ ID NO:35.

In a further embodiment, the substitution is selected from:
C302G/R with respect to SEQ ID NO:1; or C302G/R with respect to SEQ ID NO:1; or C173G/R with respect to SEQ ID NO:2; or C302G/R with respect to SEQ ID NO:4; or C302G/R with respect to SEQ ID NO:9; or C313G/R with respect to SEQ ID NO:10; or C173G/R with respect to SEQ ID NO: 11; or C302G/R with respect to SEQ ID NO:12; or C173G/R with respect to SEQ ID NO:13; or C302G/R with respect to SEQ ID NO:14; or C172G/R with respect to SEQ ID NO:15; or C304G/R with respect to SEQ ID NO:16; or C173G/R with respect to SEQ ID NO:17; or C304G/R with respect to SEQ ID NO:18; or C173G/R with respect to SEQ ID NO:19; or C293G/R with respect to SEQ ID NO:20; or C173G/R with respect to SEQ ID NO:21; or C282G/R with respect to SEQ ID NO:22; or C173G/R with respect to SEQ ID NO:23; or C304G/R with respect to SEQ ID NO:24; or C174G/R with respect to SEQ ID NO:25; or C300G/R with respect to SEQ ID NO:26; or C171G/R with respect to SEQ ID NO:27; or C305G/R with respect to SEQ ID NO:28; or C173G/R with respect to SEQ ID NO:29; or C302G/R with respect to SEQ ID NO:30; or C173G/R with respect to SEQ ID NO:31; or C313G/R with respect to SEQ ID NO:32; or C182G/R with respect to SEQ ID NO:33; or C271G/R with respect to SEQ ID NO:34; or C176G/R with respect to SEQ ID NO:35.

In some embodiments, the invention is directed to compositions comprising TdT variants comprising amino acid sequence having at least 90 percent identity, or in some embodiments, at least 95 percent identity, or in some embodiments, at least 97 percent identity, or in some embodiments, at least 98 percent identity, with a reference or wild type TdT sequence selected from the group consisting of SEQ ID NOs: 2, 11, 13, 15, 17, 19, 21, 23, 25, 27, 29, 31, 33 and 35, wherein (i) such TdT variants have a mutation selected from C173G/R/P/A/V/S/N/Q/D, such as C173G/R (wherein the amino acid residue number is with respect to SEQ ID NO: 2, or an equivalent residue number of SEQ ID NOs 11, 13, 15, 17, 19, 21, 23, 25, 27, 29, 31, 33 or 35) and (ii) such TdT variants incorporate a modified nucleotide, such as a 3'-O-modified nucleoside triphosphates, with greater efficiency, or at a higher rate, than the reference or wild type TdT.

In some embodiments, it is also an object of the invention to provide truncated variants of Terminal deoxynucleotidyl Transferase (TdT) each of which (i) comprises an amino acid sequence with at least 95 percent identity to any of SEQ ID NOs:11, 13, 15, 17, 19, 21, 23, 25, 27, 29, 31, 33 or 35 with at least two amino acid substitutions, such as at least three amino acid substitutions, selected from M192R/Q, L260P, C302G/R, R336IJN, D379V, R454P/N and E457N/IJT/S, (wherein residue numbers are with respect to SEQ ID NO:1 or with respect to their functionally equivalent residues numbers in SEQ ID NOs 11, 13, 15, 17, 19, 21, 23, 25, 27, 29, 31, 33 or 35), (ii) is able to synthesize a nucleic acid fragment without a template and (iii) is able to incorporate a modified nucleotide into the nucleic acid fragment, for example, a 3'-O-reversibly blocked deoxynucleoside triphosphate onto a free 3'-hydroxyl of a nucleic acid fragment. In further embodiments, the above percent sequence identity value is at least 98 percent identity with the specified sequences.

It is another object of the invention to provide a nucleic acid molecule encoding a variant of a TdT as defined above and/or an expression vector comprising such nucleic acid molecule, and/or a host cell comprising such nucleic acid molecule or expression vector.

It is a further object of the invention to provide a process for producing a variant of TdT according to the invention, wherein a host cell as defined above is cultivated under culture conditions allowing the expression of the nucleic acid encoding said variant, and wherein the variant is optionally retrieved.

The invention further relates to the use of a variant of TdT, for synthesizing a nucleic acid molecule without template, by the successive addition of one or more 3'O-modified nucleotides to a nucleic acid fragment. In some embodiments, such methods comprise the steps of (a) providing an initiator comprising an oligonucleotide having a free 3'-hydroxyl; (b) reacting under enzymatic extension conditions a TdT variant of the invention with the initiator or an extended initiator in the presence of a 3'-O-reversibly blocked nucleoside. In some embodiments, such method further includes steps of (c) deblocking the extended initiators to form extended initiators with free 3'-hydroxyls and (d) repeating steps (b) and (c) until a nucleic acid molecule of a predetermined sequence is synthesized.

It is also an object of the invention to provide a process for synthesizing a nucleic acid molecule without template, comprising a step of contacting a nucleic acid primer with both at least one nucleotide, such as at least one modified nucleotides, such as a 3'O-modified nucleotide, and a variant of TdT according to the invention.

The present invention further provides a kit for performing a nucleotide incorporation reaction comprising a variant of TdT according to the invention, and one or more nucleotides, such as one or more modified nucleotides, such as a 3'O-modified nucleotides, and optionally at least one nucleic acid primer.

DESCRIPTION OF THE INVENTION

Figure 1:
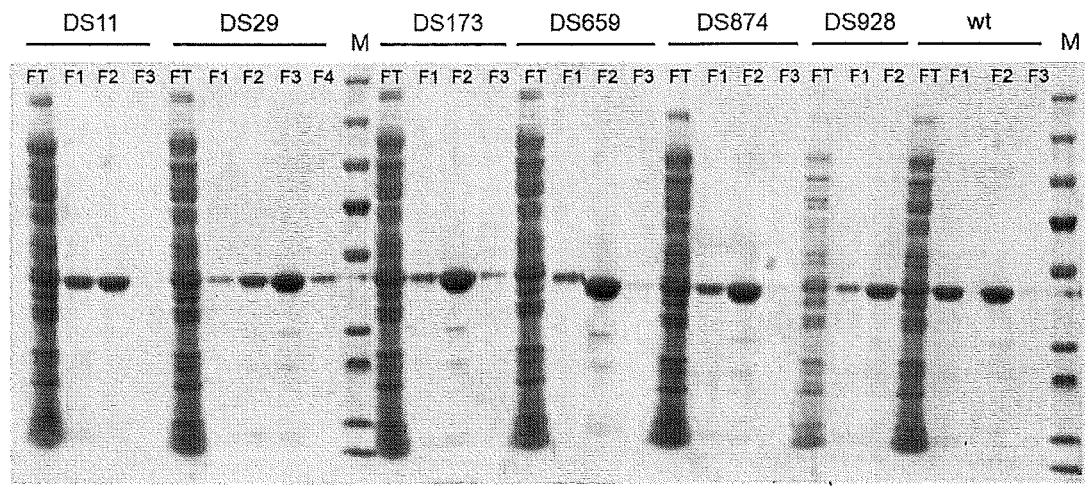
FIG. 1: Purification assay of wild type (wt) TdT and different TdT variants of the invention. Protein samples were loaded on SDS-PAGE analysis gel and migrated through electrophoresis.

The DNA polymerase families are divided into seven families based on their sequence homology and crystal structure. Among them, the polymerases of PolX family represent a wide variety of polymerases from replicative polymerases to terminal transferase enzymes. Polymerases from PolX family are present across a very wide range of eukaryotic organisms. Polymerases from the PolX family are implicated in a vast variety of biological processes and in particular in DNA damage repair mechanisms or error correction mechanisms. The PolX family regroups polymerase β (Pol β), μ(Pol μ), λ (Pol λ), IV from yeast (Pol IV) and the Terminal deoxynucleotidyl Transferase (TdT). TdT is naturally implicated in DNA repair and maintenance mechanisms. In particular, TdT has the unique ability to conserve a nucleotide polymerization activity even in absence of template strand. In specific conditions and with natural nucleotides, TdT is able to elongate DNA fragments with several hundred nucleotides, in absence of any complementary strand. However, wild type TdT is totally unable to efficiently incorporate sugar-modified nucleotides.

It is thus the purpose of the present invention to provide variants of TdT with targeted mutation(s) that allow them to incorporate modified nucleotides into a nucleic fragment during synthesize of said nucleotide fragment. More particularly, the inventors have identified specific amino acid residues that may be advantageously substituted, alone or in combination, to improve the ability of the enzyme to synthesize nucleic acid fragments of various length and with pre-determined sequence, including by using modified nucleotides.

Definitions

As used therein, the terms "mutant" and "variant" may be used interchangeably to refer to polypeptides related to or derived from SEQ ID NOs:2, 11, 12, 13, 14, 15, 16, 17, 18, 19, 20, 21, 22, 23, 24, 25, 26 27, 28, 29, 30, 31, 32, 33, 34 or 35 and comprising a modification or an alteration, i.e., a substitution, insertion, and/or deletion, at one or more (e.g., several) positions and having both a polymerase activity without template and ability to incorporate 3'-O-modified nucleoside triphosphates into a nucleic acid chain. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction. Mutagenesis activities consist in deleting, inserting or substituting one or several amino-acids in the sequence of a protein or in the case of the invention of a polymerase. Targeted amino-acids could be concomitant or distributed along the whole sequence of the polymerase. Specific motifs or structural features could be targeted for example.

The terms "modification" or "alteration" as used herein in relation to a position or amino acid mean that the amino acid in the specific position has been modified compared to the amino acid of the wild-type protein.

A "substitution" means that an amino acid residue is replaced by another amino acid residue. For example, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). For example, the term "substitution" refers to the replacement of an amino acid residue by another selected from the naturally-occurring standard 20 amino acid residues. The sign "+" indicates a combination of substitutions.

The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

As used herein, the terms "sequence identify" or "identity" refer to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are aligned using a global alignment algorithm (e.g. Needleman and Wunsch algorithm; Needleman and Wunsch, 1970) which aligns the sequences optimally over the entire length, while sequences of substantially different lengths are aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/ or http://www.ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are i5 set to default values, i.e. Scoring matrix=BLOSUM62, Gap open=10, Gap extend=0.5, End gap penalty=false, End gap open=10 and End gap extend=0.5.

Herein, the terms "peptide", "polypeptide", "protein", "enzyme", refer to a chain of amino acids linked by peptide bonds, regardless of the number of amino acids forming said chain.

Unless otherwise specified, the positions disclosed in the present application are numbered by reference to the amino acid sequence set forth in a specified SEQ ID NO.

Variants of TdT

The present invention provides variants of TdT enzyme that can be used for synthesizing polynucleotides of predetermined sequences, such as DNA or RNA, without the use of template strand. The TdT variants of the invention allow modified nucleotides, and more particularly 3'O-modified nucleotides, to be used in an enzyme-mediated method of polynucleotide synthesis, such as described by Hiatt et al, U.S. Pat. No. 5,763,594.

In some embodiments of the invention, "modified Terminal desoxyribonucleotidyl Transferase", "modified TdT", "variants of Terminal desoxyribonucleotidyl Transferase" and "variants of TdT" refer to enzymes that comprise an amino acid seqment that shares at least 80% identity with an amino acid sequence of one of the amino acid sequences set forth in SEQ ID NOs:2, 11, 13, 15, 17, 19, 21, 23, 25, 27, 29, 31, 33 or 35, excepting at least one amino acid residue substitution. In some embodiments, the variant of TdT comprises an amino acid sequence that shares at least 90% identity with SEQ ID NOs:2, 11, 13, 15, 17, 19, 21, 23, 25, 27, 29, 31, 33, 35, and having at least one amino acid residue substitution. In still other embodiments, the variant of TdT comprises an amino acid sequence that shares at least 95% identity with SEQ ID NOs:2, 11, 13, 15, 17, 19, 21, 23, 25, 27, 29, 31, 33, 35, and having at least one amino acid residue substitution. In still other embodiments, the variant of TdT comprises an amino acid sequence that shares at least 98% identity with SEQ ID NOs:2, 11, 13, 15, 17, 19, 21, 23, 25, 27, 29, 31, 33, 35, and having at least one amino acid residue substitution.

In some cases, variants of the present invention may be described according to their mutations on specific residues, whose positions are determined by alignment with or reference to the enzymatic sequence SEQ ID NO:1 or SEQ ID NO:2, which corresponds to the amino acid sequences of murine TdT and truncated murine TdT respectively. The variants of the invention may also be described directly with reference to SEQ ID numbers of corresponding reference sequences.

By "functionally equivalent residue" is meant a residue in a sequence of a TdT of sequence homologous to SEQ ID NO:1 or to SEQ ID NO:2 and having an identical functional role. Functionally equivalent residues are identified by using sequence alignments, for example, using the Mutalin line alignment software (http://multalin.toulouse.inra.fr/multalin/multalin.html; 1988, Nucl. Acids Res., 16 (22), 10881-10890). After alignment, the functionally equivalent residues are at homologous positions on the different sequences considered. Sequence alignments and identification of functionally equivalent residues may be between any TdT and their natural variants, including inter-species.

TdT can be found in many organisms or microorganisms. All those TdT are good candidates for performing the present invention. In particular, modifications to alter a particular TdT sequence to give said polymerase an increased ability to incorporate modified nucleotides, can target any other TdT sequence. Accordingly, mutations or combinations described herein by reference to SEQ ID NO:1, and more particularly to SEQ ID NO:2 that corresponds to amino acid residues 130 to 510 of SEQ ID NO:1, can be transposed to any other TdT sequence.

In some embodiments, the invention comprises a variant of Terminal deoxynucleotidyl Transferase (TdT) that (i) comprises an amino acid sequence having at least 80%, such as at least 85%, 90%, 95% or 99% identity with an amino acid sequence selected from SEQ ID NO: 2, 11, 13, 15, 17, 19, 21, 23, 25, 27, 29, 31, 33 or 35, with at least an amino acid substitution at position corresponding to a functionally equivalent residue of residue C173 with respect to SEQ ID NO:11, (ii) is able to synthesize a nucleic acid fragment without template and (iii) is able to incorporate a modified nucleoside triphosphate, such as a 3'-O-blocked nucleoside triphosphate, into the nucleic fragment.

Indeed, the inventors have discovered that such substitution has a great impact on both surface and interaction properties of the enzyme with nucleotides, which may allow incorporation of 3'O-modified nucleotides in a nucleic acid sequence.

Further embodiments of TdT variants of the invention are listed as entries in Tables 1A through 1C (single substitutions), Tables 2A through 2C (two substitutions), Tables 3A through 3C (three substitutions), and Tables 4A through 4F (four substitutions), wherein each such variant TdT is defined by the indicated SEQ ID NO in the righthand column modified by the substitution(s) listed in the lefthand column of the same row as the SEQ ID NO. A "non-wild type" substitution means that the substitution may be any amino acid except for the amino acid at the indicated position in the wild type sequence, or equivalently, the sequence of the indicated SEQ ID NO.

TABLE 1A

TdT variants at position C173 (SEQ ID NO: 2) or functionally equivalent positions of the indicated SEQ ID NO

| Non-wild type substitution at | SEQ ID NO |
|---|---|
| C173 | 2 |
| C313 | 10 |
| C173 | 11 |
| C302 | 12 |
| C173 | 13 |
| C302 | 14 |
| C172 | 15 |
| C304 | 16 |
| C173 | 17 |
| C304 | 18 |
| C173 | 19 |
| C293 | 20 |
| C173 | 21 |
| C282 | 22 |
| C178 | 23 |
| C304 | 24 |
| C174 | 25 |
| C300 | 26 |
| C171 | 27 |
| C305 | 28 |
| C173 | 29 |
| C302 | 30 |
| C173 | 31 |
| C313 | 32 |
| C182 | 33 |
| C271 | 34 |
| C176 | 35 |

TABLE 1B

Further TdT variants at position C173 (SEQ ID NO: 2) or functionally equivalent positions of the indicated SEQ ID NO

| Substitution | SEQ ID NO |
|---|---|
| C173/G/R/P/A/V/S/N/Q/D | 2 |
| C313/G/R/P/A/V/S/N/Q/D | 10 |
| C173/G/R/P/A/V/S/N/Q/D | 11 |
| C302/G/R/P/A/V/S/N/Q/D | 12 |
| C173/G/R/P/A/V/S/N/Q/D | 13 |
| C302/G/R/P/A/V/S/N/Q/D | 14 |
| C172/G/R/P/A/V/S/N/Q/D | 15 |
| C304/G/R/P/A/V/S/N/Q/D | 16 |
| C173/G/R/P/A/V/S/N/Q/D | 17 |
| C304/G/R/P/A/V/S/N/Q/D | 18 |
| C173/G/R/P/A/V/S/N/Q/D | 19 |
| C293/G/R/P/A/V/S/N/Q/D | 20 |
| C173/G/R/P/A/V/S/N/Q/D | 21 |
| C282/G/R/P/A/V/S/N/Q/D | 22 |
| C178/G/R/P/A/V/S/N/Q/D | 23 |
| C304/G/R/P/A/V/S/N/Q/D | 24 |
| C174/G/R/P/A/V/S/N/Q/D | 25 |
| C300/G/R/P/A/V/S/N/Q/D | 26 |
| C171/G/R/P/A/V/S/N/Q/D | 27 |
| C305/G/R/P/A/V/S/N/Q/D | 28 |
| C173/G/R/P/A/V/S/N/Q/D | 29 |
| C302/G/R/P/A/V/S/N/Q/D | 30 |
| C173/G/R/P/A/V/S/N/Q/D | 31 |
| C313/G/R/P/A/V/S/N/Q/D | 32 |
| C182/G/R/P/A/V/S/N/Q/D | 33 |
| C271/G/R/P/A/V/S/N/Q/D | 34 |
| C176/G/R/P/A/V/S/N/Q/D | 35 |

TABLE 1C

Further TdT variants at position C173 (SEQ ID NO: 2) or functionally equivalent positions of the indicated SEQ ID NO

| Substitutions | SEQ ID NO |
|---|---|
| C173/G/R | 2 |
| C313/G/R | 10 |
| C173/G/R | 11 |
| C302/G/R | 12 |
| C173/G/R | 13 |
| C302/G/R | 14 |
| C172/G/R | 15 |
| C304/G/R | 16 |
| C173/G/R | 17 |
| C304/G/R | 18 |
| C173/G/R | 19 |
| C293/G/R | 20 |
| C173/G/R | 21 |
| C282/G/R | 22 |
| C178/G/R | 23 |
| C304/G/R | 24 |
| C174/G/R | 25 |
| C300/G/R | 26 |
| C171/G/R | 27 |
| C305/G/R | 28 |
| C173/G/R | 29 |
| C302/G/R | 30 |
| C173/G/R | 31 |
| C313/G/R | 32 |
| C182/G/R | 33 |
| C271/G/R | 34 |
| C176/G/R | 35 |

TABLE 2A

Further TdT variants at position C173 (SEQ ID NO: 2) and position M63 (SEQ ID NO: 2) or functionally equivalent positions of the indicated SEQ ID NO

| Non-wildtype substitutions at locations | SEQ ID NO |
|---|---|
| M63 + C173 | 2 |
| M63 + C173 | 11 |
| M63 + C173 | 13 |
| L62 + C172 | 15 |
| M63 + C173 | 17 |
| M63 + C173 | 19 |
| R64 + C173 | 21 |
| M73 + C178 | 23 |
| M64 + C174 | 25 |
| M61 + C171 | 27 |
| M63 + C173 | 29 |
| L63 + C173 | 31 |
| M63 + C182 | 33 |
| M66 + C176 | 35 |

TABLE 2B

Further TdT variants at position C173 (SEQ ID NO: 2) and position M63 (SEQ ID NO: 2) or functionally equivalent positions of the indicated SEQ ID NO

| Substitutions and substitution positions | SEQ ID NO |
|---|---|
| M63R/Q/G/A/V/D/N/H/E + C173G/R/P/A/V/S/N/Q/D | 2 |
| M63R/Q/G/A/V/D/N/H/E + C173G/R/P/A/V/S/N/Q/D | 11 |
| M63R/Q/G/A/V/D/N/H/E + C173G/R/P/A/V/S/N/Q/D | 13 |

TABLE 2B-continued

Further TdT variants at position C173 (SEQ ID NO: 2) and position M63 (SEQ ID NO: 2) or functionally equivalent positions of the indicated SEQ ID NO

| Substitutions and substitution positions | SEQ ID NO |
|---|---|
| L62R/Q/G/A/V/D/N/H/E + C172G/R/P/A/V/S/N/Q/D | 15 |
| M63R/Q/G/A/V/D/N/H/E + C173G/R/P/A/V/S/N/Q/D | 17 |
| M63R/Q/G/A/V/D/N/H/E + C173G/R/P/A/V/S/N/Q/D | 19 |
| R64R/Q/G/A/V/D/N/H/E + C173G/R/P/A/V/S/N/Q/D | 21 |
| M73R/Q/G/A/V/D/N/H/E + C178G/R/P/A/V/S/N/Q/D | 23 |
| M64R/Q/G/A/V/D/N/H/E + C174G/R/P/A/V/S/N/Q/D | 25 |
| M61R/Q/G/A/V/D/N/H/E + C171G/R/P/A/V/S/N/Q/D | 27 |
| M63R/Q/G/A/V/D/N/H/E + C173G/R/P/A/V/S/N/Q/D | 29 |
| L63R/Q/G/A/V/D/N/H/E + C173G/R/P/A/V/S/N/Q/D | 31 |
| M63R/Q/G/A/V/D/N/H/E + C182G/R/P/A/V/S/N/Q/D | 33 |
| M66R/Q/G/A/V/D/N/H/E + C176G/R/P/A/V/S/N/Q/D | 35 |

TABLE 2C

Further TdT variants at position C173 (SEQ ID NO: 2) and position M63 (SEQ ID NO: 2) or functionally equivalent positions of the indicated SEQ ID NO

| Substitutions and substitution positions | SEQ ID NO |
|---|---|
| M63R/Q + C173G/R | 2 |
| M63R/Q + C173G/R | 11 |
| M63R/Q + C173G/R | 13 |
| L62R/Q + C172G/R | 15 |
| M63R/Q + C173G/R | 17 |
| M63R/Q + C173G/R | 19 |
| R64R/Q + C173G/R | 21 |
| M73R/Q + C178G/R | 23 |
| M64R/Q + C174G/R | 25 |
| M61R/Q + C171G/R | 27 |
| M63R/Q + C173G/R | 29 |
| L63R/Q + C173G/R | 31 |
| M63R/Q + C182G/R | 33 |
| M66R/Q + C176G/R | 35 |

TABLE 3A

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M63 + C173 + R207 | 2 |
| M63 + C173 + R207 | 11 |
| M63 + C173 + R207 | 13 |
| L62 + C172 + R206 | 15 |
| M63 + C173 + R207 | 17 |
| M63 + C173 + R207 | 19 |
| R64 + C173 + R208 | 21 |
| M73 + C178 + R207 | 23 |
| M64 + C174 + R208 | 25 |
| M61 + C171 + R205 | 27 |
| M63 + C173 + R207 | 29 |
| L63 + C173 + R207 | 31 |
| M63 + C182 + R216 | 33 |
| M66 + C176 + R210 | 35 |

TABLE 3B

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M63R/Q/G/A/V/D/N/H/E + C173G/R/P/A/V/S/N/Q/D + R207N/L/K/H/G/D/A/P | 2 |
| M63R/Q/G/A/V/D/N/H/E + C173G/R/P/A/V/S/N/Q/D + R207 N/L/K/H/G/D/A/P | 11 |
| M63R/Q/G/A/V/D/N/H/E + C173G/R/P/A/V/S/N/Q/D + R207 N/L/K/H/G/D/A/P | 13 |
| L62R/Q/G/A/V/D/N/H/E + C172G/R/P/A/V/S/N/Q/D + R206 N/L/K/H/G/D/A/P | 15 |
| M63R/Q/G/A/V/D/N/H/E + C173G/R/P/A/V/S/N/Q/D + R207 N/L/K/H/G/D/A/P | 17 |
| M63R/Q/G/A/V/D/N/H/E + C173G/R/P/A/V/S/N/Q/D + R207 N/L/K/H/G/D/A/P | 19 |
| R64Q/G/A/V/D/N/H/E + C173G/R/P/A/V/S/N/Q/D + R208 N/L/K/H/G/D/A/P | 21 |
| M73R/Q/G/A/V/D/N/H/E + C178G/R/P/A/V/S/N/Q/D + R207 N/L/K/H/G/D/A/P | 23 |
| M64R/Q/G/A/V/D/N/H/E + C174G/R/P/A/V/S/N/Q/D + R208 N/L/K/H/G/D/A/P | 25 |
| M61R/Q/G/A/V/D/N/H/E + C171G/R/P/A/V/S/N/Q/D + R205 N/L/K/H/G/D/A/P | 27 |
| M63R/Q/G/A/V/D/N/H/E + C173G/R/P/A/V/S/N/Q/D + R207 N/L/K/H/G/D/A/P | 29 |
| L63R/Q/G/A/V/D/N/H/E + C173G/R/P/A/V/S/N/Q/D + R207N/L/IK/H/G/D/A/P | 31 |
| M63R/Q/G/A/V/D/N/H/E + C182G/R/P/A/V/S/N/Q/D 2 + R216N/L/K/H/G/D/A/P | 33 |
| M66R/Q/G/A/V/D/N/H/E + C176G/R/P/A/V/S/N/Q/D + R210N/L/K/H/G/D/A/P | 35 |

TABLE 3C

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M63R/Q + C173G/R + R207L/N | 2 |
| M63R/Q + C173G/R + R207L/N | 11 |
| M63R/Q + C173G/R + R207L/N | 13 |
| M62R/Q + C172G/R + R206L/N | 15 |
| M63R/Q + C173G/R + R207L/N | 17 |

TABLE 3C-continued

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M63R/Q + C173G/R + R207L/N | 19 |
| R64Q + C173G/R + R208L/N | 21 |
| M73R/Q + C178G/R + R207N/L | 23 |
| M64R/Q + C174G/R + R208 NIL | 25 |
| M61R/Q + C171G/R + R205N/L | 27 |
| M63R/Q + C173G/R + R207L/N | 29 |
| L63R/Q + C173G/R + R207L/N | 31 |
| M63R/Q + C182G/R + R216N/L | 33 |
| M66R/Q + C176G/R + R210N/L | 35 |

TABLE 4A

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| M63 + C173 + R207 + R325 | 2 |
| M63 + C173 + R207 + R324 | 11 |
| M63 + C173 + R207 + R324 | 13 |
| L62 + C172 + R206 + R320 | 15 |
| M63 + C173 + R207 + R331 | 17 |
| M63 + C173 + R207 + P325 | 19 |
| R64 + C173 + R208 + T331 | 21 |
| M73 + C178 + R207 + R325 | 23 |
| M64 + C174 + R208 + P326 | 25 |
| M61 + C171 + R205 + R323 | 27 |
| M63 + C173 + R207 + R328 | 29 |
| L63 + C173 + R207 + R325 | 31 |
| M63 + C182 + R216 + R338 | 33 |
| M66 + C176 + R210 + R328 | 35 |

TABLE 4B

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| M63R/Q/G/A/V/D/N/H/E + C173G/R/P/A/V/S/N/Q/D + R207N/L/K/H/G/D/A/P + R325P/N/A/L/K/H/G/D | 2 |
| M63R/Q/G/A/V/D/N/H/E + C173G/R/P/A/V/S/N/Q/D + R207 N/L/K/H/G/D/A/P + R324P/N/A/L/K/H/G/D | 11 |
| M63R/Q/G/A/V/D/N/H/E + C173G/R/P/A/V/S/N/Q/D + R207 N/L/K/H/G/D/A/P + R324P/N/A/L/K/H/G/D | 13 |
| L62R/Q/G/A/V/D/N/H/E + C172G/R/P/A/V/S/N/Q/D + R206 N/L/K/H/G/D/A/P + R320P/N/A/L/K/H/G/D | 15 |
| M63R/Q/G/A/V/D/N/H/E + C173G/R/P/A/V/S/N/Q/D + R207 N/L/K/H/G/D/A/P + R331P/N/A/L/K/H/G/D | 17 |

TABLE 4B-continued

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| M63R/Q/G/A/V/D/N/H/E + C173G/R/P/A/V/S/N/Q/D + R207 N/L/K/H/G/D/A/P + P325N/A/L/K/H/G/D | 19 |
| R64Q/G/A/V/D/N/H/E + C173G/R/P/A/V/S/N/Q/D + R208 N/L/K/H/G/D/A/P + T331P/N/A/L/K/H/G/D | 21 |
| M73R/Q/G/A/V/D/N/H/E + C178G/R/P/A/V/S/N/Q/D + R207 N/L/K/H/G/D/A/P + R325P/N/A/L/K/H/G/D | 23 |
| M64R/Q/G/A/V/D/N/H/E + C174G/R/P/A/V/S/N/Q/D + R208 N/L/K/H/G/D/A/P + P326N/A/L/K/H/G/D | 25 |
| M61R/Q/G/A/V/D/N/H/E + C171G/R/P/A/V/S/N/Q/D + R205 N/L/K/H/G/D/A/P + R323P/N/A/L/K/H/G/D | 27 |
| M63R/Q/G/A/V/D/N/H/E + C173G/R/P/A/V/S/N/Q/D + R207 N/L/K/H/G/D/A/P + R328P/N/A/L/K/H/G/D | 29 |
| L63R/Q/G/A/V/D/N/H/E + C173G/R/P/A/V/S/N/Q/D + R207N/L/K/H/G/D/A/P + R325P/N/A/L/K/H/G/D | 31 |
| M63R/Q/G/A/V/D/N/H/E + C182G/R/P/A/V/S/N/Q/D + R216N/L/K/H/G/D/A/P + R338P/N/A/L/K/H/G/D | 33 |
| M66R/Q/G/A/V/D/N/H/E + C176G/R/P/A/V/S/N/Q/D + R210N/L/K/H/G/D/A/P + R328P/N/A/L/K/H/G/D | 35 |

TABLE 4C

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| M63R/Q + C173G/R + R207N/L + R325P/N | 2 |
| M63R/Q + C173G/R + R207N/L + R324P/N | 11 |
| M63R/Q + C173G/R + R207N/L + R324P/N | 13 |
| L62R/Q + C172G/R + R206N/L + R320P/N | 15 |
| M63R/Q + C173G/R + R207N/L + R331P/N | 17 |
| M63R/Q + C173G/R + R207N/L + P325N | 19 |
| R64Q/G + C173G/R + R208N/L + T331P/N | 21 |
| M73R/Q/G + C178G/R + R207N/L + R325P/N | 23 |
| M64R/Q + C174G/R + R208N/L + P326N | 25 |
| M61R/Q + C171G/R + R205N/L + R323P/N | 27 |
| M63R/Q + C173G/R + R207N/L + R328P/N | 29 |
| L63R/Q + C173G/R + R207N/L + R325P/N | 31 |
| M63R/Q + C182G/R + R216N/L + R338P/N | 33 |
| M66R/Q + C176G/R + R210N/L + R328P/N | 35 |

TABLE 4D

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M63 + C173 + R207 + E328 | 2 |
| M63 + C173 + R207 + E327 | 11 |
| M63 + C173 + R207 + E327 | 13 |
| L62 + C172 + R206 + G323 | 15 |
| M63 + C173 + R207 + E334 | 17 |
| M63 + C173 + R207 + E327 | 19 |
| R64 + C173 + R208 + E334 | 21 |
| M73 + C178 + R207 + E328 | 23 |
| M64 + C174 + R208 + E329 | 25 |
| M61 + C171 + R205 + E326 | 27 |
| M63 + C173 + R207 + E331 | 29 |
| L63 + C173 + R207 + E328 | 31 |
| M63 + C182 + R216 + E341 | 33 |
| M66 + C176 + R210 + E331 | 35 |

TABLE 4E

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M63R/Q/G/A/V/D/N/H/E + C173G/R/P/A/V/S/N/Q/D + R207N/L/K/H/G/D/A/P + E328N/L/T/S | 2 |
| M63R/Q/G/A/V/D/N/H/E + C173G/R/P/A/V/S/N/Q/D + R207 N/L/K/H/G/D/A/P + E327N/L/T/S | 11 |
| M63R/Q/G/A/V/D/N/H/E + C173G/R/P/A/V/S/N/Q/D + R207 N/L/K/H/G/D/A/P + E327N/L/T/S | 13 |
| L62R/Q/G/A/V/D/N/H/E + C172G/R/P/A/V/S/N/Q/D + R206 N/L/K/H/G/D/A/P + G323N/L/T/S | 15 |
| M63R/Q/G/A/V/D/N/H/E + C173G/R/P/A/V/S/N/Q/D + R207 N/L/K/H/G/D/A/P + E334N/L/T/S | 17 |
| M63R/Q/G/A/V/D/N/H/E + C173G/R/P/A/V/S/N/Q/D + R207 N/L/K/H/G/D/A/P + E327N/L/T/S | 19 |
| R64Q/G/A/V/D/N/H/E + C173G/R/P/A/V/S/N/Q/D + R208 N/L/K/H/G/D/A/P + E334N/L/T/S | 21 |
| M73R/Q/G/A/V/D/N/H/E + C178G/R/P/A/V/S/N/Q/D + R207 N/L/K/H/G/D/A/P + E328N/L/T/S | 23 |
| M64R/Q/G/A/V/D/N/H/E + C174G/R/P/A/V/S/N/Q/D + R208 N/L/K/H/G/D/A/P + E329N/L/T/S | 25 |
| M61R/Q/G/A/V/D/N/H/E + C171G/R/P/A/V/S/N/Q/D + R205 N/L/K/H/G/D/A/P + E326N/L/T/S | 27 |
| M63R/Q/G/A/V/D/N/H/E + C173G/R/P/A/V/S/N/Q/D + R207 N/L/K/H/G/D/A/P + E331N/L/T/S | 29 |
| L63R/Q/G/A/V/D/N/H/E + C173G/R/P/A/V/S/N/Q/D + R207N/L/K/H/G/D/A/P + E328N/L/T/S | 31 |
| M63R/Q/G/A/V/D/N/H/E + C182G/R/P/A/V/S/N/Q/D + R216N/L/K/H/G/D/A/P + E341N/L/T/S | 33 |
| M66R/Q/G/A/V/D/N/H/E + C176G/R/P/A/V/S/N/Q/D + R210N/L/K/H/G/D/A/P + E331N/L/T/S | 35 |

TABLE 4F

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M63R/Q + C173G/R + R207N/L + E328N/L/T/S | 2 |
| M63R/Q + C173G/R + R207 N/L + E327N/L/T/S | 11 |
| M63R/Q + C173G/R + R207N/L + E327N/L/T/S | 13 |
| L62R/Q + C172G/R + R206N/L + G323N/L/T/S | 15 |
| M63R/Q + C173G/R + R207N/L + E334N/L/T/S | 17 |
| M63R/Q + C173G/R + R207N/L + E327N/L/T/S | 19 |
| R64Q/G + C173G/R + R208N/L + E334N/L/T/S | 21 |
| M73R/Q + C178G/R + R207N/L + E328N/L/T/S | 23 |
| M64R/Q + C174G/R + R208N/L + E329N/L/T/S | 25 |
| M61R/Q + C171G/R + R205N/L + E326N/L/T/S | 27 |
| M63R/Q/G + C173G/R + R207N/L + E331N/L/T/S | 29 |
| L63R/Q + C173G/R + R207N/L + E328N/L/T/S | 31 |
| M63R/Q + C182G/R + R216N/L + E341N/L/T/S | 33 |
| M66R/Q + C176G/R + R210N/L + E331N/L/T/S | 35 |

Advantageously, the substitution is selected from CzzzG/R/P/A/V/S/N/Q/D, where Czzz represents an amino acid residue number functionally equivalent to C173 of SEQ ID NO:2 in SEQ ID NOs:11, 13, 15, 17, 19, 21, 23, 25, 27, 29, 31, 33 and 35, respectively, and such as from CzzzG/R, where Czzz represents an amino acid residue number functionally equivalent to C173 of SEQ ID NO: 2 in SEQ ID NOs:11, 13, 15, 17, 19, 21, 23, 25, 27, 29, 31, 33 and 35, respectively.

In a particular embodiment, the variant further comprises at least one amino acid substitution at position corresponding to functionally equivalent residues of residues selected from M63, R207, R324 and E327, of SEQ ID NO: 11.

According to the invention, all variants of TdT as disclosed above are able to both synthesize a nucleic acid fragment without template and incorporate a modified nucleotide into the nucleic acid fragment. Advantageously, said variants have an increased ability to incorporate a modified nucleotide, such as a 3'O-modified nucleotide, into a nucleic acid fragment as compared to aTdT of SEQ ID NOs:2, 11, 13, 15, 17, 19, 21, 23, 25, 27, 29, 31, 33 and 35.

In some of the embodiments described above, the efficiency of a variant TdT in incorporating a 3'O-modified nucleoside triphosphate is at least 110 percent that of a wild type TdT of sequence SEQ ID NO:2, 11, 13, 15, 17, 19, 21, 23, 25, 27, 29, 31, 33 and 35 in other embodiments, the efficiency of a variant TdT in incorporating a 3'O-modified nucleoside triphosphate is at least 150 percent that of a wild type TdT of sequence SEQ ID NOs:2, 11, 13, 15, 17, 19, 21, 23, 25, 27, 29, 31, 33 and 35; in other embodiments, the efficiency of a variant TdT in incorporating a 3'O-modified nucleoside triphosphate is at least 200 percent that of a wild type TdT of sequence SEQ ID NOs:2, 11, 13, 15, 17, 19, 21, 23, 25, 27, 29, 31, 33 and 35.

The present invention further provides a variant of TdT having the amino acid sequence as set forth in SEQ ID NO:2 or functionally equivalent sequence, with at least one substitution or combination of substitutions as listed in Table 5 or Table 6. The variants of the invention comprise at least the amino acid substitutions listed in the left column and called "Variable Mutations", or functionally equivalent residues, and optionally one or both combination of substitutions listed in the right column and called "Optional Constant Mutations", or functionally equivalent sequence.

TABLE 5

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS1 | M63R + L131P + C173R + R207L + D250V + R325P + E328L | L52F + A108V + R354K and/or G284L/S + H287D + E289A |
| DS2 | M63R + L131P + C173R + R207L + D250V + R325P + E328N | L52F + A108V + R354K and/or G284L/S + H287D + E289A |
| DS3 | M63R + L131P + C173R + R207L + D250V + R325P | L52F + A108V + R354K and/or G284L/S + H287D + E289A |
| DS4 | M63R + L131P + C173R + R207L + D250V + R325A + E328L | L52F + A108V + R354K and/or G284L/S + H287D + E289A |
| DS5 | M63R + L131P + C173R + R207L + D250V + R325A + E328N | L52F + A108V + R354K and/or G284L/S + H287D + E289A |
| DS6 | M63R + L131P + C173R + R207L + D250V + R325A | L52F + A108V + R354K and/or G284L/S + H287D + E289A |
| DS7 | M63R + L131P + C173R + R207L + D250V + E328L | L52F + A108V + R354K and/or G284L/S + H287D + E289A |
| DS8 | M63R + L131P + C173R + R207L + D250V + E328N | L52F + A108V + R354K and/or G284L/S + H287D + E289A |
| DS9 | M63R + L131P + C173R + R207L + D250V | L52F + A108V + R354K and/or G284L/S + H287D + E289A |
| DS10 | M63R + L131P + C173R + R207L + R325P + E328L | L52F + A108V + R354K and/or G284L/S + H287D + E289A |
| DS11 | M63R + L131P + C173R + R207L + R325P + E328N | L52F + A108V + R354K and/or G284L/S + H287D + E289A |
| DS12 | M63R + L131P + C173R + R207L + R325P | L52F + A108V + R354K and/or G284L/S + H287D + E289A |
| DS13 | M63R + L131P + C173R + R207L + R325A + E328L | L52F + A108V + R354K and/or G284L/S + H287D + E289A |
| DS14 | M63R + L131P + C173R + R207L + R325A + E328N | L52F + A108V + R354K and/or G284L/S + H287D + E289A |
| DS15 | M63R + L131P + C173R + R207L + R325A | L52F + A108V + R354K and/or G284L/S + H287D + E289A |
| DS16 | M63R + L131P + C173R + R207L + E328L | L52F + A108V + R354K and/or G284L/S + H287D + E289A |
| DS17 | M63R + L131P + C173R + R207L + E328N | L52F + A108V + R354K and/or G284L/S + H287D + E289A |
| DS18 | M63R + L131P + C173R + R207L | L52F + A108V + R354K and/or G284L/S + H287D + E289A |
| DS19 | M63R + L131P + C173R + R207N + D250V + R325P + E328L | L52F + A108V + R354K and/or G284L/S + H287D + E289A |
| DS20 | M63R + L131P + C173R + R207N + D250V + R325P + E328N | L52F + A108V + R354K and/or G284L/S + H287D + E289A |
| DS21 | M63R + L131P + C173R TABLE 5-continued Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS37 | M63R + L131P + C173R + D250V + R325P + E328L | L52F + A108V + R354K and/or G284L/S + H287D + E289A |
| DS38 | M63R + L131P + C173R + D250V + R325P + E328N | L52F + A108V + R354K and/or G284L/S + H287D + E289A |
| DS39 | M63R + L131P + C173R + D250V + R325P | L52F + A108V + R354K and/or G284L/S + H287D + E289A |
| DS40 | M63R + L131P + C173R + D250V + R325A + E328L | L52F + A108V + R354K and/or G284L/S + H287D + E289A |
| DS41 | M63R + L131P + C173R + D250V + R325A + E328N | L52F + A108V + R354K and/or G284L/S + H287D + E289A |
| DS42 | M63R + L131P + C173R + D250V + R325A | L52F + A108V + R354K and/or G284L/S + H287D + E289A |
| DS43 | M63R + L131P + C173R + D250V + E328L | L52F + A108V + R354K and/or G284L/S + H287D + E289A |
| DS44 | M63R + L131P + C173R + D250V + E328N | L52F + A108V + R354K and/or G284L/S + H287D + E289A |
| DS45 | M63R + L131P + C173R + D250V | L52F + A108V + R354K and/or G284L/S + H287D + E289A |
| DS46 | M63R + L131P + C173R + R325P + E328L | L52F + A108V + R354K and/or G284L/S + H287D + E289A |
| DS47 | M63R + L131P + C173R + R325P + E328N | L52F + A108V + R354K and/or G284L/S + H287D + E289A |
| DS48 | M63R + L131P + C173R + R325P | L52F + A108V + R354K and/or G284L/S + H287D + E289A |
| DS49 | M63R + L131P + C173R + R325A + E328L | L52F + A108V + R354K and/or G284L/S + H287D + E289A |
| DS50 | M63R + L131P + C173R + R325A + E328N | L52F + A108V + R354K and/or G284L/S + H287D + E289A |
| DS51 | M63R + L131P + C173R + R325A | L52F + A108V + R354K and/or G284L/S + H287D + E289A |
| DS52 | M63R + L131P + C173R + E328L | L52F + A108V + R354K and/or G284L/S + H287D + E289A |
| DS53 | M63R + L131P + C173R + E328N | L52F + A108V + R354K and/or G284L/S + H287D + E289A |
| DS54 | M63R + L131P + C173R | L52F + A108V + R354K and/or G284L/S + H287D + E289A |
| DS55 | M63R + L131P + C173G + R207L + D250V + R325P + E328L | L52F + A108V + R354K and/or G284L/S + H287D + E289A |
| DS56 | M63R + L131P + C173G + R207L + D250V + R325P + E328N | L52F + A108V + R354K and/or G284L/S + H287D + E289A |
| DS57 | M63R + L131P + C173G + R207L + D250V + R325P | L52F + A108V + R354K and/or G284L/S + H287D + E289A |
| DS58 | M63R + L131P + C173G + R207L + D250V + R325A + E328L | L52F + A108V + R354K and/or G284L/S + H287D + E289A |
| DS59 | M63R + L131P + C173G + R207L + D250V + R325A + E328N | L52F + A108V + R354K and/or G284L/S + H287D + E289A |
| DS60 | M63R + L131P + C173G + R207L + D250V + R325A | L52F + A108V + R354K and/or G284L/S + H287D + E289A |
| DS61 | M63R + L131P + C173G + R207L + D250V + E328L | L52F + A108V + R354K and/or G284L/S + H287D + E289A |
| DS62 | M63R + L131P + C173G + R207L + D250V + E328N | L52F + A108V + R354K and/or G284L/S + H287D + E289A |
| DS63 | M63R + L131P + C173G + R207L + D250V | L52F + A108V + R354K and/or G284L/S + H287D + E289A |
| DS64 | M63R + L131P + C173G + R207L + R325P + E328L | L52F + A108V + R354K and/or G284L/S + H287D + E289A |
| DS65 | M63R + L131P + C173G + R207L + R325P + E328N | L52F + A108V + R354K and/or G284L/S + H287D + E289A |
| DS66 | M63R + L131P + C173G + R207L + R325P | L52F + A108V + R354K and/or G284L/S + H287D + E289A |
| DS67 | M63R + L131P + C173G + R207L + R325A + E328L | L52F + A108V + R354K and/or G284L/S + H287D + E289A |
| DS68 | M63R + L131P + C173G + R207L + R325A + E328N | L52F + A108V + R354K and/or G284L/S + H287D + E289A |
| DS69 | M63R + L131P + C173G + R207L + R325A | L52F + A108V + R354K and/or G284L/S + H287D + E289A |
| DS70 | M63R + L131P + C173G + R207L + E328L | L52F + A108V + R354K and/or G284L/S + H287D + E289A |
| DS71 | M63R + L131P + C173G + R207L + E328N | L52F + A108V + R354K and/or G284L/S + H287D + E289A |
| DS72 | M63R + L131P + C173G + R207L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
| --- | --- | --- |
| DS73 | M63R + L131P + C173G + R207N + D250V + R325P + E328L | L52F + A108V + R354K and/or G284L/S + H287D + E289A |
| DS74 | M63R + L131P + C173G + R207N + D250V + R325P + E328N | L52F + A108V + R354K and/or G284L/S + H287D + E289A |
| DS75 | M63R + L131P + C173G + R207N + D250V + R325P | L52F + A108V + R354K and/or G284L/S + H287D + E289A |
| DS76 | M63R + L131P + C173G + R207N + D250V + R325A + E328L | L52F + A108V + R354K and/or G284L/S + H287D + E289A |
| DS77 | M63R + L131P + C173G + R207N + D250V + R325A + E328N | L52F + A108V + R354K and/or G284L/S + H287D + E289A |
| DS78 | M63R + L131P + C173G + R207N + D250V + R325A | L52F + A108V + R354K and/or G284L/S + H287D + E289A |
| DS79 | M63R + L131P + C173G + R207N + D250V + E328L | L52F + A108V + R354K and/or G284L/S + H287D + E289A |
| DS80 | M63R + L131P + C173G + R207N + D250V + E328N | L52F + A108V + R354K and/or G284L/S + H287D + E289A |
| DS81 | M63R + L131P + C173G + R207N + D250V | L52F + A108V + R354K and/or G284L/S + H287D + E289A |
| DS82 | M63R + L131P + C173G + R207N + R325P + E328L | L52F + A108V + R354K and/or G284L/S + H287D + E289A |
| DS83 | M63R + L131P + C173G + R207N + R325P + E328N | L52F + A108V + R354K and/or G284L/S + H287D + E289A |
| DS84 | M63R + L131P + C173G + R207N + R325P | L52F + A108V + R354K and/or G284L/S + H287D + E289A |
| DS85 | M63R + L131P + C173G + R207N + R325A + E328L | L52F + A108V + R354K and/or G284L/S + H287D + E289A |
| DS86 | M63R + L131P + C173G + R207N + R325A + E328N | L52F + A108V + R354K and/or G284L/S + H287D + E289A |
| DS87 | M63R + L131P + C173G + R207N + R325A | L52F + A108V + R354K and/or G284L/S + H287D + E289A |
| DS88 | M63R + L131P + C173G + R207N + E328L | L52F + A108V + R354K and/or G284L/S + H287D + E289A |
| DS89 | M63R + L131P + C173G + R207N + E328N | L52F + A108V + R354K and/or G284L/S + H287D + E289A |
| DS90 | M63R + L131P + C173G + R207N | L52F + A108V + R354K and/or G284L/S + H287D + E289A |
| DS91 | M63R + L131P + C173G + D250V + R325P + E328L | L52F + A108V + R354K and/or G284L/S + H287D + E289A |
| DS92 | M63R + L131P + C173G + D250V + R325P + E328N | L52F + A108V + R354K and/or G284L/S + H287D + E289A |
| DS93 | M63R + L131P + C173G + D250V + R325P | L52F + A108V + R354K and/or G284L/S + H287D + E289A |
| DS94 | M63R + L131P + C173G + D250V + R325A + E328L | L52F + A108V + R354K and/or G284L/S + H287D + E289A |
| DS95 | M63R + L131P + C173G + D250V + R325A + E328N | L52F + A108V + R354K and/or G284L/S + H287D + E289A |
| DS96 | M63R + L131P + C173G + D250V + R325A | L52F + A108V + R354K and/or G284L/S + H287D + E289A |
| DS97 | M63R + L131P + C173G + D250V + E328L | L52F + A108V + R354K and/or G284L/S + H287D + E289A |
| DS98 | M63R + L131P + C173G + D250V + E328N | L52F + A108V + R354K and/or G284L/S + H287D + E289A |
| DS99 | M63R + L131P + C173G + D250V | L52F + A108V + R354K and/or G284L/S + H287D + E289A |
| DS100 | M63R + L131P + C173G + R325P + E328L | L52F + A108V + R354K and/or G284L/S + H287D + E289A |
| DS101 | M63R + L131P + C173G + R325P + E328N | L52F + A108V + R354K and/or G284L/S + H287D + E289A |
| DS102 | M63R + L131P + C173G + R325P | L52F + A108V + R354K and/or G284L/S + H287D + E289A |
| DS103 | M63R + L131P + C173G + R325A + E328L | L52F + A108V + R354K and/or G284L/S + H287D + E289A |
| DS104 | M63R + L131P + C173G + R325A + E328N | L52F + A108V + R354K and/or G284L/S + H287D + E289A |
| DS105 | M63R + L131P + C173G + R325A | L52F + A108V + R354K and/or G284L/S + H287D + E289A |
| DS106 | M63R + L131P + C173G + E328L | L52F + A108V + R354K and/or G284L/S + H287D + E289A |
| DS107 | M63R + L131P + C173G + E328N | L52F + A108V + R354K and/or G284L/S + H287D + E289A |
| DS108 | M63R + L131P + C173G | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS163 | M63R + C173R + R207L + D250V + R325P + E328L | L52F + A108V + R354K and/or G284L/S + H287D + E289A |
| DS164 | M63R + C173R + R207L + D250V + R325P + E328N | L52F + A108V + R354K and/or G284L/S + H287D + E289A |
| DS165 | M63R + C173R + R207L + D250V + R325P | L52F + A108V + R354K and/or G284L/S + H287D + E289A |
| DS166 | M63R + C173R + R207L + D250V + R325A + E328L | L52F + A108V + R354K and/or G284L/S + H287D + E289A |
| DS167 | M63R + C173R + R207L + D250V + R325A + E328N | L52F + A108V + R354K and/or G284L/S + H287D + E289A |
| DS168 | M63R + C173R + R207L + D250V + R325A | L52F + A108V + R354K and/or G284L/S + H287D + E289A |
| DS169 | M63R + C173R + R207L + D250V + E328L | L52F + A108V + R354K and/or G284L/S + H287D + E289A |
| DS170 | M63R + C173R + R207L + D250V + E328N | L52F + A108V + R354K and/or G284L/S + H287D + E289A |
| DS171 | M63R + C173R + R207L + D250V | L52F + A108V + R354K and/or G284L/S + H287D + E289A |
| DS172 | M63R + C173R + R207L + R325P + E328L | L52F + A108V + R354K and/or G284L/S + H287D + E289A |
| DS173 | M63R + C173R + R207L + R325P + E328N | L52F + A108V + R354K and/or G284L/S + H287D + E289A |
| DS174 | M63R + C173R + R207L + R325P | L52F + A108V + R354K and/or G284L/S + H287D + E289A |
| DS175 | M63R + C173R + R207L + R325A + E328L | L52F + A108V + R354K and/or G284L/S + H287D + E289A |
| DS176 | M63R + C173R + R207L + R325A + E328N | L52F + A108V + R354K and/or G284L/S + H287D + E289A |
| DS177 | M63R + C173R + R207L + R325A | L52F + A108V + R354K and/or G284L/S + H287D + E289A |
| DS178 | M63R + C173R + R207L + E328L | L52F + A108V + R354K and/or G284L/S + H287D + E289A |
| DS179 | M63R + C173R + R207L + E328N | L52F + A108V + R354K and/or G284L/S + H287D + E289A |
| DS180 | M63R + C173R + R207L | L52F + A108V + R354K and/or G284L/S + H287D + E289A |
| DS52 | M63R + C173R + R207N + D250V + R325P + E328L | L52F + A108V + R354K and/or G284L/S + H287D + E289A |
| DS182 | M63R + C173R + R207N + D250V + R325P + E328N | L52F + A108V + R354K and/or G284L/S + H287D + E289A |
| DS183 | M63R + C173R + R207N + D250V + R325P | L52F + A108V + R354K and/or G284L/S + H287D + E289A |
| DS184 | M63R + C173R + R207N + D250V + R325A + E328L | L52F + A108V + R354K and/or G284L/S + H287D + E289A |
| DS185 | M63R + C173R + R207N + D250V + R325A + E328N | L52F + A108V + R354K and/or G284L/S + H287D + E289A |
| DS186 | M63R + C173R + R207N + D250V + R325A | L52F + A108V + R354K and/or G284L/S + H287D + E289A |
| DS187 | M63R + C173R + R207N + D250V + E328L | L52F + A108V + R354K and/or G284L/S + H287D + E289A |
| DS188 | M63R + C173R + R207N + D250V + E328N | L52F + A108V + R354K and/or G284L/S + H287D + E289A |
| DS189 | M63R + C173R + R207N + D250V | L52F + A108V + R354K and/or G284L/S + H287D + E289A |
| DS190 | M63R + C173R + R207N + R325P + E328L | L52F + A108V + R354K and/or G284L/S + H287D + E289A |
| DS191 | M63R + C173R + R207N + R325P + E328N | L52F + A108V + R354K and/or G284L/S + H287D + E289A |
| DS63 | M63R + C173R + R207N + R325P | L52F + A108V + R354K and/or G284L/S + H287D + E289A |
| DS193 | M63R + C173R + R207N + R325A + E328L | L52F + A108V + R354K and/or G284L/S + H287D + E289A |
| DS194 | M63R + C173R + R207N + R325A + E328N | L52F + A108V + R354K and/or G284L/S + H287D + E289A |
| DS195 | M63R + C173R + R207N + R325A | L52F + A108V + R354K and/or G284L/S + H287D + E289A |
| DS196 | M63R + C173R + R207N + E328L | L52F + A108V + R354K and/or G284L/S + H287D + E289A |
| DS197 | M63R + C173R + R207N + E328N | L52F + A108V + R354K and/or G284L/S + H287D + E289A |
| DS198 | M63R + C173R + R207N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS199 | M63R + C173R + D250V + R325P + E328L | L52F + A108V + R354K and/or G284L/S + H287D + E289A |
| DS200 | M63R + C173R + D250V + R325P + E328N | L52F + A108V + R354K and/or G284L/S + H287D + E289A |
| DS201 | M63R + C173R + D250V + R325P | L52F + A108V + R354K and/or G284L/S + H287D + E289A |
| DS202 | M63R + C173R + D250V + R325A + E328L | L52F + A108V + R354K and/or G284L/S + H287D + E289A |
| DS203 | M63R + C173R + D250V + R325A + E328N | L52F + A108V + R354K and/or G284L/S + H287D + E289A |
| DS204 | M63R + C173R + D250V + R325A | L52F + A108V + R354K and/or G284L/S + H287D + E289A |
| DS205 | M63R + C173R + D250V + E328L | L52F + A108V + R354K and/or G284L/S + H287D + E289A |
| DS206 | M63R + C173R + D250V + E328N | L52F + A108V + R354K and/or G284L/S + H287D + E289A |
| DS207 | M63R + C173R + D250V | L52F + A108V + R354K and/or G284L/S + H287D + E289A |
| DS208 | M63R + C173R + R325P + E328L | L52F + A108V + R354K and/or G284L/S + H287D + E289A |
| DS209 | M63R + C173R + R325P + E328N | L52F + A108V + R354K and/or G284L/S + H287D + E289A |
| DS210 | M63R + C173R + R325P | L52F + A108V + R354K and/or G284L/S + H287D + E289A |
| DS211 | M63R + C173R + R325A + E328L | L52F + A108V + R354K and/or G284L/S + H287D + E289A |
| DS212 | M63R + C173R + R325A + E328N | L52F + A108V + R354K and/or G284L/S + H287D + E289A |
| DS213 | M63R + C173R + R325A | L52F + A108V + R354K and/or G284L/S + H287D + E289A |
| DS214 | M63R + C173R + E328L | L52F + A108V + R354K and/or G284L/S + H287D + E289A |
| DS215 | M63R + C173R + E328N | L52F + A108V + R354K and/or G284L/S + H287D + E289A |
| DS216 | M63R + C173R | L52F + A108V + R354K and/or G284L/S + H287D + E289A |
| DS217 | M63R + C173G + R207L + D250V + R325P + E328L | L52F + A108V + R354K and/or G284L/S + H287D + E289A |
| DS218 | M63R + C173G + R207L + D250V + R325P + E328N | L52F + A108V + R354K and/or G284L/S + H287D + E289A |
| DS219 | M63R + C173G + R207L + D250V + R325P | L52F + A108V + R354K and/or G284L/S + H287D + E289A |
| DS220 | M63R + C173G + R207L + D250V + R325A + E328L | L52F + A108V + R354K and/or G284L/S + H287D + E289A |
| DS221 | M63R + C173G + R207L + D250V + R325A + E328N | L52F + A108V + R354K and/or G284L/S + H287D + E289A |
| DS222 | M63R + C173G + R207L + D250V + R325A | L52F + A108V + R354K and/or G284L/S + H287D + E289A |
| DS223 | M63R + C173G + R207L + D250V + E328L | L52F + A108V + R354K and/or G284L/S + H287D + E289A |
| DS224 | M63R + C173G + R207L + D250V + E328N | L52F + A108V + R354K and/or G284L/S + H287D + E289A |
| DS225 | M63R + C173G + R207L + D250V | L52F + A108V + R354K and/or G284L/S + H287D + E289A |
| DS226 | M63R + C173G + R207L + R325P + E328L | L52F + A108V + R354K and/or G284L/S + H287D + E289A |
| DS227 | M63R + C173G + R207L + R325P + E328N | L52F + A108V + R354K and/or G284L/S + H287D + E289A |
| DS228 | M63R + C173G + R207L + R325P | L52F + A108V + R354K and/or G284L/S + H287D + E289A |
| DS229 | M63R + C173G + R207L + R325A + E328L | L52F + A108V + R354K and/or G284L/S + H287D + E289A |
| DS230 | M63R + C173G + R207L + R325A + E328N | L52F + A108V + R354K and/or G284L/S + H287D + E289A |
| DS231 | M63R + C173G + R207L + R325A | L52F + A108V + R354K and/or G284L/S + H287D + E289A |
| DS232 | M63R + C173G + R207L + E328L | L52F + A108V + R354K and/or G284L/S + H287D + E289A |
| DS233 | M63R + C173G + R207L + E328N | L52F + A108V + R354K and/or G284L/S + H287D + E289A |
| DS234 | M63R + C173G + R207L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
| --- | --- | --- |
| DS235 | M63R + C173G + R207N + D250V + R325P + E328L | L52F + A108V + R354K and/or G284L/S + H287D + E289A |
| DS236 | M63R + C173G + R207N + D250V + R325P + E328N | L52F + A108V + R354K and/or G284L/S + H287D + E289A |
| DS108 | M63R + C173G + R207N + D250V + R325P | L52F + A108V + R354K and/or G284L/S + H287D + E289A |
| DS238 | M63R + C173G + R207N + D250V + R325A + E328L | L52F + A108V + R354K and/or G284L/S + H287D + E289A |
| DS239 | M63R + C173G + R207N + D250V + R325A + E328N | L52F + A108V + R354K and/or G284L/S + H287D + E289A |
| DS240 | M63R + C173G + R207N + D250V + R325A | L52F + A108V + R354K and/or G284L/S + H287D + E289A |
| DS241 | M63R + C173G + R207N + D250V + E328L | L52F + A108V + R354K and/or G284L/S + H287D + E289A |
| DS242 | M63R + C173G + R207N + D250V + E328N | L52F + A108V + R354K and/or G284L/S + H287D + E289A |
| DS243 | M63R + C173G + R207N + D250V | L52F + A108V + R354K and/or G284L/S + H287D + E289A |
| DS244 | M63R + C173G + R207N + R325P + E328L | L52F + A108V + R354K and/or G284L/S + H287D + E289A |
| DS245 | M63R + C173G + R207N + R325P + E328N | L52F + A108V + R354K and/or G284L/S + H287D + E289A |
| DS246 | M63R + C173G + R207N + R325P | L52F + A108V + R354K and/or G284L/S + H287D + E289A |
| DS247 | M63R + C173G + R207N + R325A + E328L | L52F + A108V + R354K and/or G284L/S + H287D + E289A |
| DS248 | M63R + C173G + R207N + R325A + E328N | L52F + A108V + R354K and/or G284L/S + H287D + E289A |
| DS249 | M63R + C173G + R207N + R325A | L52F + A108V + R354K and/or G284L/S + H287D + E289A |
| DS250 | M63R + C173G + R207N + E328L | L52F + A108V + R354K and/or G284L/S + H287D + E289A |
| DS251 | M63R + C173G + R207N + E328N | L52F + A108V + R354K and/or G284L/S + H287D + E289A |
| DS252 | M63R + C173G + R207N | L52F + A108V + R354K and/or G284L/S + H287D + E289A |
| DS253 | M63R + C173G + D250V + R325P + E328L | L52F + A108V + R354K and/or G284L/S + H287D + E289A |
| DS254 | M63R + C173G + D250V + R325P + E328N | L52F + A108V + R354K and/or G284L/S + H287D + E289A |
| DS255 | M63R + C173G + D250V + R325P | L52F + A108V + R354K and/or G284L/S + H287D + E289A |
| DS256 | M63R + C173G + D250V + R325A + E328L | L52F + A108V + R354K and/or G284L/S + H287D + E289A |
| DS257 | M63R + C173G + D250V + R325A + E328N | L52F + A108V + R354K and/or G284L/S + H287D + E289A |
| DS258 | M63R + C173G + D250V + R325A | L52F + A108V + R354K and/or G284L/S + H287D + E289A |
| DS259 | M63R + C173G + D250V + E328L | L52F + A108V + R354K and/or G284L/S + H287D + E289A |
| DS131 | M63R + C173G + D250V + E328N | L52F + A108V + R354K and/or G284L/S + H287D + E289A |
| DS261 | M63R + C173G + D250V | L52F + A108V + R354K and/or G284L/S + H287D + E289A |
| DS262 | M63R + C173G + R325P + E328L | L52F + A108V + R354K and/or G284L/S + H287D + E289A |
| DS263 | M63R + C173G + R325P + E328N | L52F + A108V + R354K and/or G284L/S + H287D + E289A |
| DS264 | M63R + C173G + R325P | L52F + A108V + R354K and/or G284L/S + H287D + E289A |
| DS265 | M63R + C173G + R325A + E328L | L52F + A108V + R354K and/or G284L/S + H287D + E289A |
| DS266 | M63R + C173G + R325A + E328N | L52F + A108V + R354K and/or G284L/S + H287D + E289A |
| DS267 | M63R + C173G + R325A | L52F + A108V + R354K and/or G284L/S + H287D + E289A |
| DS268 | M63R + C173G + E328L | L52F + A108V + R354K and/or G284L/S + H287D + E289A |
| DS269 | M63R + C173G + E328N | L52F + A108V + R354K and/or G284L/S + H287D + E289A |
| DS270 | M63R + C173G | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
| --- | --- | --- |
| DS325 | M63Q + L131P + C173R + R207L + D250V + R325P + E328L | L52F + A108V + R354K and/or G284L/S + H287D + E289A |
| DS326 | M63Q + L131P + C173R + R207L + D250V + R325P + E328N | L52F + A108V + R354K and/or G284L/S + H287D + E289A |
| DS327 | M63Q + L131P + C173R + R207L + D250V + R325P | L52F + A108V + R354K and/or G284L/S + H287D + E289A |
| DS328 | M63Q + L131P + C173R + R207L + D250V + R325A + E328L | L52F + A108V + R354K and/or G284L/S + H287D + E289A |
| DS329 | M63Q + L131P + C173R + R207L + D250V + R325A + E328N | L52F + A108V + R354K and/or G284L/S + H287D + E289A |
| DS330 | M63Q + L131P + C173R + R207L + D250V + R325A | L52F + A108V + R354K and/or G284L/S + H287D + E289A |
| DS331 | M63Q + L131P + C173R + R207L + D250V + E328L | L52F + A108V + R354K and/or G284L/S + H287D + E289A |
| DS332 | M63Q + L131P + C173R + R207L + D250V + E328N | L52F + A108V + R354K and/or G284L/S + H287D + E289A |
| DS333 | M63Q + L131P + C173R + R207L + D250V | L52F + A108V + R354K and/or G284L/S + H287D + E289A |
| DS334 | M63Q + L131P + C173R + R207L + R325P + E328L | L52F + A108V + R354K and/or G284L/S + H287D + E289A |
| DS335 | M63Q + L131P + C173R + R207L + R325P + E328N | L52F + A108V + R354K and/or G284L/S + H287D + E289A |
| DS207 | M63Q + L131P + C173R + R207L + R325P | L52F + A108V + R354K and/or G284L/S + H287D + E289A |
| DS337 | M63Q + L131P + C173R + R207L + R325A + E328L | L52F + A108V + R354K and/or G284L/S + H287D + E289A |
| DS338 | M63Q + L131P + C173R + R207L + R325A + E328N | L52F + A108V + R354K and/or G284L/S + H287D + E289A |
| DS339 | M63Q + L131P + C173R + R207L + R325A | L52F + A108V + R354K and/or G284L/S + H287D + E289A |
| DS340 | M63Q + L131P + C173R + R207L + E328L | L52F + A108V + R354K and/or G284L/S + H287D + E289A |
| DS341 | M63Q + L131P + C173R + R207L + E328N | L52F + A108V + R354K and/or G284L/S + H287D + E289A |
| DS342 | M63Q + L131P + C173R + R207L | L52F + A108V + R354K and/or G284L/S + H287D + E289A |
| DS343 | M63Q + L131P + C173R + R207N + D250V + R325P + E328L | L52F + A108V + R354K and/or G284L/S + H287D + E289A |
| DS344 | M63Q + L131P + C173R + R207N + D250V + R325P + E328N | L52F + A108V + R354K and/or G284L/S + H287D + E289A |
| DS345 | M63Q + L131P + C173R + R207N + D250V + R325P | L52F + A108V + R354K and/or G284L/S + H287D + E289A |
| DS346 | M63Q + L131P + C173R + R207N + D250V + R325A + E328L | L52F + A108V + R354K and/or G284L/S + H287D + E289A |
| DS347 | M63Q + L131P + C173R + R207N + D250V + R325A + E328N | L52F + A108V + R354K and/or G284L/S + H287D + E289A |
| DS348 | M63Q + L131P + C173R + R207N + D250V + R325A | L52F + A108V + R354K and/or G284L/S + H287D + E289A |
| DS349 | M63Q + L131P + C173R + R207N + D250V + E328L | L52F + A108V + R354K and/or G284L/S + H287D + E289A |
| DS350 | M63Q + L131P + C173R + R207N + D250V + E328N | L52F + A108V + R354K and/or G284L/S + H287D + E289A |
| DS351 | M63Q + L131P + C173R + R207N + D250V | L52F + A108V + R354K and/or G284L/S + H287D + E289A |
| DS352 | M63Q + L131P + C173R + R207N + R325P + E328L | L52F + A108V + R354K and/or G284L/S + H287D + E289A |
| DS353 | M63Q + L131P + C173R + R207N + R325P + E328N | L52F + A108V + R354K and/or G284L/S + H287D + E289A |
| DS354 | M63Q + L131P + C173R + R207N + R325P | L52F + A108V + R354K and/or G284L/S + H287D + E289A |
| DS355 | M63Q + L131P + C173R + R207N + R325A + E328L | L52F + A108V + R354K and/or G284L/S + H287D + E289A |
| DS356 | M63Q + L131P + C173R + R207N + R325A + E328N | L52F + A108V + R354K and/or G284L/S + H287D + E289A |
| DS357 | M63Q + L131P + C173R + R207N + R325A | L52F + A108V + R354K and/or G284L/S + H287D + E289A |
| DS358 | M63Q + L131P + C173R + R207N + E328L | L52F + A108V + R354K and/or G284L/S + H287D + E289A |
| DS359 | M63Q + L131P + C173R + R207N + E328N | L52F + A108V + R354K and/or G284L/S + H287D + E289A |
| DS360 | M63Q + L131P + C173R + R207N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS361 | M63Q + L131P + C173R + D250V + R325P + E328L | L52F + A108V + R354K and/or G284L/S + H287D + E289A |
| DS362 | M63Q + L131P + C173R + D250V + R325P + E328N | L52F + A108V + R354K and/or G284L/S + H287D + E289A |
| DS363 | M63Q + L131P + C173R + D250V + R325P | L52F + A108V + R354K and/or G284L/S + H287D + E289A |
| DS364 | M63Q + L131P + C173R + D250V + R325A + E328L | L52F + A108V + R354K and/or G284L/S + H287D + E289A |
| DS365 | M63Q + L131P + C173R + D250V + R325A + E328N | L52F + A108V + R354K and/or G284L/S + H287D + E289A |
| DS366 | M63Q + L131P + C173R + D250V + R325A | L52F + A108V + R354K and/or G284L/S + H287D + E289A |
| DS367 | M63Q + L131P + C173R + D250V + E328L | L52F + A108V + R354K and/or G284L/S + H287D + E289A |
| DS368 | M63Q + L131P + C173R + D250V + E328N | L52F + A108V + R354K and/or G284L/S + H287D + E289A |
| DS369 | M63Q + L131P + C173R + D250V | L52F + A108V + R354K and/or G284L/S + H287D + E289A |
| DS370 | M63Q + L131P + C173R + R325P + E328L | L52F + A108V + R354K and/or G284L/S + H287D + E289A |
| DS371 | M63Q + L131P + C173R + R325P + E328N | L52F + A108V + R354K and/or G284L/S + H287D + E289A |
| DS372 | M63Q + L131P + C173R + R325P | L52F + A108V + R354K and/or G284L/S + H287D + E289A |
| DS373 | M63Q + L131P + C173R + R325A + E328L | L52F + A108V + R354K and/or G284L/S + H287D + E289A |
| DS374 | M63Q + L131P + C173R + R325A + E328N | L52F + A108V + R354K and/or G284L/S + H287D + E289A |
| DS375 | M63Q + L131P + C173R + R325A | L52F + A108V + R354K and/or G284L/S + H287D + E289A |
| DS376 | M63Q + L131P + C173R + E328L | L52F + A108V + R354K and/or G284L/S + H287D + E289A |
| DS377 | M63Q + L131P + C173R + E328N | L52F + A108V + R354K and/or G284L/S + H287D + E289A |
| DS378 | M63Q + L131P + C173R | L52F + A108V + R354K and/or G284L/S + H287D + E289A |
| DS250 | M63Q + L131P + C173G + R207L + D250V + R325P + E328L | L52F + A108V + R354K and/or G284L/S + H287D + E289A |
| DS380 | M63Q + L131P + C173G + R207L + D250V + R325P + E328N | L52F + A108V + R354K and/or G284L/S + H287D + E289A |
| DS381 | M63Q + L131P + C173G + R207L + D250V + R325P | L52F + A108V + R354K and/or G284L/S + H287D + E289A |
| DS382 | M63Q + L131P + C173G + R207L + D250V + R325A + E328L | L52F + A108V + R354K and/or G284L/S + H287D + E289A |
| DS383 | M63Q + L131P + C173G + R207L + D250V + R325A + E328N | L52F + A108V + R354K and/or G284L/S + H287D + E289A |
| DS384 | M63Q + L131P + C173G + R207L + D250V + R325A | L52F + A108V + R354K and/or G284L/S + H287D + E289A |
| DS385 | M63Q + L131P + C173G + R207L + D250V + E328L | L52F + A108V + R354K and/or G284L/S + H287D + E289A |
| DS386 | M63Q + L131P + C173G + R207L + D250V + E328N | L52F + A108V + R354K and/or G284L/S + H287D + E289A |
| DS387 | M63Q + L131P + C173G + R207L + D250V | L52F + A108V + R354K and/or G284L/S + H287D + E289A |
| DS388 | M63Q + L131P + C173G + R207L + R325P + E328L | L52F + A108V + R354K and/or G284L/S + H287D + E289A |
| DS389 | M63Q + L131P + C173G + R207L + R325P + E328N | L52F + A108V + R354K and/or G284L/S + H287D + E289A |
| DS390 | M63Q + L131P + C173G + R207L + R325P | L52F + A108V + R354K and/or G284L/S + H287D + E289A |
| DS391 | M63Q + L131P + C173G + R207L + R325A + E328L | L52F + A108V + R354K and/or G284L/S + H287D + E289A |
| DS392 | M63Q + L131P + C173G + R207L + R325A + E328N | L52F + A108V + R354K and/or G284L/S + H287D + E289A |
| DS393 | M63Q + L131P + C173G + R207L + R325A | L52F + A108V + R354K and/or G284L/S + H287D + E289A |
| DS394 | M63Q + L131P + C173G + R207L + E328L | L52F + A108V + R354K and/or G284L/S + H287D + E289A |
| DS395 | M63Q + L131P + C173G + R207L + E328N | L52F + A108V + R354K and/or G284L/S + H287D + E289A |
| DS396 | M63Q + L131P + C173G + R207L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
| --- | --- | --- |
| DS397 | M63Q + L131P + C173G + R207N + D250V + R325P + E328L | L52F + A108V + R354K and/or G284L/S + H287D + E289A |
| DS398 | M63Q + L131P + C173G + R207N + D250V + R325P + E328N | L52F + A108V + R354K and/or G284L/S + H287D + E289A |
| DS399 | M63Q + L131P + C173G + R207N + D250V + R325P | L52F + A108V + R354K and/or G284L/S + H287D + E289A |
| DS400 | M63Q + L131P + C173G + R207N + D250V + R325A + E328L | L52F + A108V + R354K and/or G284L/S + H287D + E289A |
| DS401 | M63Q + L131P + C173G + R207N + D250V + R325A + E328N | L52F + A108V + R354K and/or G284L/S + H287D + E289A |
| DS402 | M63Q + L131P + C173G + R207N + D250V + R325A | L52F + A108V + R354K and/or G284L/S + H287D + E289A |
| DS403 | M63Q + L131P + C173G + R207N + D250V + E328L | L52F + A108V + R354K and/or G284L/S + H287D + E289A |
| DS404 | M63Q + L131P + C173G + R207N + D250V + E328N | L52F + A108V + R354K and/or G284L/S + H287D + E289A |
| DS405 | M63Q + L131P + C173G + R207N + D250V | L52F + A108V + R354K and/or G284L/S + H287D + E289A |
| DS406 | M63Q + L131P + C173G + R207N + R325P + E328L | L52F + A108V + R354K and/or G284L/S + H287D + E289A |
| DS407 | M63Q + L131P + C173G + R207N + R325P + E328N | L52F + A108V + R354K and/or G284L/S + H287D + E289A |
| DS408 | M63Q + L131P + C173G + R207N + R325P | L52F + A108V + R354K and/or G284L/S + H287D + E289A |
| DS409 | M63Q + L131P + C173G + R207N + R325A + E328L | L52F + A108V + R354K and/or G284L/S + H287D + E289A |
| DS410 | M63Q + L131P + C173G + R207N + R325A + E328N | L52F + A108V + R354K and/or G284L/S + H287D + E289A |
| DS411 | M63Q + L131P + C173G + R207N + R325A | L52F + A108V + R354K and/or G284L/S + H287D + E289A |
| DS412 | M63Q + L131P + C173G + R207N + E328L | L52F + A108V + R354K and/or G284L/S + H287D + E289A |
| DS284 | M63Q + L131P + C173G + R207N + E328N | L52F + A108V + R354K and/or G284L/S + H287D + E289A |
| DS414 | M63Q + L131P + C173G + R207N | L52F + A108V + R354K and/or G284L/S + H287D + E289A |
| DS415 | M63Q + L131P + C173G + D250V + R325P + E328L | L52F + A108V + R354K and/or G284L/S + H287D + E289A |
| DS287 | M63Q + L131P + C173G + D250V + R325P + E328N | L52F + A108V + R354K and/or G284L/S + H287D + E289A |
| DS417 | M63Q + L131P + C173G + D250V + R325P | L52F + A108V + R354K and/or G284L/S + H287D + E289A |
| DS289 | M63Q + L131P + C173G + D250V + R325A + E328L | L52F + A108V + R354K and/or G284L/S + H287D + E289A |
| DS419 | M63Q + L131P + C173G + D250V + R325A + E328N | L52F + A108V + R354K and/or G284L/S + H287D + E289A |
| DS420 | M63Q + L131P + C173G + D250V + R325A | L52F + A108V + R354K and/or G284L/S + H287D + E289A |
| DS421 | M63Q + L131P + C173G + D250V + E328L | L52F + A108V + R354K and/or G284L/S + H287D + E289A |
| DS422 | M63Q + L131P + C173G + D250V + E328N | L52F + A108V + R354K and/or G284L/S + H287D + E289A |
| DS423 | M63Q + L131P + C173G + D250V | L52F + A108V + R354K and/or G284L/S + H287D + E289A |
| DS424 | M63Q + L131P + C173G + R325P + E328L | L52F + A108V + R354K and/or G284L/S + H287D + E289A |
| DS425 | M63Q + L131P + C173G + R325P + E328N | L52F + A108V + R354K and/or G284L/S + H287D + E289A |
| DS426 | M63Q + L131P + C173G + R325P | L52F + A108V + R354K and/or G284L/S + H287D + E289A |
| DS427 | M63Q + L131P + C173G + R325A + E328L | L52F + A108V + R354K and/or G284L/S + H287D + E289A |
| DS428 | M63Q + L131P + C173G + R325A + E328N | L52F + A108V + R354K and/or G284L/S + H287D + E289A |
| DS429 | M63Q + L131P + C173G + R325A | L52F + A108V + R354K and/or G284L/S + H287D + E289A |
| DS430 | M63Q + L131P + C173G + E328L | L52F + A108V + R354K and/or G284L/S + H287D + E289A |
| DS431 | M63Q + L131P + C173G + E328N | L52F + A108V + R354K and/or G284L/S + H287D + E289A |
| DS432 | M63Q + L131P + C173G | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS487 | M63Q + C173R + R207L + D250V + R325P + E328L | L52F + A108V + R354K and/or G284L/S + H287D + E289A |
| DS488 | M63Q + C173R + R207L + D250V + R325P + E328N | L52F + A108V + R354K and/or G284L/S + H287D + E289A |
| DS489 | M63Q + C173R + R207L + D250V + R325P | L52F + A108V + R354K and/or G284L/S + H287D + E289A |
| DS490 | M63Q + C173R + R207L + D250V + R325A + E328L | L52F + A108V + R354K and/or G284L/S + H287D + E289A |
| DS491 | M63Q + C173R + R207L + D250V + R325A + E328N | L52F + A108V + R354K and/or G284L/S + H287D + E289A |
| DS492 | M63Q + C173R + R207L + D250V + R325A | L52F + A108V + R354K and/or G284L/S + H287D + E289A |
| DS493 | M63Q + C173R + R207L + D250V + E328L | L52F + A108V + R354K and/or G284L/S + H287D + E289A |
| DS494 | M63Q + C173R + R207L + D250V + E328N | L52F + A108V + R354K and/or G284L/S + H287D + E289A |
| DS495 | M63Q + C173R + R207L + D250V | L52F + A108V + R354K and/or G284L/S + H287D + E289A |
| DS496 | M63Q + C173R + R207L + R325P + E328L | L52F + A108V + R354K and/or G284L/S + H287D + E289A |
| DS497 | M63Q + C173R + R207L + R325P + E328N | L52F + A108V + R354K and/or G284L/S + H287D + E289A |
| DS498 | M63Q + C173R + R207L + R325P | L52F + A108V + R354K and/or G284L/S + H287D + E289A |
| DS499 | M63Q + C173R + R207L + R325A + E328L | L52F + A108V + R354K and/or G284L/S + H287D + E289A |
| DS500 | M63Q + C173R + R207L + R325A + E328N | L52F + A108V + R354K and/or G284L/S + H287D + E289A |
| DS501 | M63Q + C173R + R207L + R325A | L52F + A108V + R354K and/or G284L/S + H287D + E289A |
| DS502 | M63Q + C173R + R207L + E328L | L52F + A108V + R354K and/or G284L/S + H287D + E289A |
| DS503 | M63Q + C173R + R207L + E328N | L52F + A108V + R354K and/or G284L/S + H287D + E289A |
| DS504 | M63Q + C173R + R207L | L52F + A108V + R354K and/or G284L/S + H287D + E289A |
| DS505 | M63Q + C173R + R207N + D250V + R325P + E328L | L52F + A108V + R354K and/or G284L/S + H287D + E289A |
| DS506 | M63Q + C173R + R207N + D250V + R325P + E328N | L52F + A108V + R354K and/or G284L/S + H287D + E289A |
| DS507 | M63Q + C173R + R207N + D250V + R325P | L52F + A108V + R354K and/or G284L/S + H287D + E289A |
| DS508 | M63Q + C173R + R207N + D250V + R325A + E328L | L52F + A108V + R354K and/or G284L/S + H287D + E289A |
| DS509 | M63Q + C173R + R207N + D250V + R325A + E328N | L52F + A108V + R354K and/or G284L/S + H287D + E289A |
| DS510 | M63Q + C173R + R207N + D250V + R325A | L52F + A108V + R354K and/or G284L/S + H287D + E289A |
| DS511 | M63Q + C173R + R207N + D250V + E328L | L52F + A108V + R354K and/or G284L/S + H287D + E289A |
| DS512 | M63Q + C173R + R207N + D250V + E328N | L52F + A108V + R354K and/or G284L/S + H287D + E289A |
| DS513 | M63Q + C173R + R207N + D250V | L52F + A108V + R354K and/or G284L/S + H287D + E289A |
| DS514 | M63Q + C173R + R207N + R325P + E328L | L52F + A108V + R354K and/or G284L/S + H287D + E289A |
| DS515 | M63Q + C173R + R207N + R325P + E328N | L52F + A108V + R354K and/or G284L/S + H287D + E289A |
| DS516 | M63Q + C173R + R207N + R325P | L52F + A108V + R354K and/or G284L/S + H287D + E289A |
| DS517 | M63Q + C173R + R207N + R325A + E328L | L52F + A108V + R354K and/or G284L/S + H287D + E289A |
| DS518 | M63Q + C173R + R207N + R325A + E328N | L52F + A108V + R354K and/or G284L/S + H287D + E289A |
| DS519 | M63Q + C173R + R207N + R325A | L52F + A108V + R354K and/or G284L/S + H287D + E289A |
| DS520 | M63Q + C173R + R207N + E328L | L52F + A108V + R354K and/or G284L/S + H287D + E289A |
| DS521 | M63Q + C173R + R207N + E328N | L52F + A108V + R354K and/or G284L/S + H287D + E289A |
| DS522 | M63Q + C173R + R207N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS523 | M63Q + C173R + D250V + R325P + E328L | L52F + A108V + R354K and/or G284L/S + H287D + E289A |
| DS524 | M63Q + C173R + D250V + R325P + E328N | L52F + A108V + R354K and/or G284L/S + H287D + E289A |
| DS525 | M63Q + C173R + D250V + R325P | L52F + A108V + R354K and/or G284L/S + H287D + E289A |
| DS526 | M63Q + C173R + D250V + R325A + E328L | L52F + A108V + R354K and/or G284L/S + H287D + E289A |
| DS527 | M63Q + C173R + D250V + R325A + E328N | L52F + A108V + R354K and/or G284L/S + H287D + E289A |
| DS528 | M63Q + C173R + D250V + R325A | L52F + A108V + R354K and/or G284L/S + H287D + E289A |
| DS529 | M63Q + C173R + D250V + E328L | L52F + A108V + R354K and/or G284L/S + H287D + E289A |
| DS530 | M63Q + C173R + D250V + E328N | L52F + A108V + R354K and/or G284L/S + H287D + E289A |
| DS531 | M63Q + C173R + D250V | L52F + A108V + R354K and/or G284L/S + H287D + E289A |
| DS532 | M63Q + C173R + R325P + E328L | L52F + A108V + R354K and/or G284L/S + H287D + E289A |
| DS533 | M63Q + C173R + R325P + E328N | L52F + A108V + R354K and/or G284L/S + H287D + E289A |
| DS534 | M63Q + C173R + R325P | L52F + A108V + R354K and/or G284L/S + H287D + E289A |
| DS535 | M63Q + C173R + R325A + E328L | L52F + A108V + R354K and/or G284L/S + H287D + E289A |
| DS536 | M63Q + C173R + R325A + E328N | L52F + A108V + R354K and/or G284L/S + H287D + E289A |
| DS537 | M63Q + C173R + R325A | L52F + A108V + R354K and/or G284L/S + H287D + E289A |
| DS538 | M63Q + C173R + E328L | L52F + A108V + R354K and/or G284L/S + H287D + E289A |
| DS539 | M63Q + C173R + E328N | L52F + A108V + R354K and/or G284L/S + H287D + E289A |
| DS540 | M63Q + C173R | L52F + A108V + R354K and/or G284L/S + H287D + E289A |
| DS541 | M63Q + C173G + R207L + D250V + R325P + E328L | L52F + A108V + R354K and/or G284L/S + H287D + E289A |
| DS542 | M63Q + C173G + R207L + D250V + R325P + E328N | L52F + A108V + R354K and/or G284L/S + H287D + E289A |
| DS543 | M63Q + C173G + R207L + D250V + R325P | L52F + A108V + R354K and/or G284L/S + H287D + E289A |
| DS544 | M63Q + C173G + R207L + D250V + R325A + E328L | L52F + A108V + R354K and/or G284L/S + H287D + E289A |
| DS545 | M63Q + C173G + R207L + D250V + R325A + E328N | L52F + A108V + R354K and/or G284L/S + H287D + E289A |
| DS546 | M63Q + C173G + R207L + D250V + R325A | L52F + A108V + R354K and/or G284L/S + H287D + E289A |
| DS547 | M63Q + C173G + R207L + D250V + E328L | L52F + A108V + R354K and/or G284L/S + H287D + E289A |
| DS548 | M63Q + C173G + R207L + D250V + E328N | L52F + A108V + R354K and/or G284L/S + H287D + E289A |
| DS549 | M63Q + C173G + R207L + D250V | L52F + A108V + R354K and/or G284L/S + H287D + E289A |
| DS550 | M63Q + C173G + R207L + R325P + E328L | L52F + A108V + R354K and/or G284L/S + H287D + E289A |
| DS551 | M63Q + C173G + R207L + R325P + E328N | L52F + A108V + R354K and/or G284L/S + H287D + E289A |
| DS552 | M63Q + C173G + R207L + R325P | L52F + A108V + R354K and/or G284L/S + H287D + E289A |
| DS553 | M63Q + C173G + R207L + R325A + E328L | L52F + A108V + R354K and/or G284L/S + H287D + E289A |
| DS554 | M63Q + C173G + R207L + R325A + E328N | L52F + A108V + R354K and/or G284L/S + H287D + E289A |
| DS555 | M63Q + C173G + R207L + R325A | L52F + A108V + R354K and/or G284L/S + H287D + E289A |
| DS556 | M63Q + C173G + R207L + E328L | L52F + A108V + R354K and/or G284L/S + H287D + E289A |
| DS557 | M63Q + C173G + R207L + E328N | L52F + A108V + R354K and/or G284L/S + H287D + E289A |
| DS558 | M63Q + C173G + R207L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS559 | M63Q + C173G + R207N + D250V + R325P + E328L | L52F + A108V + R354K and/or G284L/S + H287D + E289A |
| DS560 | M63Q + C173G + R207N + D250V + R325P + E328N | L52F + A108V + R354K and/or G284L/S + H287D + E289A |
| DS561 | M63Q + C173G + R207N + D250V + R325P | L52F + A108V + R354K and/or G284L/S + H287D + E289A |
| DS562 | M63Q + C173G + R207N + D250V + R325A + E328L | L52F + A108V + R354K and/or G284L/S + H287D + E289A |
| DS563 | M63Q + C173G + R207N + D250V + R325A + E328N | L52F + A108V + R354K and/or G284L/S + H287D + E289A |
| DS564 | M63Q + C173G + R207N + D250V + R325A | L52F + A108V + R354K and/or G284L/S + H287D + E289A |
| DS565 | M63Q + C173G + R207N + D250V + E328L | L52F + A108V + R354K and/or G284L/S + H287D + E289A |
| DS566 | M63Q + C173G + R207N + D250V + E328N | L52F + A108V + R354K and/or G284L/S + H287D + E289A |
| DS567 | M63Q + C173G + R207N + D250V | L52F + A108V + R354K and/or G284L/S + H287D + E289A |
| DS568 | M63Q + C173G + R207N + R325P + E328L | L52F + A108V + R354K and/or G284L/S + H287D + E289A |
| DS569 | M63Q + C173G + R207N + R325P + E328N | L52F + A108V + R354K and/or G284L/S + H287D + E289A |
| DS570 | M63Q + C173G + R207N + R325P | L52F + A108V + R354K and/or G284L/S + H287D + E289A |
| DS571 | M63Q + C173G + R207N + R325A + E328L | L52F + A108V + R354K and/or G284L/S + H287D + E289A |
| DS572 | M63Q + C173G + R207N + R325A + E328N | L52F + A108V + R354K and/or G284L/S + H287D + E289A |
| DS573 | M63Q + C173G + R207N + R325A | L52F + A108V + R354K and/or G284L/S + H287D + E289A |
| DS574 | M63Q + C173G + R207N + E328L | L52F + A108V + R354K and/or G284L/S + H287D + E289A |
| DS575 | M63Q + C173G + R207N + E328N | L52F + A108V + R354K and/or G284L/S + H287D + E289A |
| DS576 | M63Q + C173G + R207N | L52F + A108V + R354K and/or G284L/S + H287D + E289A |
| DS577 | M63Q + C173G + D250V + R325P + E328L | L52F + A108V + R354K and/or G284L/S + H287D + E289A |
| DS578 | M63Q + C173G + D250V + R325P + E328N | L52F + A108V + R354K and/or G284L/S + H287D + E289A |
| DS579 | M63Q + C173G + D250V + R325P | L52F + A108V + R354K and/or G284L/S + H287D + E289A |
| DS580 | M63Q + C173G + D250V + R325A + E328L | L52F + A108V + R354K and/or G284L/S + H287D + E289A |
| DS581 | M63Q + C173G + D250V + R325A + E328N | L52F + A108V + R354K and/or G284L/S + H287D + E289A |
| DS582 | M63Q + C173G + D250V + R325A | L52F + A108V + R354K and/or G284L/S + H287D + E289A |
| DS583 | M63Q + C173G + D250V + E328L | L52F + A108V + R354K and/or G284L/S + H287D + E289A |
| DS584 | M63Q + C173G + D250V + E328N | L52F + A108V + R354K and/or G284L/S + H287D + E289A |
| DS585 | M63Q + C173G + D250V | L52F + A108V + R354K and/or G284L/S + H287D + E289A |
| DS586 | M63Q + C173G + R325P + E328L | L52F + A108V + R354K and/or G284L/S + H287D + E289A |
| DS587 | M63Q + C173G + R325P + E328N | L52F + A108V + R354K and/or G284L/S + H287D + E289A |
| DS588 | M63Q + C173G + R325P | L52F + A108V + R354K and/or G284L/S + H287D + E289A |
| DS589 | M63Q + C173G + R325A + E328L | L52F + A108V + R354K and/or G284L/S + H287D + E289A |
| DS590 | M63Q + C173G + R325A + E328N | L52F + A108V + R354K and/or G284L/S + H287D + E289A |
| DS591 | M63Q + C173G + R325A | L52F + A108V + R354K and/or G284L/S + H287D + E289A |
| DS592 | M63Q + C173G + E328L | L52F + A108V + R354K and/or G284L/S + H287D + E289A |
| DS593 | M63Q + C173G + E328N | L52F + A108V + R354K and/or G284L/S + H287D + E289A |
| DS594 | M63Q + C173G | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
| --- | --- | --- |
| DS649 | L131P + C173R + R207L + D250V + R325P + E328L | L52F + A108V + R354K and/or G284L/S + H287D + E289A |
| DS650 | L131P + C173R + R207L + D250V + R325P + E328N | L52F + A108V + R354K and/or G284L/S + H287D + E289A |
| DS651 | L131P + C173R + R207L + D250V + R325P | L52F + A108V + R354K and/or G284L/S + H287D + E289A |
| DS652 | L131P + C173R + R207L + D250V + R325A + E328L | L52F + A108V + R354K and/or G284L/S + H287D + E289A |
| DS653 | L131P + C173R + R207L + D250V + R325A + E328N | L52F + A108V + R354K and/or G284L/S + H287D + E289A |
| DS654 | L131P + C173R + R207L + D250V + R325A | L52F + A108V + R354K and/or G284L/S + H287D + E289A |
| DS655 | L131P + C173R + R207L + D250V + E328L | L52F + A108V + R354K and/or G284L/S + H287D + E289A |
| DS656 | L131P + C173R + R207L + D250V + E328N | L52F + A108V + R354K and/or G284L/S + H287D + E289A |
| DS657 | L131P + C173R + R207L + D250V | L52F + A108V + R354K and/or G284L/S + H287D + E289A |
| DS658 | L131P + C173R + R207L + R325P + E328L | L52F + A108V + R354K and/or G284L/S + H287D + E289A |
| DS659 | L131P + C173R + R207L + R325P + E328N | L52F + A108V + R354K and/or G284L/S + H287D + E289A |
| DS660 | L131P + C173R + R207L + R325P | L52F + A108V + R354K and/or G284L/S + H287D + E289A |
| DS661 | L131P + C173R + R207L + R325A + E328L | L52F + A108V + R354K and/or G284L/S + H287D + E289A |
| DS662 | L131P + C173R + R207L + R325A + E328N | L52F + A108V + R354K and/or G284L/S + H287D + E289A |
| DS663 | L131P + C173R + R207L + R325A | L52F + A108V + R354K and/or G284L/S + H287D + E289A |
| DS664 | L131P + C173R + R207L + E328L | L52F + A108V + R354K and/or G284L/S + H287D + E289A |
| DS665 | L131P + C173R + R207L + E328N | L52F + A108V + R354K and/or G284L/S + H287D + E289A |
| DS666 | L131P + C173R + R207L | L52F + A108V + R354K and/or G284L/S + H287D + E289A |
| DS667 | L131P + C173R + R207N + D250V + R325P + E328L | L52F + A108V + R354K and/or G284L/S + H287D + E289A |
| DS668 | L131P + C173R + R207N + D250V + R325P + E328N | L52F + A108V + R354K and/or G284L/S + H287D + E289A |
| DS669 | L131P + C173R + R207N + D250V + R325P | L52F + A108V + R354K and/or G284L/S + H287D + E289A |
| DS670 | L131P + C173R + R207N + D250V + R325A + E328L | L52F + A108V + R354K and/or G284L/S + H287D + E289A |
| DS671 | L131P + C173R + R207N + D250V + R325A + E328N | L52F + A108V + R354K and/or G284L/S + H287D + E289A |
| DS672 | L131P + C173R + R207N + D250V + R325A | L52F + A108V + R354K and/or G284L/S + H287D + E289A |
| DS673 | L131P + C173R + R207N + D250V + E328L | L52F + A108V + R354K and/or G284L/S + H287D + E289A |
| DS674 | L131P + C173R + R207N + D250V + E328N | L52F + A108V + R354K and/or G284L/S + H287D + E289A |
| DS675 | L131P + C173R + R207N + D250V | L52F + A108V + R354K and/or G284L/S + H287D + E289A |
| DS676 | L131P + C173R + R207N + R325P + E328L | L52F + A108V + R354K and/or G284L/S + H287D + E289A |
| DS677 | L131P + C173R + R207N + R325P + E328N | L52F + A108V + R354K and/or G284L/S + H287D + E289A |
| DS678 | L131P + C173R + R207N + R325P | L52F + A108V + R354K and/or G284L/S + H287D + E289A |
| DS679 | L131P + C173R + R207N + R325A + E328L | L52F + A108V + R354K and/or G284L/S + H287D + E289A |
| DS680 | L131P + C173R + R207N + R325A + E328N | L52F + A108V + R354K and/or G284L/S + H287D + E289A |
| DS681 | L131P + C173R + R207N + R325A | L52F + A108V + R354K and/or G284L/S + H287D + E289A |
| DS682 | L131P + C173R + R207N + E328L | L52F + A108V + R354K and/or G284L/S + H287D + E289A |
| DS683 | L131P + C173R + R207N + E328N | L52F + A108V + R354K and/or G284L/S + H287D + E289A |
| DS684 | L131P + C173R + R207N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
| --- | --- | --- |
| DS685 | L131P + C173R + D250V + R325P + E328L | L52F + A108V + R354K and/or G284L/S + H287D + E289A |
| DS686 | L131P + C173R + D250V + R325P + E328N | L52F + A108V + R354K and/or G284L/S + H287D + E289A |
| DS687 | L131P + C173R + D250V + R325P | L52F + A108V + R354K and/or G284L/S + H287D + E289A |
| DS688 | L131P + C173R + D250V + R325A + E328L | L52F + A108V + R354K and/or G284L/S + H287D + E289A |
| DS689 | L131P + C173R + D250V + R325A + E328N | L52F + A108V + R354K and/or G284L/S + H287D + E289A |
| DS690 | L131P + C173R + D250V + R325A | L52F + A108V + R354K and/or G284L/S + H287D + E289A |
| DS691 | L131P + C173R + D250V + E328L | L52F + A108V + R354K and/or G284L/S + H287D + E289A |
| DS692 | L131P + C173R + D250V + E328N | L52F + A108V + R354K and/or G284L/S + H287D + E289A |
| DS693 | L131P + C173R + D250V | L52F + A108V + R354K and/or G284L/S + H287D + E289A |
| DS694 | L131P + C173R + R325P + E328L | L52F + A108V + R354K and/or G284L/S + H287D + E289A |
| DS695 | L131P + C173R + R325P + E328N | L52F + A108V + R354K and/or G284L/S + H287D + E289A |
| DS696 | L131P + C173R + R325P | L52F + A108V + R354K and/or G284L/S + H287D + E289A |
| DS697 | L131P + C173R + R325A + E328L | L52F + A108V + R354K and/or G284L/S + H287D + E289A |
| DS698 | L131P + C173R + R325A + E328N | L52F + A108V + R354K and/or G284L/S + H287D + E289A |
| DS699 | L131P + C173R + R325A | L52F + A108V + R354K and/or G284L/S + H287D + E289A |
| DS700 | L131P + C173R + E328L | L52F + A108V + R354K and/or G284L/S + H287D + E289A |
| DS701 | L131P + C173R + E328N | L52F + A108V + R354K and/or G284L/S + H287D + E289A |
| DS702 | L131P + C173R | L52F + A108V + R354K and/or G284L/S + H287D + E289A |
| DS703 | L131P + C173G + R207L + D250V + R325P + E328L | L52F + A108V + R354K and/or G284L/S + H287D + E289A |
| DS704 | L131P + C173G + R207L + D250V + R325P + E328N | L52F + A108V + R354K and/or G284L/S + H287D + E289A |
| DS705 | L131P + C173G + R207L + D250V + R325P | L52F + A108V + R354K and/or G284L/S + H287D + E289A |
| DS706 | L131P + C173G + R207L + D250V + R325A + E328L | L52F + A108V + R354K and/or G284L/S + H287D + E289A |
| DS707 | L131P + C173G + R207L + D250V + R325A + E328N | L52F + A108V + R354K and/or G284L/S + H287D + E289A |
| DS708 | L131P + C173G + R207L + D250V + R325A | L52F + A108V + R354K and/or G284L/S + H287D + E289A |
| DS709 | L131P + C173G + R207L + D250V + E328L | L52F + A108V + R354K and/or G284L/S + H287D + E289A |
| DS710 | L131P + C173G + R207L + D250V + E328N | L52F + A108V + R354K and/or G284L/S + H287D + E289A |
| DS711 | L131P + C173G + R207L + D250V | L52F + A108V + R354K and/or G284L/S + H287D + E289A |
| DS712 | L131P + C173G + R207L + R325P + E328L | L52F + A108V + R354K and/or G284L/S + H287D + E289A |
| DS713 | L131P + C173G + R207L + R325P + E328N | L52F + A108V + R354K and/or G284L/S + H287D + E289A |
| DS714 | L131P + C173G + R207L + R325P | L52F + A108V + R354K and/or G284L/S + H287D + E289A |
| DS715 | L131P + C173G + R207L + R325A + E328L | L52F + A108V + R354K and/or G284L/S + H287D + E289A |
| DS716 | L131P + C173G + R207L + R325A + E328N | L52F + A108V + R354K and/or G284L/S + H287D + E289A |
| DS717 | L131P + C173G + R207L + R325A | L52F + A108V + R354K and/or G284L/S + H287D + E289A |
| DS718 | L131P + C173G + R207L + E328L | L52F + A108V + R354K and/or G284L/S + H287D + E289A |
| DS719 | L131P + C173G + R207L + E328N | L52F + A108V + R354K and/or G284L/S + H287D + E289A |
| DS720 | L131P + C173G + R207L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS721 | L131P + C173G + R207N + D250V + R325P + E328L | L52F + A108V + R354K and/or G284L/S + H287D + E289A |
| DS722 | L131P + C173G + R207N + D250V + R325P + E328N | L52F + A108V + R354K and/or G284L/S + H287D + E289A |
| DS723 | L131P + C173G + R207N + D250V + R325P | L52F + A108V + R354K and/or G284L/S + H287D + E289A |
| DS724 | L131P + C173G + R207N + D250V + R325A + E328L | L52F + A108V + R354K and/or G284L/S + H287D + E289A |
| DS725 | L131P + C173G + R207N + D250V + R325A + E328N | L52F + A108V + R354K and/or G284L/S + H287D + E289A |
| DS726 | L131P + C173G + R207N + D250V + R325A | L52F + A108V + R354K and/or G284L/S + H287D + E289A |
| DS727 | L131P + C173G + R207N + D250V + E328L | L52F + A108V + R354K and/or G284L/S + H287D + E289A |
| DS728 | L131P + C173G + R207N + D250V + E328N | L52F + A108V + R354K and/or G284L/S + H287D + E289A |
| DS729 | L131P + C173G + R207N + D250V | L52F + A108V + R354K and/or G284L/S + H287D + E289A |
| DS730 | L131P + C173G + R207N + R325P + E328L | L52F + A108V + R354K and/or G284L/S + H287D + E289A |
| DS731 | L131P + C173G + R207N + R325P + E328N | L52F + A108V + R354K and/or G284L/S + H287D + E289A |
| DS732 | L131P + C173G + R207N + R325P | L52F + A108V + R354K and/or G284L/S + H287D + E289A |
| DS733 | L131P + C173G + R207N + R325A + E328L | L52F + A108V + R354K and/or G284L/S + H287D + E289A |
| DS734 | L131P + C173G + R207N + R325A + E328N | L52F + A108V + R354K and/or G284L/S + H287D + E289A |
| DS735 | L131P + C173G + R207N + R325A | L52F + A108V + R354K and/or G284L/S + H287D + E289A |
| DS736 | L131P + C173G + R207N + E328L | L52F + A108V + R354K and/or G284L/S + H287D + E289A |
| DS737 | L131P + C173G + R207N + E328N | L52F + A108V + R354K and/or G284L/S + H287D + E289A |
| DS738 | L131P + C173G + R207N | L52F + A108V + R354K and/or G284L/S + H287D + E289A |
| DS739 | L131P + C173G + D250V + R325P + E328L | L52F + A108V + R354K and/or G284L/S + H287D + E289A |
| DS740 | L131P + C173G + D250V + R325P + E328N | L52F + A108V + R354K and/or G284L/S + H287D + E289A |
| DS741 | L131P + C173G + D250V + R325P | L52F + A108V + R354K and/or G284L/S + H287D + E289A |
| DS742 | L131P + C173G + D250V + R325A + E328L | L52F + A108V + R354K and/or G284L/S + H287D + E289A |
| DS743 | L131P + C173G + D250V + R325A + E328N | L52F + A108V + R354K and/or G284L/S + H287D + E289A |
| DS744 | L131P + C173G + D250V + R325A | L52F + A108V + R354K and/or G284L/S + H287D + E289A |
| DS745 | L131P + C173G + D250V + E328L | L52F + A108V + R354K and/or G284L/S + H287D + E289A |
| DS746 | L131P + C173G + D250V + E328N | L52F + A108V + R354K and/or G284L/S + H287D + E289A |
| DS747 | L131P + C173G + D250V | L52F + A108V + R354K and/or G284L/S + H287D + E289A |
| DS748 | L131P + C173G + R325P + E328L | L52F + A108V + R354K and/or G284L/S + H287D + E289A |
| DS749 | L131P + C173G + R325P + E328N | L52F + A108V + R354K and/or G284L/S + H287D + E289A |
| DS750 | L131P + C173G + R325P | L52F + A108V + R354K and/or G284L/S + H287D + E289A |
| DS751 | L131P + C173G + R325A + E328L | L52F + A108V + R354K and/or G284L/S + H287D + E289A |
| DS752 | L131P + C173G + R325A + E328N | L52F + A108V + R354K and/or G284L/S + H287D + E289A |
| DS753 | L131P + C173G + R325A | L52F + A108V + R354K and/or G284L/S + H287D + E289A |
| DS754 | L131P + C173G + E328L | L52F + A108V + R354K and/or G284L/S + H287D + E289A |
| DS755 | L131P + C173G + E328N | L52F + A108V + R354K and/or G284L/S + H287D + E289A |
| DS756 | L131P + C173G | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
| --- | --- | --- |
| DS811 | C173R + R207L + D250V + R325P + E328L | L52F + A108V + R354K and/or G284L/S + H287D + E289A |
| DS812 | C173R + R207L + D250V + R325P + E328N | L52F + A108V + R354K and/or G284L/S + H287D + E289A |
| DS813 | C173R + R207L + D250V + R325P | L52F + A108V + R354K and/or G284L/S + H287D + E289A |
| DS814 | C173R + R207L + D250V + R325A + E328L | L52F + A108V + R354K and/or G284L/S + H287D + E289A |
| DS815 | C173R + R207L + D250V + R325A + E328N | L52F + A108V + R354K and/or G284L/S + H287D + E289A |
| DS816 | C173R + R207L + D250V + R325A | L52F + A108V + R354K and/or G284L/S + H287D + E289A |
| DS817 | C173R + R207L + D250V + E328L | L52F + A108V + R354K and/or G284L/S + H287D + E289A |
| DS818 | C173R + R207L + D250V + E328N | L52F + A108V + R354K and/or G284L/S + H287D + E289A |
| DS819 | C173R + R207L + D250V | L52F + A108V + R354K and/or G284L/S + H287D + E289A |
| DS820 | C173R + R207L + R325P + E328L | L52F + A108V + R354K and/or G284L/S + H287D + E289A |
| DS821 | C173R + R207L + R325P + E328N | L52F + A108V + R354K and/or G284L/S + H287D + E289A |
| DS822 | C173R + R207L + R325P | L52F + A108V + R354K and/or G284L/S + H287D + E289A |
| DS823 | C173R + R207L + R325A + E328L | L52F + A108V + R354K and/or G284L/S + H287D + E289A |
| DS824 | C173R + R207L + R325A + E328N | L52F + A108V + R354K and/or G284L/S + H287D + E289A |
| DS825 | C173R + R207L + R325A | L52F + A108V + R354K and/or G284L/S + H287D + E289A |
| DS826 | C173R + R207L + E328L | L52F + A108V + R354K and/or G284L/S + H287D + E289A |
| DS827 | C173R + R207L + E328N | L52F + A108V + R354K and/or G284L/S + H287D + E289A |
| DS828 | C173R + R207L | L52F + A108V + R354K and/or G284L/S + H287D + E289A |
| DS829 | C173R + R207N + D250V + R325P + E328L | L52F + A108V + R354K and/or G284L/S + H287D + E289A |
| DS830 | C173R + R207N + D250V + R325P + E328N | L52F + A108V + R354K and/or G284L/S + H287D + E289A |
| DS831 | C173R + R207N + D250V + R325P | L52F + A108V + R354K and/or G284L/S + H287D + E289A |
| DS832 | C173R + R207N + D250V + R325A + E328L | L52F + A108V + R354K and/or G284L/S + H287D + E289A |
| DS833 | C173R + R207N + D250V + R325A + E328N | L52F + A108V + R354K and/or G284L/S + H287D + E289A |
| DS834 | C173R + R207N + D250V + R325A | L52F + A108V + R354K and/or G284L/S + H287D + E289A |
| DS835 | C173R + R207N + D250V + E328L | L52F + A108V + R354K and/or G284L/S + H287D + E289A |
| DS836 | C173R + R207N + D250V + E328N | L52F + A108V + R354K and/or G284L/S + H287D + E289A |
| DS837 | C173R + R207N + D250V | L52F + A108V + R354K and/or G284L/S + H287D + E289A |
| DS838 | C173R + R207N + R325P + E328L | L52F + A108V + R354K and/or G284L/S + H287D + E289A |
| DS839 | C173R + R207N + R325P + E328N | L52F + A108V + R354K and/or G284L/S + H287D + E289A |
| DS840 | C173R + R207N + R325P | L52F + A108V + R354K and/or G284L/S + H287D + E289A |
| DS841 | C173R + R207N + R325A + E328L | L52F + A108V + R354K and/or G284L/S + H287D + E289A |
| DS842 | C173R + R207N + R325A + E328N | L52F + A108V + R354K and/or G284L/S + H287D + E289A |
| DS843 | C173R + R207N + R325A | L52F + A108V + R354K and/or G284L/S + H287D + E289A |
| DS844 | C173R + R207N + E328L | L52F + A108V + R354K and/or G284L/S + H287D + E289A |
| DS845 | C173R + R207N + E328N | L52F + A108V + R354K and/or G284L/S + H287D + E289A |
| DS846 | C173R + R207N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS847 | C173R + D250V + R325P + E328L | L52F + A108V + R354K and/or G284L/S + H287D + E289A |
| DS848 | C173R + D250V + R325P + E328N | L52F + A108V + R354K and/or G284L/S + H287D + E289A |
| DS849 | C173R + D250V + R325P | L52F + A108V + R354K and/or G284L/S + H287D + E289A |
| DS850 | C173R + D250V + R325A + E328L | L52F + A108V + R354K and/or G284L/S + H287D + E289A |
| DS851 | C173R + D250V + R325A + E328N | L52F + A108V + R354K and/or G284L/S + H287D + E289A |
| DS852 | C173R + D250V + R325A | L52F + A108V + R354K and/or G284L/S + H287D + E289A |
| DS853 | C173R + D250V + E328L | L52F + A108V + R354K and/or G284L/S + H287D + E289A |
| DS854 | C173R + D250V + E328N | L52F + A108V + R354K and/or G284L/S + H287D + E289A |
| DS855 | C173R + D250V | L52F + A108V + R354K and/or G284L/S + H287D + E289A |
| DS856 | C173R + R325P + E328L | L52F + A108V + R354K and/or G284L/S + H287D + E289A |
| DS857 | C173R + R325P + E328N | L52F + A108V + R354K and/or G284L/S + H287D + E289A |
| DS858 | C173R + R325P | L52F + A108V + R354K and/or G284L/S + H287D + E289A |
| DS859 | C173R + R325A + E328L | L52F + A108V + R354K and/or G284L/S + H287D + E289A |
| DS860 | C173R + R325A + E328N | L52F + A108V + R354K and/or G284L/S + H287D + E289A |
| DS861 | C173R + R325A | L52F + A108V + R354K and/or G284L/S + H287D + E289A |
| DS862 | C173R + E328L | L52F + A108V + R354K and/or G284L/S + H287D + E289A |
| DS863 | C173R + E328N | L52F + A108V + R354K and/or G284L/S + H287D + E289A |
| DS864 | C173R | L52F + A108V + R354K and/or G284L/S + H287D + E289A |
| DS865 | C173G + R207L + D250V + R325P + E328L | L52F + A108V + R354K and/or G284L/S + H287D + E289A |
| DS866 | C173G + R207L + D250V + R325P + E328N | L52F + A108V + R354K and/or G284L/S + H287D + E289A |
| DS867 | C173G + R207L + D250V + R325P | L52F + A108V + R354K and/or G284L/S + H287D + E289A |
| DS868 | C173G + R207L + D250V + R325A + E328L | L52F + A108V + R354K and/or G284L/S + H287D + E289A |
| DS869 | C173G + R207L + D250V + R325A + E328N | L52F + A108V + R354K and/or G284L/S + H287D + E289A |
| DS870 | C173G + R207L + D250V + R325A | L52F + A108V + R354K and/or G284L/S + H287D + E289A |
| DS871 | C173G + R207L + D250V + E328L | L52F + A108V + R354K and/or G284L/S + H287D + E289A |
| DS872 | C173G + R207L + D250V + E328N | L52F + A108V + R354K and/or G284L/S + H287D + E289A |
| DS873 | C173G + R207L + D250V | L52F + A108V + R354K and/or G284L/S + H287D + E289A |
| DS874 | C173G + R207L + R325P + E328L | L52F + A108V + R354K and/or G284L/S + H287D + E289A |
| DS875 | C173G + R207L + R325P + E328N | L52F + A108V + R354K and/or G284L/S + H287D + E289A |
| DS876 | C173G + R207L + R325P | L52F + A108V + R354K and/or G284L/S + H287D + E289A |
| DS877 | C173G + R207L + R325A + E328L | L52F + A108V + R354K and/or G284L/S + H287D + E289A |
| DS878 | C173G + R207L + R325A + E328N | L52F + A108V + R354K and/or G284L/S + H287D + E289A |
| DS879 | C173G + R207L + R325A | L52F + A108V + R354K and/or G284L/S + H287D + E289A |
| DS880 | C173G + R207L + E328L | L52F + A108V + R354K and/or G284L/S + H287D + E289A |
| DS881 | C173G + R207L + E328N | L52F + A108V + R354K and/or G284L/S + H287D + E289A |
| DS882 | C173G + R207L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS883 | C173G + R207N + D250V + R325P + E328L | L52F + A108V + R354K and/or G284L/S + H287D + E289A |
| DS884 | C173G + R207N + D250V + R325P + E328N | L52F + A108V + R354K and/or G284L/S + H287D + E289A |
| DS885 | C173G + R207N + D250V + R325P | L52F + A108V + R354K and/or G284L/S + H287D + E289A |
| DS886 | C173G + R207N + D250V + R325A + E328L | L52F + A108V + R354K and/or G284L/S + H287D + E289A |
| DS887 | C173G + R207N + D250V + R325A + E328N | L52F + A108V + R354K and/or G284L/S + H287D + E289A |
| DS888 | C173G + R207N + D250V + R325A | L52F + A108V + R354K and/or G284L/S + H287D + E289A |
| DS889 | C173G + R207N + D250V + E328L | L52F + A108V + R354K and/or G284L/S + H287D + E289A |
| DS890 | C173G + R207N + D250V + E328N | L52F + A108V + R354K and/or G284L/S + H287D + E289A |
| DS891 | C173G + R207N + D250V | L52F + A108V + R354K and/or G284L/S + H287D + E289A |
| DS892 | C173G + R207N + R325P + E328L | L52F + A108V + R354K and/or G284L/S + H287D + E289A |
| DS893 | C173G + R207N + R325P + E328N | L52F + A108V + R354K and/or G284L/S + H287D + E289A |
| DS894 | C173G + R207N + R325P | L52F + A108V + R354K and/or G284L/S + H287D + E289A |
| DS895 | C173G + R207N + R325A + E328L | L52F + A108V + R354K and/or G284L/S + H287D + E289A |
| DS896 | C173G + R207N + R325A + E328N | L52F + A108V + R354K and/or G284L/S + H287D + E289A |
| DS897 | C173G + R207N + R325A | L52F + A108V + R354K and/or G284L/S + H287D + E289A |
| DS898 | C173G + R207N + E328L | L52F + A108V + R354K and/or G284L/S + H287D + E289A |
| DS899 | C173G + R207N + E328N | L52F + A108V + R354K and/or G284L/S + H287D + E289A |
| DS900 | C173G + R207N | L52F + A108V + R354K and/or G284L/S + H287D + E289A |
| DS901 | C173G + D250V + R325P + E328L | L52F + A108V + R354K and/or G284L/S + H287D + E289A |
| DS902 | C173G + D250V + R325P + E328N | L52F + A108V + R354K and/or G284L/S + H287D + E289A |
| DS903 | C173G + D250V + R325P | L52F + A108V + R354K and/or G284L/S + H287D + E289A |
| DS904 | C173G + D250V + R325A + E328L | L52F + A108V + R354K and/or G284L/S + H287D + E289A |
| DS905 | C173G + D250V + R325A + E328N | L52F + A108V + R354K and/or G284L/S + H287D + E289A |
| DS906 | C173G + D250V + R325A | L52F + A108V + R354K and/or G284L/S + H287D + E289A |
| DS907 | C173G + D250V + E328L | L52F + A108V + R354K and/or G284L/S + H287D + E289A |
| DS908 | C173G + D250V + E328N | L52F + A108V + R354K and/or G284L/S + H287D + E289A |
| DS909 | C173G + D250V | L52F + A108V + R354K and/or G284L/S + H287D + E289A |
| DS910 | C173G + R325P + E328L | L52F + A108V + R354K and/or G284L/S + H287D + E289A |
| DS911 | C173G + R325P + E328N | L52F + A108V + R354K and/or G284L/S + H287D + E289A |
| DS912 | C173G + R325P | L52F + A108V + R354K and/or G284L/S + H287D + E289A |
| DS913 | C173G + R325A + E328L | L52F + A108V + R354K and/or G284L/S + H287D + E289A |
| DS914 | C173G + R325A + E328N | L52F + A108V + R354K and/or G284L/S + H287D + E289A |
| DS915 | C173G + R325A | L52F + A108V + R354K and/or G284L/S + H287D + E289A |
| DS916 | C173G + E328L | L52F + A108V + R354K and/or G284L/S + H287D + E289A |
| DS917 | C173G + E328N | L52F + A108V + R354K and/or G284L/S + H287D + E289A |
| DS918 | C173G | L52F + A108V + R354K and/or G284L/S + H287D + E289A |

In a particular embodiment, the variants of the invention comprise the amino acid sequence of SEQ ID NO:2 (or functionally equivalent sequence) and optionally additional amino acid fragments at the C-ter or N-ter. In another embodiment, the variants of the invention consist solely on the amino acid sequence of SEQ ID NO:2 (or functionally equivalent sequence). More particularly, in a particular embodiment, the variants of the invention are deprived of the BRTC-like domain, which corresponds to residues 1 to 129 of SEQ ID NO: 1.

According to a second aspect of the invention, the variant of Terminal deoxynucleotidyl Transferase (TdT) (i) comprises an amino acid sequence as set forth in SEQ ID NO:2 or a functionally equivalent sequence (such as, SEQ ID NOs:11, 13, 15, 17, 19, 21, 23, 25, 27, 29, 31, 33 or 35) or an amino acid sequence having a specified percent sequence identity of any of the foregoing sequences, with at least three amino acid substitutions selected from M63R/Q, L131P, C173G/R, R207L/N, D250V, R325P/N and E328N/L/T/S, or a functionally equivalent residue, wherein the positions are numbered by reference to the amino acid sequence set forth in SEQ ID NO:1 or as set forth directly elsewhere herein in respect of their individual SEQ ID NOs, (ii) is able to synthesize a nucleic acid fragment without template and (iii) is able to incorporate a modified nucleotide, such as a 3'-O-modified nucleotide, into the nucleic fragment.

For instance, the variant of TdT comprises an amino acid sequence within a specified percent sequence identity of SEQ ID NO:2 and a combination of substitutions selected from M63R+L131P+R207L, M63R+L131P+R207N, M63R+L131P+D250V, M63R+L131P+R325P, M63R+L131P+R325A, M63R+L131P+E328L, M63R+L131P+E328N, M63R+R207L+D250V, M63R+R207L+R325P, M63R+R207L+R325A, M63R+R207L+E328L, M63R+R207L+E328N, M63R+R207N+D250V, M63R+R207N+R325P, M63R+R207N+R325A, M63R+R207N+E328L, M63R+R207N+E328N, M63R+D250V+R325P, M63R+D250V+R325A, M63R+R325P+E328L, M63R+R325P+E328N, M63R+R325A+E328L, M63R+R325A+E328N, M63Q+L131P+R207L, M63Q+L131P+R207N, M63Q+L131P+D250V, M63Q+L131P+R325P, M63Q+L131P+R325A, M63Q+L131P+E328L, M63Q+L131P+E328N, M63Q+R207L+D250V, M63Q+R207L+R325P, M63Q+R207L+R325A, M63Q+R207L+E328L, M63Q+R207L+E328N, M63Q+D250V+R325P, M63Q+D250V+R325A, M63Q+D250V+E328L, M63Q+D250V+E328N, M63Q+R325P+E328L, M63Q+R325P+E328N, M63Q+R325A+E328L, M63Q+R325A+E328N, L131P+R207L+D250V, L131P+R207L+R325A, L131P+R207L+E328L, L131P+R207L+E328N, L131P+R207N+D250V, L131P+R207N+R325P, L131P+R207N+R325A, L131P+R207N+E328L, L131P+R207N+E328N, L131P+D250V+R325P, L131P+D250V+R325A, L131P+D250V+E328L, L131P+D250V+E328N, L131P+R325P+E328L, L131P+R325P+E328N, L131P+R325A+E328L, L131P+R325A+E328N, R207L+D250V+R325P, R207L+D250V+R325A, R207L+D250V+E328L, R207L+D250V+E328N, R207L+R325P+E328L, R207L+R325P+E328N, R207L+R325A+E328L, R207L+R325A+E328N, R207N+D250V+R325P, R207N+D250V+R325A, R207N+D250V+E328L, R207N+D250V+E328N, R207N+R325P+E328L, R207N+R325P+E328N, R207N+R325A+E328L, R207N+R325A+E328N, D250V+R325P+E328L, D250V+R325P+E328N, D250V+R325A+E328L, D250V+R325A+E328N and R207L+D250V+R325P, or functionally equivalent residue(s) wherein the above position numbers are with respect to SEQ ID NO:2.

In a particular embodiment, the variant of TdT comprises an amino acid sequence within a specified percent sequence identity of SEQ ID NO:2, or functionally equivalent sequence, with the combination of substitutions R207L+R325P+E328L (DS928), or functionally equivalent residues.

In a particular embodiment, the variant of TdT comprises an amino acid sequence within a specified percent sequence identity of SEQ ID NO:2, or functionally equivalent sequence, with the combination of substitutions R207N+R325A+E328N (DS950), or functionally equivalent residues.

Such variant may further comprise at least one substitution at position corresponding to residues selected from L52, A108, L131, T340, G284, H287, E289, W450, R354 and A510, or functionally equivalent residue(s).

As exposed above, said variant may also comprise the combination of constant mutations L52F+A108V+R354K and/or G284US+H287D+E289A, or functionally equivalent residue(s).

According to a further aspect, the invention provides a variant of Terminal deoxynucleotidyl Transferase (TdT) which (i) comprises an amino acid sequence within a specified percent sequence identity of SEQ ID NO:2 or a functionally equivalent sequence, with at least one amino acid substitution selected from M63R, M63Q, L131P, R207L, R207N, D250V, R325P, R325A, E328L, E328N, or functionally equivalent residue(s), (ii) is able to synthesize a nucleic acid fragment without a template and (iii) is able to incorporate a 3'-O-modified nucleotide into the nucleic fragment.

In another aspect, the invention provides a variant of Terminal deoxynucleotidyl Transferase (TdT) which (i) comprises an amino acid sequence within a specified percent sequence identity of SEQ ID NO:2 or a functionally equivalent sequence, with at least the combination of substitutions selected from M63R+L131P, M63R+R207L, M63R+R207N, M63R+D250V, M63R+R325P, M63R+R325A, M63R+E328L, M63R+E328N, M63Q+L131P, M63Q+R207L, M63Q+R207N, M63Q+D250V, M63Q+R325P, M63Q+R325A, M63Q+E328L, M63Q+E328N, L131P+R207L, L131P+R207N, L131P+D250V, L131P+R325P, L131P+R325A, L131P+E328L, L131P+E328N, R207L+D250V, R207L+R325P, R207L+R325A, R207L+E328L, R207L+E328N, R207N+D250V, R207N+R325P, R207N+R325A, R207N+E328L, R207N+E328N, D250V+R325P, D250V+R325A, D250V+E328L, D250V+E328N, R325P+E328L, R325P+E328N, R325A+E328L and R325A+E328N, or functionally equivalent residue(s), wherein the positions are numbered by reference to the amino acid sequence set forth in SEQ ID NO:2, (ii) is able to synthesize a nucleic acid fragment without a template and (iii) is able to incorporate a 3'-O-modified nucleotide into the nucleic fragment.

It is thus an object of the invention to provide a TdT variant having an amino acid sequence within a specified percent sequence identity of SEQ ID NO:2, or functionally equivalent sequence, with any substitution or combination of substitutions listed in Table 6, listed as "Variable Mutations", or functionally equivalent residue(s) and optionally one or both combinations of constant mutations L52F+A108V+R354K an G284L/S+H287D+E289A, or functionally equivalent residue(s).

According to a particular embodiment, the variant comprises at least one substitution or combination of substitutions as listed in Table 6, and optionally one or more additional mutation(s).

TABLE 2

Variants of TdT having the amino acid sequence of SEQ ID NO:2, or an amino acid sequence within a specified percent sequence identity thereof, and further including the following Variable Mutations and Optional Constant Mutations (wherein amino acid position numbers are with respect to SEQ ID NO:2).

| Name | Variable Mutations | Optional Constant Mutations |
|---|---|---|
| DS109 | M63R + L131P + R207L + D250V + R325P + E328L | L52F + A108V + R354K and/or G284L/S + H287D + E289A |
| DS110 | M63R + L131P + R207L + D250V + R325P + E328N | L52F + A108V + R354K and/or G284L/S + H287D + E289A |
| DS111 | M63R + L131P + R207L + D250V + R325P | L52F + A108V + R354K and/or G284L/S + H287D + E289A |
| DS112 | M63R + L131P + R207L + D250V + R325A + E328L | L52F + A108V + R354K and/or G284L/S + H287D + E289A |
| DS113 | M63R + L131P + R207L + D250V + R325A + E328N | L52F + A108V + R354K and/or G284L/S + H287D + E289A |
| DS114 | M63R + L131P + R207L + D250V + R325A | L52F + A108V + R354K and/or G284L/S + H287D + E289A |
| DS115 | M63R + L131P + R207L + D250V + E328L | L52F + A108V + R354K and/or G284L/S + H287D + E289A |
| DS116 | M63R + L131P + R207L + D250V + E328N | L52F + A108V + R354K and/or G284L/S + H287D + E289A |
| DS117 | M63R + L131P + R207L + D250V | L52F + A108V + R354K and/or G284L/S + H287D + E289A |
| DS118 | M63R + L131P + R207L + R325P + E328L | L52F + A108V + R354K and/or G284L/S + H287D + E289A |
| DS119 | M63R + L131P + R207L + R325P + E328N | L52F + A108V + R354K and/or G284L/S + H287D + E289A |
| DS120 | M63R + L131P + R207L + R325P | L52F + A108V + R354K and/or G284L/S + H287D + E289A |
| DS121 | M63R + L131P + R207L + R325A + E328L | L52F + A108V + R354K and/or G284L/S + H287D + E289A |
| DS122 | M63R + L131P + R207L + R325A + E328N | L52F + A108V + R354K and/or G284L/S + H287D + E289A |
| DS123 | M63R + L131P + R207L + R325A | L52F + A108V + R354K and/or G284L/S + H287D + E289A |
| DS124 | M63R + L131P + R207L + E328L | L52F + A108V + R354K and/or G284L/S + H287D + E289A |
| DS125 | M63R + L131P + R207L + E328N | L52F + A108V + R354K and/or G284L/S + H287D + E289A |
| DS126 | M63R + L131P + R207L | L52F + A108V + R354K and/or G284L/S + H287D + E289A |
| DS127 | M63R + L131P + R207N + D250V + R325P + E328L | L52F + A108V + R354K and/or G284L/S + H287D + E289A |
| DS128 | M63R + L131P + R207N + D250V + R325P + E328N | L52F + A108V + R354K and/or G284L/S + H287D + E289A |
| DS129 | M63R + L131P + R207N + D250V + R325P | L52F + A108V + R354K and/or G284L/S + H287D + E289A |
| DS130 | M63R + L131P + R207N + D250V + R325A + E328L | L52F + A108V + R354K and/or G284L/S + H287D + E289A |
| DS131 | M63R + L131P + R207N + D250V + R325A + E328N | L52F + A108V + R354K and/or G284L/S + H287D + E289A |
| DS132 | M63R + L131P + R207N + D250V + R325A | L52F + A108V + R354K and/or G284L/S + H287D + E289A |
| DS133 | M63R + L131P + R207N + D250V + E328L | L52F + A108V + R354K and/or G284L/S + H287D + E289A |
| DS134 | M63R + L131P + R207N + D250V + E328N | L52F + A108V + R354K and/or G284L/S + H287D + E289A |
| DS135 | M63R + L131P + R207N + D250V | L52F + A108V + R354K and/or G284L/S + H287D + E289A |
| DS136 | M63R + L131P + R207N + R325P + E328L | L52F + A108V + R354K and/or G284L/S + H287D + E289A |
| DS137 | M63R + L131P + R207N + R325P + E328N | L52F + A108V + R354K and/or G284L/S + H287D + E289A |
| DS138 | M63R + L131P + R207N + R325P | L52F + A108V + R354K and/or G284L/S + H287D + E289A |
| DS139 | M63R + L131P + R207N + R325A + E328L | L52F + A108V + R354K and/or G284L/S + H287D + E289A |
| DS140 | M63R + L131P + R207N + R325A + E328N | L52F + A108V + R354K and/or G284L/S + H287D + E289A |
| DS141 | M63R + L131P + R207N + R325A | L52F + A108V + R354K and/or G284L/S + H287D + E289A |
| DS142 | M63R + L131P + R207N + E328L | L52F + A108V + R354K and/or G284L/S + H287D + E289A |
| DS143 | M63R + L131P + R207N + E328N | L52F + A108V + R354K and/or G284L/S + H287D + E289A |
| DS144 | M63R + L131P + R207N | L52F + A108V + R354K and/or G284L/S + H287D + E289A |
| DS145 | M63R + L131P + D250V + R325P + E328L | L52F + A108V + R354K and/or G284L/S + H287D + E289A |
| DS146 | M63R + L131P + D250V + R325P + E328N | L52F + A108V + R354K and/or G284L/S + H287D + E289A |
| DS147 | M63R + L131P + D250V + R325P | L52F + A108V + R354K and/or G284L/S + H287D + E289A |
| DS148 | M63R + L131P + D250V + R325A + E328L | L52F + A108V + R354K and/or G284L/S + H287D + E289A |
| DS149 | M63R + L131P + D250V + R325A + E328N | L52F + A108V + R354K and/or G284L/S + H287D + E289A |
| DS150 | M63R + L131P + D250V + R325A | L52F + A108V + R354K and/or G284L/S + H287D + E289A |
| DS151 | M63R + L131P + D250V + E328L | L52F + A108V + R354K and/or G284L/S + H287D + E289A |
| DS152 | M63R + L131P + D250V + E328N | L52F + A108V + R354K and/or G284L/S + H287D + E289A |
| DS153 | M63R + L131P + D250V | L52F + A108V + R354K and/or G284L/S + H287D + E289A |
| DS154 | M63R + L131P + R325P + E328L | L52F + A108V + R354K and/or G284L/S + H287D + E289A |
| DS155 | M63R + L131P + R325P + E328N | L52F + A108V + R354K and/or G284L/S + H287D + E289A |
| DS156 | M63R + L131P + R325P | L52F + A108V + R354K and/or G284L/S + H287D + E289A |
| DS157 | M63R + L131P + R325A + E328L | L52F + A108V + R354K and/or G284L/S + H287D + E289A |
| DS158 | M63R + L131P + R325A + E328N | L52F + A108V + R354K and/or G284L/S + H287D + E289A |
| DS159 | M63R + L131P + R325A | L52F + A108V + R354K and/or G284L/S + H287D + E289A |
| DS160 | M63R + L131P + E328L | L52F + A108V + R354K and/or G284L/S + H287D + E289A |
| DS161 | M63R + L131P + E328N | L52F + A108V + R354K and/or G284L/S + H287D + E289A |
| DS162 | M63R + L131P | L52F + A108V + R354K and/or G284L/S + H287D + E289A |
| DS271 | M63R + R207L + D250V + R325P + E328L | L52F + A108V + R354K and/or G284L/S + H287D + E289A |
| DS272 | M63R + R207L + D250V + R325P + E328N | L52F + A108V + R354K and/or G284L/S + H287D + E289A |
| DS273 | M63R + R207L + D250V + R325P | L52F + A108V + R354K and/or G284L/S + H287D + E289A |
| DS274 | M63R + R207L + D250V + R325A + E328L | L52F + A108V + R354K and/or G284L/S + H287D + E289A |
| DS275 | M63R + R207L + D250V + R325A + E328N | L52F + A108V + R354K and/or G284L/S + H287D + E289A |
| DS276 | M63R + R207L + D250V + R325A | L52F + A108V + R354K and/or G284L/S + H287D + E289A |
| DS277 | M63R + R207L + D250V + E328L | L52F + A108V + R354K and/or G284L/S + H287D + E289A |
| DS278 | M63R + R207L + D250V + E328N | L52F + A108V + R354K and/or G284L/S + H287D + E289A |
| DS279 | M63R + R207L + D250V | L52F + A108V + R354K and/or G284L/S + H287D + E289A |
| DS280 | M63R + R207L + R325P + E328L | L52F + A108V + R354K and/or G284L/S + H287D + E289A |
| DS281 | M63R + R207L + R325P + E328N | L52F + A108V + R354K and/or G284L/S + H287D + E289A |
| DS282 | M63R + R207L + R325P | L52F + A108V + R354K and/or G284L/S + H287D + E289A |
| DS283 | M63R + R207L + R325A + E328L | L52F + A108V + R354K and/or G284L/S + H287D + E289A |
| DS284 | M63R + R207L + R325A + E328N | L52F + A108V + R354K and/or G284L/S + H287D + E289A |
| DS285 | M63R + R207L + R325A | L52F + A108V + R354K and/or G284L/S + H287D + E289A |
| DS286 | M63R + R207L + E328L | L52F + A108V + R354K and/or G284L/S + H287D + E289A |
| DS287 | M63R + R207L + E328N | L52F + A108V + R354K and/or G284L/S + H287D + E289A |
| DS288 | M63R + R207L | L52F + A108V + R354K and/or G284L/S + H287D + E289A |
| DS289 | M63R + R207N + D250V + R325P + E328L | L52F + A108V + R354K and/or G284L/S + H287D + E289A |

TABLE 2-continued

Variants of TdT having the amino acid sequence of SEQ ID NO:2, or an amino acid sequence within a specified percent sequence identity thereof, and further including the following Variable Mutations and Optional Constant Mutations (wherein amino acid position numbers are with respect to SEQ ID NO:2).

| Name | Variable Mutations | Optional Constant Mutations |
| --- | --- | --- |
| DS290 | M63R + R207N + D250V + R325P + E328N | L52F + A108V + R354K and/or G284L/S + H287D + E289A |
| DS291 | M63R + R207N + D250V + R325P | L52F + A108V + R354K and/or G284L/S + H287D + E289A |
| DS292 | M63R + R207N + D250V + R325A + E328L | L52F + A108V + R354K and/or G284L/S + H287D + E289A |
| DS293 | M63R + R207N + D250V + R325A + E328N | L52F + A108V + R354K and/or G284L/S + H287D + E289A |
| DS294 | M63R + R207N + D250V + R325A | L52F + A108V + R354K and/or G284L/S + H287D + E289A |
| DS295 | M63R + R207N + D250V + E328L | L52F + A108V + R354K and/or G284L/S + H287D + E289A |
| DS296 | M63R + R207N + D250V + E328N | L52F + A108V + R354K and/or G284L/S + H287D + E289A |
| DS297 | M63R + R207N + D250V | L52F + A108V + R354K and/or G284L/S + H287D + E289A |
| DS298 | M63R + R207N + R325P + E328L | L52F + A108V + R354K and/or G284L/S + H287D + E289A |
| DS299 | M63R + R207N + R325P + E328N | L52F + A108V + R354K and/or G284L/S + H287D + E289A |
| DS300 | M63R + R207N + R325P | L52F + A108V + R354K and/or G284L/S + H287D + E289A |
| DS301 | M63R + R207N + R325A + E328L | L52F + A108V + R354K and/or G284L/S + H287D + E289A |
| DS173 | M63R + R207N + R325A + E328N | L52F + A108V + R354K and/or G284L/S + H287D + E289A |
| DS303 | M63R + R207N + R325A | L52F + A108V + R354K and/or G284L/S + H287D + E289A |
| DS304 | M63R + R207N + E328L | L52F + A108V + R354K and/or G284L/S + H287D + E289A |
| DS305 | M63R + R207N + E328N | L52F + A108V + R354K and/or G284L/S + H287D + E289A |
| DS306 | M63R + R207N | L52F + A108V + R354K and/or G284L/S + H287D + E289A |
| DS307 | M63R + D250V + R325P + E328L | L52F + A108V + R354K and/or G284L/S + H287D + E289A |
| DS308 | M63R + D250V + R325P + E328N | L52F + A108V + R354K and/or G284L/S + H287D + E289A |
| DS309 | M63R + D250V + R325P | L52F + A108V + R354K and/or G284L/S + H287D + E289A |
| DS310 | M63R + D250V + R325A + E328L | L52F + A108V + R354K and/or G284L/S + H287D + E289A |
| DS311 | M63R + D250V + R325A + E328N | L52F + A108V + R354K and/or G284L/S + H287D + E289A |
| DS312 | M63R + D250V + R325A | L52F + A108V + R354K and/or G284L/S + H287D + E289A |
| DS313 | M63R + D250V + E328L | L52F + A108V + R354K and/or G284L/S + H287D + E289A |
| DS314 | M63R + D250V + E328N | L52F + A108V + R354K and/or G284L/S + H287D + E289A |
| DS315 | M63R + D250V | L52F + A108V + R354K and/or G284L/S + H287D + E289A |
| DS316 | M63R + R325P + E328L | L52F + A108V + R354K and/or G284L/S + H287D + E289A |
| DS317 | M63R + R325P + E328N | L52F + A108V + R354K and/or G284L/S + H287D + E289A |
| DS318 | M63R + R325P | L52F + A108V + R354K and/or G284L/S + H287D + E289A |
| DS319 | M63R + R325A + E328L | L52F + A108V + R354K and/or G284L/S + H287D + E289A |
| DS320 | M63R + R325A + E328N | L52F + A108V + R354K and/or G284L/S + H287D + E289A |
| DS321 | M63R + R325A | L52F + A108V + R354K and/or G284L/S + H287D + E289A |
| DS322 | M63R + E328L | L52F + A108V + R354K and/or G284L/S + H287D + E289A |
| DS323 | M63R + E328N | L52F + A108V + R354K and/or G284L/S + H287D + E289A |
| DS324 | M63R | L52F + A108V + R354K and/or G284L/S + H287D + E289A |
| DS433 | M63Q + L131P + R207L + D250V + R325P + E328L | L52F + A108V + R354K and/or G284L/S + H287D + E289A |
| DS434 | M63Q + L131P + R207L + D250V + R325P + E328N | L52F + A108V + R354K and/or G284L/S + H287D + E289A |
| DS435 | M63Q + L131P + R207L + D250V + R325P | L52F + A108V + R354K and/or G284L/S + H287D + E289A |
| DS436 | M63Q + L131P + R207L + D250V + R325A + E328L | L52F + A108V + R354K and/or G284L/S + H287D + E289A |
| DS437 | M63Q + L131P + R207L + D250V + R325A + E328N | L52F + A108V + R354K and/or G284L/S + H287D + E289A |
| DS438 | M63Q + L131P + R207L + D250V + R325A | L52F + A108V + R354K and/or G284L/S + H287D + E289A |
| DS439 | M63Q + L131P + R207L + D250V + E328L | L52F + A108V + R354K and/or G284L/S + H287D + E289A |
| DS440 | M63Q + L131P + R207L + D250V + E328N | L52F + A108V + R354K and/or G284L/S + H287D + E289A |
| DS441 | M63Q + L131P + R207L + D250V | L52F + A108V + R354K and/or G284L/S + H287D + E289A |
| DS442 | M63Q + L131P + R207L + R325P + E328L | L52F + A108V + R354K and/or G284L/S + H287D + E289A |
| DS443 | M63Q + L131P + R207L + R325P + E328N | L52F + A108V + R354K and/or G284L/S + H287D + E289A |
| DS444 | M63Q + L131P + R207L + R325P | L52F + A108V + R354K and/or G284L/S + H287D + E289A |
| DS445 | M63Q + L131P + R207L + R325A + E328L | L52F + A108V + R354K and/or G284L/S + H287D + E289A |
| DS446 | M63Q + L131P + R207L + R325A + E328N | L52F + A108V + R354K and/or G284L/S + H287D + E289A |
| DS447 | M63Q + L131P + R207L + R325A | L52F + A108V + R354K and/or G284L/S + H287D + E289A |
| DS448 | M63Q + L131P + R207L + E328L | L52F + A108V + R354K and/or G284L/S + H287D + E289A |
| DS449 | M63Q + L131P + R207L + E328N | L52F + A108V + R354K and/or G284L/S + H287D + E289A |
| DS450 | M63Q + L131P + R207L | L52F + A108V + R354K and/or G284L/S + H287D + E289A |
| DS451 | M63Q + L131P + R207N + D250V + R325P + E328L | L52F + A108V + R354K and/or G284L/S + H287D + E289A |
| DS452 | M63Q + L131P + R207N + D250V + R325P + E328N | L52F + A108V + R354K and/or G284L/S + H287D + E289A |
| DS453 | M63Q + L131P + R207N + D250V + R325P | L52F + A108V + R354K and/or G284L/S + H287D + E289A |
| DS325 | M63Q + L131P + R207N + D250V + R325A + E328L | L52F + A108V + R354K and/or G284L/S + H287D + E289A |
| DS455 | M63Q + L131P + R207N + D250V + R325A + E328N | L52F + A108V + R354K and/or G284L/S + H287D + E289A |
| DS456 | M63Q + L131P + R207N + D250V + R325A | L52F + A108V + R354K and/or G284L/S + H287D + E289A |
| DS328 | M63Q + L131P + R207N + D250V + E328L | L52F + A108V + R354K and/or G284L/S + H287D + E289A |
| DS458 | M63Q + L131P + R207N + D250V + E328N | L52F + A108V + R354K and/or G284L/S + H287D + E289A |
| DS459 | M63Q + L131P + R207N + D250V | L52F + A108V + R354K and/or G284L/S + H287D + E289A |
| DS460 | M63Q + L131P + R207N + R325P + E328L | L52F + A108V + R354K and/or G284L/S + H287D + E289A |
| DS461 | M63Q + L131P + R207N + R325P + E328N | L52F + A108V + R354K and/or G284L/S + H287D + E289A |
| DS462 | M63Q + L131P + R207N + R325P | L52F + A108V + R354K and/or G284L/S + H287D + E289A |
| DS463 | M63Q + L131P + R207N + R325A + E328L | L52F + A108V + R354K and/or G284L/S + H287D + E289A |
| DS464 | M63Q + L131P + R207N + R325A + E328N | L52F + A108V + R354K and/or G284L/S + H287D + E289A |
| DS465 | M63Q + L131P + R207N + R325A | L52F + A108V + R354K and/or G284L/S + H287D + E289A |
| DS466 | M63Q + L131P + R207N + E328L | L52F + A108V + R354K and/or G284L/S + H287D + E289A |
| DS467 | M63Q + L131P + R207N + E328N | L52F + A108V + R354K and/or G284L/S + H287D + E289A |
| DS468 | M63Q + L131P + R207N | L52F + A108V + R354K and/or G284L/S + H287D + E289A |
| DS469 | M63Q + L131P + D250V + R325P + E328L | L52F + A108V + R354K and/or G284L/S + H287D + E289A |
| DS470 | M63Q + L131P + D250V + R325P + E328N | L52F + A108V + R354K and/or G284L/S + H287D + E289A |

TABLE 2-continued

Variants of TdT having the amino acid sequence of SEQ ID NO:2, or an amino acid sequence within a specified percent sequence identity thereof, and further including the following Variable Mutations and Optional Constant Mutations (wherein amino acid position numbers are with respect to SEQ ID NO:2).

| Name | Variable Mutations | Optional Constant Mutations |
|---|---|---|
| DS471 | M630 + L131P + D250V + R325P | L52F + A108V + R354K and/or G284L/S + H287D + E289A |
| DS472 | M630 + L131P + D250V + R325A + E328L | L52F + A108V + R354K and/or G284L/S + H287D + E289A |
| DS473 | M630 + L131P + D250V + R325A + E328N | L52F + A108V + R354K and/or G284L/S + H287D + E289A |
| DS474 | M630 + L131P + D250V + R325A | L52F + A108V + R354K and/or G284L/S + H287D + E289A |
| DS475 | M630 + L131P + D250V + E328L | L52F + A108V + R354K and/or G284L/S + H287D + E289A |
| DS476 | M630 + L131P + D250V + E328N | L52F + A108V + R354K and/or G284L/S + H287D + E289A |
| DS477 | M630 + L131P + D250V | L52F + A108V + R354K and/or G284L/S + H287D + E289A |
| DS478 | M630 + L131P + R325P + E328L | L52F + A108V + R354K and/or G284L/S + H287D + E289A |
| DS479 | M630 + L131P + R325P + E328N | L52F + A108V + R354K and/or G284L/S + H287D + E289A |
| DS354 | M630 + L131P + R325P | L52F + A108V + R354K and/or G284L/S + H287D + E289A |
| DS481 | M630 + L131P + R325A + E328L | L52F + A108V + R354K and/or G284L/S + H287D + E289A |
| DS482 | M630 + L131P + R325A + E328N | L52F + A108V + R354K and/or G284L/S + H287D + E289A |
| DS483 | M630 + L131P + R325A | L52F + A108V + R354K and/or G284L/S + H287D + E289A |
| DS484 | M630 + L131P + E328L | L52F + A108V + R354K and/or G284L/S + H287D + E289A |
| DS485 | M630 + L131P + E328N | L52F + A108V + R354K and/or G284L/S + H287D + E289A |
| DS486 | M630 + L131P | L52F + A108V + R354K and/or G284L/S + H287D + E289A |
| DS595 | M630 + R207L + D250V + R325P + E328L | L52F + A108V + R354K and/or G284L/S + H287D + E289A |
| DS596 | M630 + R207L + D250V + R325P + E328N | L52F + A108V + R354K and/or G284L/S + H287D + E289A |
| DS597 | M630 + R207L + D250V + R325P | L52F + A108V + R354K and/or G284L/S + H287D + E289A |
| DS598 | M630 + R207L + D250V + R325A + E328L | L52F + A108V + R354K and/or G284L/S + H287D + E289A |
| DS599 | M630 + R207L + D250V + R325A + E328N | L52F + A108V + R354K and/or G284L/S + H287D + E289A |
| DS600 | M630 + R207L + D250V + R325A | L52F + A108V + R354K and/or G284L/S + H287D + E289A |
| DS601 | M630 + R207L + D250V + E328L | L52F + A108V + R354K and/or G284L/S + H287D + E289A |
| DS602 | M630 + R207L + D250V + E328N | L52F + A108V + R354K and/or G284L/S + H287D + E289A |
| DS603 | M630 + R207L + D250V | L52F + A108V + R354K and/or G284L/S + H287D + E289A |
| DS604 | M630 + R207L + R325P + E328L | L52F + A108V + R354K and/or G284L/S + H287D + E289A |
| DS605 | M630 + R207L + R325P + E328N | L52F + A108V + R354K and/or G284L/S + H287D + E289A |
| DS606 | M630 + R207L + R325P | L52F + A108V + R354K and/or G284L/S + H287D + E289A |
| DS607 | M630 + R207L + R325A + E328L | L52F + A108V + R354K and/or G284L/S + H287D + E289A |
| DS608 | M630 + R207L + R325A + E328N | L52F + A108V + R354K and/or G284L/S + H287D + E289A |
| DS609 | M630 + R207L + R325A | L52F + A108V + R354K and/or G284L/S + H287D + E289A |
| DS610 | M630 + R207L + E328L | L52F + A108V + R354K and/or G284L/S + H287D + E289A |
| DS611 | M630 + R207L + E328N | L52F + A108V + R354K and/or G284L/S + H287D + E289A |
| DS612 | M630 + R207L | L52F + A108V + R354K and/or G284L/S + H287D + E289A |
| DS613 | M630 + R207N + D250V + R325P + E328L | L52F + A108V + R354K and/or G284L/S + H287D + E289A |
| DS614 | M630 + R207N + D250V + R325P + E328N | L52F + A108V + R354K and/or G284L/S + H287D + E289A |
| DS615 | M630 + R207N + D250V + R325P | L52F + A108V + R354K and/or G284L/S + H287D + E289A |
| DS616 | M630 + R207N + D250V + R325A + E328L | L52F + A108V + R354K and/or G284L/S + H287D + E289A |
| DS617 | M630 + R207N + D250V + R325A + E328N | L52F + A108V + R354K and/or G284L/S + H287D + E289A |
| DS618 | M630 + R207N + D250V + R325A | L52F + A108V + R354K and/or G284L/S + H287D + E289A |
| DS619 | M630 + R207N + D250V + E328L | L52F + A108V + R354K and/or G284L/S + H287D + E289A |
| DS620 | M630 + R207N + D250V + E328N | L52F + A108V + R354K and/or G284L/S + H287D + E289A |
| DS621 | M630 + R207N + D250V | L52F + A108V + R354K and/or G284L/S + H287D + E289A |
| DS622 | M630 + R207N + R325P + E328L | L52F + A108V + R354K and/or G284L/S + H287D + E289A |
| DS623 | M630 + R207N + R325P + E328N | L52F + A108V + R354K and/or G284L/S + H287D + E289A |
| DS624 | M630 + R207N + R325P | L52F + A108V + R354K and/or G284L/S + H287D + E289A |
| DS625 | M630 + R207N + R325A + E328L | L52F + A108V + R354K and/or G284L/S + H287D + E289A |
| DS626 | M630 + R207N + R325A + E328N | L52F + A108V + R354K and/or G284L/S + H287D + E289A |
| DS627 | M630 + R207N + R325A | L52F + A108V + R354K and/or G284L/S + H287D + E289A |
| DS628 | M630 + R207N + E328L | L52F + A108V + R354K and/or G284L/S + H287D + E289A |
| DS629 | M630 + R207N + E328N | L52F + A108V + R354K and/or G284L/S + H287D + E289A |
| DS630 | M630 + R207N | L52F + A108V + R354K and/or G284L/S + H287D + E289A |
| DS631 | M630 + D250V + R325P + E328L | L52F + A108V + R354K and/or G284L/S + H287D + E289A |
| DS632 | M630 + D250V + R325P + E328N | L52F + A108V + R354K and/or G284L/S + H287D + E289A |
| DS633 | M630 + D250V + R325P | L52F + A108V + R354K and/or G284L/S + H287D + E289A |
| DS634 | M630 + D250V + R325A + E328L | L52F + A108V + R354K and/or G284L/S + H287D + E289A |
| DS635 | M630 + D250V + R325A + E328N | L52F + A108V + R354K and/or G284L/S + H287D + E289A |
| DS636 | M630 + D250V + R325A | L52F + A108V + R354K and/or G284L/S + H287D + E289A |
| DS637 | M630 + D250V + E328L | L52F + A108V + R354K and/or G284L/S + H287D + E289A |
| DS638 | M630 + D250V + E328N | L52F + A108V + R354K and/or G284L/S + H287D + E289A |
| DS639 | M630 + D250V | L52F + A108V + R354K and/or G284L/S + H287D + E289A |
| DS640 | M630 + R325P + E328L | L52F + A108V + R354K and/or G284L/S + H287D + E289A |
| DS641 | M630 + R325P + E328N | L52F + A108V + R354K and/or G284L/S + H287D + E289A |
| DS642 | M630 + R325P | L52F + A108V + R354K and/or G284L/S + H287D + E289A |
| DS643 | M630 + R325A + E328L | L52F + A108V + R354K and/or G284L/S + H287D + E289A |
| DS644 | M630 + R325A + E328N | L52F + A108V + R354K and/or G284L/S + H287D + E289A |
| DS645 | M630 + R325A | L52F + A108V + R354K and/or G284L/S + H287D + E289A |
| DS646 | M630 + E328L | L52F + A108V + R354K and/or G284L/S + H287D + E289A |
| DS647 | M630 + E328N | L52F + A108V + R354K and/or G284L/S + H287D + E289A |
| DS648 | M630 | L52F + A108V + R354K and/or G284L/S + H287D + E289A |
| DS757 | L131P + R207L + D250V + R325P + E328L | L52F + A108V + R354K and/or G284L/S + H287D + E289A |
| DS758 | L131P + R207L + D250V + R325P + E328N | L52F + A108V + R354K and/or G284L/S + H287D + E289A |
| DS759 | L131P + R207L + D250V + R325P | L52F + A108V + R354K and/or G284L/S + H287D + E289A |

TABLE 2-continued

Variants of TdT having the amino acid sequence of SEQ ID NO:2, or an amino acid sequence within a specified percent sequence identity thereof, and further including the following Variable Mutations and Optional Constant Mutations (wherein amino acid position numbers are with respect to SEQ ID NO:2).

| Name | Variable Mutations | Optional Constant Mutations |
|---|---|---|
| DS760 | L131P + R207L + D250V + R325A + E328L | L52F + A108V + R354K and/or G284L/S + H287D + E289A |
| DS761 | L131P + R207L + D250V + R325A + E328N | L52F + A108V + R354K and/or G284L/S + H287D + E289A |
| DS762 | L131P + R207L + D250V + R325A | L52F + A108V + R354K and/or G284L/S + H287D + E289A |
| DS763 | L131P + R207L + D250V + E328L | L52F + A108V + R354K and/or G284L/S + H287D + E289A |
| DS764 | L131P + R207L + D250V + E328N | L52F + A108V + R354K and/or G284L/S + H287D + E289A |
| DS765 | L131P + R207L + D250V | L52F + A108V + R354K and/or G284L/S + H287D + E289A |
| DS766 | L131P + R207L + R325P + E328L | L52F + A108V + R354K and/or G284L/S + H287D + E289A |
| DS767 | L131P + R207L + R325P + E328N | L52F + A108V + R354K and/or G284L/S + H287D + E289A |
| DS768 | L131P + R207L + R325P | L52F + A108V + R354K and/or G284L/S + H287D + E289A |
| DS769 | L131P + R207L + R325A + E328L | L52F + A108V + R354K and/or G284L/S + H287D + E289A |
| DS770 | L131P + R207L + R325A + E328N | L52F + A108V + R354K and/or G284L/S + H287D + E289A |
| DS771 | L131P + R207L + R325A | L52F + A108V + R354K and/or G284L/S + H287D + E289A |
| DS772 | L131P + R207L + E328L | L52F + A108V + R354K and/or G284L/S + H287D + E289A |
| DS773 | L131P + R207L + E328N | L52F + A108V + R354K and/or G284L/S + H287D + E289A |
| DS774 | L131P + R207L | L52F + A108V + R354K and/or G284L/S + H287D + E289A |
| DS775 | L131P + R207N + D250V + R325P + E328L | L52F + A108V + R354K and/or G284L/S + H287D + E289A |
| DS776 | L131P + R207N + D250V + R325P + E328N | L52F + A108V + R354K and/or G284L/S + H287D + E289A |
| DS777 | L131P + R207N + D250V + R325P | L52F + A108V + R354K and/or G284L/S + H287D + E289A |
| DS778 | L131P + R207N + D250V + R325A + E328L | L52F + A108V + R354K and/or G284L/S + H287D + E289A |
| DS779 | L131P + R207N + D250V + R325A + E328N | L52F + A108V + R354K and/or G284L/S + H287D + E289A |
| DS780 | L131P + R207N + D250V + R325A | L52F + A108V + R354K and/or G284L/S + H287D + E289A |
| DS781 | L131P + R207N + D250V + E328L | L52F + A108V + R354K and/or G284L/S + H287D + E289A |
| DS782 | L131P + R207N + D250V + E328N | L52F + A108V + R354K and/or G284L/S + H287D + E289A |
| DS783 | L131P + R207N + D250V | L52F + A108V + R354K and/or G284L/S + H287D + E289A |
| DS784 | L131P + R207N + R325P + E328L | L52F + A108V + R354K and/or G284L/S + H287D + E289A |
| DS785 | L131P + R207N + R325P + E328N | L52F + A108V + R354K and/or G284L/S + H287D + E289A |
| DS786 | L131P + R207N + R325P | L52F + A108V + R354K and/or G284L/S + H287D + E289A |
| DS787 | L131P + R207N + R325A + E328L | L52F + A108V + R354K and/or G284L/S + H287D + E289A |
| DS788 | L131P + R207N + R325A + E328N | L52F + A108V + R354K and/or G284L/S + H287D + E289A |
| DS789 | L131P + R207N + R325A | L52F + A108V + R354K and/or G284L/S + H287D + E289A |
| DS790 | L131P + R207N + E328L | L52F + A108V + R354K and/or G284L/S + H287D + E289A |
| DS791 | L131P + R207N + E328N | L52F + A108V + R354K and/or G284L/S + H287D + E289A |
| DS792 | L131P + R207N | L52F + A108V + R354K and/or G284L/S + H287D + E289A |
| DS793 | L131P + D250V + R325P + E328L | L52F + A108V + R354K and/or G284L/S + H287D + E289A |
| DS794 | L131P + D250V + R325P + E328N | L52F + A108V + R354K and/or G284L/S + H287D + E289A |
| DS795 | L131P + D250V + R325P | L52F + A108V + R354K and/or G284L/S + H287D + E289A |
| DS796 | L131P + D250V + R325A + E328L | L52F + A108V + R354K and/or G284L/S + H287D + E289A |
| DS797 | L131P + D250V + R325A + E328N | L52F + A108V + R354K and/or G284L/S + H287D + E289A |
| DS798 | L131P + D250V + R325A | L52F + A108V + R354K and/or G284L/S + H287D + E289A |
| DS799 | L131P + D250V + E328L | L52F + A108V + R354K and/or G284L/S + H287D + E289A |
| DS800 | L131P + D250V + E328N | L52F + A108V + R354K and/or G284L/S + H287D + E289A |
| DS801 | L131P + D250V | L52F + A108V + R354K and/or G284L/S + H287D + E289A |
| DS802 | L131P + R325P + E328L | L52F + A108V + R354K and/or G284L/S + H287D + E289A |
| DS803 | L131P + R325P + E328N | L52F + A108V + R354K and/or G284L/S + H287D + E289A |
| DS804 | L131P + R325P | L52F + A108V + R354K and/or G284L/S + H287D + E289A |
| DS805 | L131P + R325A + E328L | L52F + A108V + R354K and/or G284L/S + H287D + E289A |
| DS806 | L131P + R325A + E328N | L52F + A108V + R354K and/or G284L/S + H287D + E289A |
| DS807 | L131P + R325A | L52F + A108V + R354K and/or G284L/S + H287D + E289A |
| DS808 | L131P + E328L | L52F + A108V + R354K and/or G284L/S + H287D + E289A |
| DS809 | L131P + E328N | L52F + A108V + R354K and/or G284L/S + H287D + E289A |
| DS810 | L131P | L52F + A108V + R354K and/or G284L/S + H287D + E289A |
| DS921 | R207L + D250V + R325P | L52F + A108V + R354K and/or G284L/S + H287D + E289A |
| DS922 | R207L + D250V + R325A + E328L | L52F + A108V + R354K and/or G284L/S + H287D + E289A |
| DS923 | R207L + D250V + R325A + E328N | L52F + A108V + R354K and/or G284L/S + H287D + E289A |
| DS924 | R207L + D250V + R325A | L52F + A108V + R354K and/or G284L/S + H287D + E289A |
| DS925 | R207L + D250V + E328L | L52F + A108V + R354K and/or G284L/S + H287D + E289A |
| DS926 | R207L + D250V + E328N | L52F + A108V + R354K and/or G284L/S + H287D + E289A |
| DS927 | R207L + D250V | L52F + A108V + R354K and/or G284L/S + H287D + E289A |
| DS928 | R207L + R325P + E328L | L52F + A108V + R354K and/or G284L/S + H287D + E289A |
| DS929 | R207L + R325P + E328N | L52F + A108V + R354K and/or G284L/S + H287D + E289A |
| DS930 | R207L + R325P | L52F + A108V + R354K and/or G284L/S + H287D + E289A |
| DS931 | R207L + R325A + E328L | L52F + A108V + R354K and/or G284L/S + H287D + E289A |
| DS932 | R207L + R325A + E328N | L52F + A108V + R354K and/or G284L/S + H287D + E289A |
| DS933 | R207L + R325A | L52F + A108V + R354K and/or G284L/S + H287D + E289A |
| DS934 | R207L + E328L | L52F + A108V + R354K and/or G284L/S + H287D + E289A |
| DS935 | R207L + E328N | L52F + A108V + R354K and/or G284L/S + H287D + E289A |
| DS936 | R207L | L52F + A108V + R354K and/or G284L/S + H287D + E289A |
| DS937 | R207N + D250V + R325P + E328L | L52F + A108V + R354K and/or G284L/S + H287D + E289A |
| DS938 | R207N + D250V + R325P + E328N | L52F + A108V + R354K and/or G284L/S + H287D + E289A |
| DS939 | R207N + D250V + R325P | L52F + A108V + R354K and/or G284L/S + H287D + E289A |
| DS940 | R207N + D250V + R325A + E328L | L52F + A108V + R354K and/or G284L/S + H287D + E289A |
| DS941 | R207N + D250V + R325A + E328N | L52F + A108V + R354K and/or G284L/S + H287D + E289A |
| DS942 | R207N + D250V + R325A | L52F + A108V + R354K and/or G284L/S + H287D + E289A |

TABLE 2-continued

Variants of TdT having the amino acid sequence of SEQ ID NO:2, or an amino acid sequence within a specified percent sequence identity thereof, and further including the following Variable Mutations and Optional Constant Mutations (wherein amino acid position numbers are with respect to SEQ ID NO:2).

| Name | Variable Mutations | Optional Constant Mutations |
|---|---|---|
| DS943 | R207N + D250V + E328L | L52F + A108V + R354K and/or G284L/S + H287D + E289A |
| DS944 | R207N + D250V + E328N | L52F + A108V + R354K and/or G284L/S + H287D + E289A |
| DS945 | R207N + D250V | L52F + A108V + R354K and/or G284L/S + H287D + E289A |
| DS946 | R207N + R325P + E328L | L52F + A108V + R354K and/or G284L/S + H287D + E289A |
| DS947 | R207N + R325P + E328N | L52F + A108V + R354K and/or G284L/S + H287D + E289A |
| DS948 | R207N + R325P | L52F + A108V + R354K and/or G284L/S + H287D + E289A |
| DS949 | R207N + R325A + E328L | L52F + A108V + R354K and/or G284L/S + H287D + E289A |
| DS950 | R207N + R325A + E328N | L52F + A108V + R354K and/or G284L/S + H287D + E289A |
| DS951 | R207N + R325A | L52F + A108V + R354K and/or G284L/S + H287D + E289A |
| DS952 | R207N + E328L | L52F + A108V + R354K and/or G284L/S + H287D + E289A |
| DS953 | R207N + E328N | L52F + A108V + R354K and/or G284L/S + H287D + E289A |
| DS954 | R207N | L52F + A108V + R354K and/or G284L/S + H287D + E289A |
| DS955 | D250V + R325P + E328L | L52F + A108V + R354K and/or G284L/S + H287D + E289A |
| DS956 | D250V + R325P + E328N | L52F + A108V + R354K and/or G284L/S + H287D + E289A |
| DS957 | D250V + R325P | L52F + A108V + R354K and/or G284L/S + H287D + E289A |
| DS958 | D250V + R325A + E328L | L52F + A108V + R354K and/or G284L/S + H287D + E289A |
| DS959 | D250V + R325A + E328N | L52F + A108V + R354K and/or G284L/S + H287D + E289A |
| DS960 | D250V + R325A | L52F + A108V + R354K and/or G284L/S + H287D + E289A |
| DS961 | D250V + E328L | L52F + A108V + R354K and/or G284L/S + H287D + E289A |
| DS962 | D250V + E328N | L52F + A108V + R354K and/or G284L/S + H287D + E289A |
| DS963 | D250V | L52F + A108V + R354K and/or G284L/S + H287D + E289A |
| DS964 | R325P + E328L | L52F + A108V + R354K and/or G284L/S + H287D + E289A |
| DS965 | R325P + E328N | L52F + A108V + R354K and/or G284L/S + H287D + E289A |
| DS966 | R325P | L52F + A108V + R354K and/or G284L/S + H287D + E289A |
| DS967 | R325A + E328L | L52F + A108V + R354K and/or G284L/S + H287D + E289A |
| DS968 | R325A + E328N | L52F + A108V + R354K and/or G284L/S + H287D + E289A |
| DS969 | R325A | L52F + A108V + R354K and/or G284L/S + H287D + E289A |
| DS970 | E328L | L52F + A108V + R354K and/or G284L/S + H287D + E289A |
| DS971 | E328N | L52F + A108V + R354K and/or G284L/S + H287D + E289A |
| DS919 | R207L + D250V + R325P + E328L | L52F + A108V + R354K and/or G284L/S + H287D + E289A |
| DS920 | R207L + D250V + R325P + E328N | L52F + A108V + R354K and/or G284L/S + H287D + E289A |

According to some embodiments, a variant of TdT has a substitution or combination of substitutions described above and has an amino acid sequence within at least 80% identity with SEQ ID NO:2 or with a functionally equivalent sequence (such as, SEQ ID NOs:11, 13, 15, 17, 19, 21, 23, 25, 27, 29, 31, 33 or 35); in some embodiments, such amino acid sequence is within at least 85%, 90%, 95%, 96%, 97%, 98%, or 99% identity with SEQ ID NO:2 or functionally equivalent sequence (such as, SEQ ID NOs:11, 13, 15, 17, 19, 21, 23, 25, 27, 29, 31, 33 or 35).

Additional Modifications

In an embodiment, the variant of TdT further includes any type of tagging peptide in its N-terminal, C-terminal or both extremity, such as a His-tag sequence. Said tagging peptide could be used for purification, identification, increasing expression, secretability or increasing catalytic activity. It will be understood that such different tags are extensively described in the literature and thus all tag known to a skilled person are covered by the present invention.

The variants of the invention can also include one or more exogenous or heterologous features at the N- and/or C-terminal regions of the protein for use, e.g., in the purification of the recombinant polymerase.

The variant of the invention may further comprise a substitution of residues between positions C378 to L406, wherein the positions are numbered by reference to the amino acid sequence set forth in SEQ ID NO1, or functionally equivalent residues, by residues H363 to C390 of the Polµ polymerase of sequence SEQ ID NO:3, wherein the positions are numbered by reference to the amino acid sequence set forth in SEQ ID NO:3 or functionally equivalent residues.

Advantageously, the variant of TdT comprises at least the amino acid sequence SEQ ID NO:2, 11, 13, 15, 17, 19, 21, 23, 25, 27, 29, 31, 33 or 35, with the disclosed substitution(s) and percent sequence identity values.

Nucleic Acids, Expression Cassette, Vector

It is also the purpose of the invention to provide a nucleic acid molecule encoding a variant of the invention. As used herein, the term "nucleic acid", "nucleic sequence," "polynucleotide", "oligonucleotide" and "nucleotide sequence" are used interchangeably and refer to a sequence of deoxyribonucleotides and/or ribonucleotides. In one embodiment, the nucleic acid is a DNA. In an alternative embodiment, the nucleic acid is RNA. In an alternative embodiment, the nucleic acid is XNA.

The nucleic acids can be in single stranded form or in duplex form or a mixture of the two. It can be of recombinant, artificial and/or synthetic origin and it can comprise modified nucleotides. Such modifications could be natural modifications such as epigenetic modifications, or unnatural modification such as labels, modified bond, a modified purine or pyrimidine base, or a modified sugar. In one embodiment, nucleic acid molecules are DNA, RNA or XNA bearing naturally occurring epigenetic modifications such as methylation, hydfroxymethylation, formylation or 5-carboxylation. In one embodiment, nucleic acid molecules are DNA, RNA or XNA bearing unnaturally occurring modifications such as fluorescent tag, fluorescent label, interaction groups.

The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding a TdT variant as defined above. Such stringent conditions include incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding a TdT variant of the invention, wherein the sequence of said nucleic acids, or a portion of said sequence at least, has been engineered using optimized codon usage.

Alternatively, the nucleic acids according to the invention may be deduced from the sequence of the TdT variant according to the invention and codon usage may be adapted according to the host cell in which the nucleic acids shall be transcribed. These steps may be carried out according to methods well known to one skilled in the art and some of which are described in the reference manual Sambrook et al. (Sambrook et al., 2001).

In one embodiment, nucleic acid molecules are polymeric molecules having length of more than 50, 100, 200, 300, 400, 500, 600, 700, 800, 900, 1000, 2 000, 3 000, 4 000, 5 000, 6 000, 7 000, 8 000, 9 000, 10 000, 15 000, 20 000, 30 000, 40 000, 50 000 or 100 000 nucleotides.

Nucleic acids of the invention may further comprise additional nucleotide sequences, such as regulatory regions, i.e., promoters, enhancers, silencers, terminators, signal peptides and the like that can be used to cause or regulate expression of the polypeptide in a selected host cell or system.

The present invention further relates to an expression cassette comprising a nucleic acid according to the invention operably linked to one or more control sequences that direct the expression of said nucleic acid in a suitable host cell. Typically, the expression cassette comprises, or consists of, a nucleic acid according to the invention operably linked to a control sequence such as transcriptional promoter and/or transcription terminator. The control sequence may include a promoter that is recognized by a host cell or an in vitro expression system for expression of a nucleic acid encoding a TdT variant of the present invention. The promoter contains transcriptional control sequences that mediate the expression of the enzyme. The promoter may be any polynucleotide that shows transcriptional activity in the host cell including mutant, truncated, and hybrid promoters, and may be obtained from genes encoding extracellular or intracellular polypeptides either homologous or heterologous to the host cell. The control sequence may also be a transcription terminator, which is recognized by a host cell to terminate transcription. The terminator is operably linked to the 3'-terminus of the nucleic acid encoding the esterase. Any terminator that is functional in the host cell may be used in the present invention. Typically, the expression cassette comprises, or consists of, a nucleic acid according to the invention operably linked to a transcriptional promoter and a transcription terminator.

The invention also relates to a vector comprising a nucleic acid or an expression cassette as defined above.

The term "vector" refers to DNA molecule used as a vehicle to transfer recombinant genetic material into a host cell. The major types of vectors are plasmids, bacteriophages, viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide. Generally, the regulatory elements that are present in an expression vector include a transcriptional promoter, a ribosome binding site, a terminator, and optionally present operator. An expression vector can also contain an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. The choice of the vector will typically depend on the compatibility of the vector with the host cell into which the vector is to be introduced.

It is another object of the invention to provide a host cell comprising a nucleic acid, an expression cassette or a vector as described above. The present invention thus relates to the use of a nucleic acid, expression cassette or vector according to the invention to transform, transfect or transduce a host cell. The choice of the vector will typically depend on the compatibility of the vector with the host cell into which it must be introduced.

According to the invention, the host cell may be transformed, transfected or transduced in a transient or stable manner. The expression cassette or vector of the invention is introduced into a host cell so that the cassette or vector is maintained as a chromosomal integrant or as a self-replicating extra-chromosomal vector. The term "host cell" also encompasses any progeny of a parent host cell that is not identical to the parent host cell due to mutations that occur during replication. The host cell may be any cell useful in the production of a variant of the present invention, e.g., a prokaryote or a eukaryote. The prokaryotic host cell may be any Gram-positive or Gram-negative bacterium. The host cell may also be an eukaryotic cell, such as a yeast, fungal, mammalian, insect or plant cell.

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation, liposome-mediated transformation, Optionally, more than one copy of a nucleic acid, cassette or vector of the present invention may be inserted into a host cell to increase production of the variant.

Modified Nucleotides

According to the invention, the variants of TdT are able to incorporate modified nucleotides, such as modified 3'O— nucleotides, including 3'O-blocked nucleotides.

In the context of the invention, the expression "Modified Nucleotide" refers to a molecule containing a nucleoside (i.e. a base attached to a deoxyribose or ribose sugar molecule) bound to three phosphate groups which has at least one additional group on one of its extremity: 2', 3', 5' or base. Said additional group blocks further addition of nucleotides by preventing the formation of any phosphodiester bond (3'O-modification, 2' or 2'O modifications) or by sterically preventing the polymerase to attach to any nucleic acid fragments that comprises on its 3' extremity such modified nucleotide (5' or base modification). Furthery, said additional group has advantageously a reversible nature allowing that group to be removed through a specific cleaving reaction.

Nucleosides or nucleotide triphosphates include deoxyadenosine triphosphate (dATP), deoxyguanosine triphosphate (dGTP), deoxycytidine triphosphate (dCTP) or deoxythymidine triphosphate (dTTP) for examples of nucleotide containing deoxyribose. Adenosine triphosphate (ATP), guanosine triphosphate (GTP), cytidine triphosphate (CTP) or uridine triphosphate (UTP) are further examples of nucleotide triphosphates containing ribose. Other types of nucleosides may be bound to three phosphates to form nucleotide triphosphates, such as naturally occurring modified nucleosides and artificial nucleosides.

In a particular embodiment, the modified nucleotide is a 3'O-blocked nucleotide, which comprises a group reversibly attached to the 3' end of the nucleotide triphosphate to prevent further nucleotide addition. Said group could have diverse chemical natures, such as azidomethyl, aminoxy, and allyl.

Advantageously, the modified nucleotide is selected from a 3'-O—NH$_2$-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

wherein —Z is any of —C(R')2-0-R", —C(R')2-N(R")2, —C(R')2-N(H)R", —C(R')2-S—R" and —C(R')2-F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')2 represents an alkylidene group of formula =C(R''')2 wherein each R''' may be the same or different and is selected from the group comprising hydrogen and halogen atoms and alkyl groups, with the proviso that in some embodiments the alkyl of each R''' has from 1 to 3 carbon atoms; and wherein the molecule may be reacted to yield an intermediate in which each R" is exchanged for H or, where Z is —(R')2-F, the F is exchanged for OH, SH or NH2, preferably OH, which intermediate dissociates under aqueous conditions to afford a molecule with a free 3'-OH; with the proviso that where Z is —C(R')2-S—R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, —Z of the modified nucleotide or nucleoside is of formula —C(R')$_2$—N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less.

In a further particular embodiment, "3'O modified nucleotide" refers to nucleotide triphosphate bearing at the 3' extremity either a 3'-O-methyl, 3'-azido, 3'-O-azidomethyl, 3'-O-amino, 3'-aminoxy or 3'-O-allyl group. In a further embodiment, the 3'-blocked nucleotide triphosphate is blocked by either a 3'-O-azidomethyl, 3'-aminoxy or 3'-O-allyl group. In other embodiments, "3'O modified nucleotide" refers to nucleotide triphosphate bearing at the 3' extremity either esters, ethers, carbonitriles, phosphates, carbonates, carbamates, hydroxylamine, borates, nitrates, sugars, phosphoramide, phosphoramidates, phenylsulfenates, sulfates, sulfones or amino acids. In some embodiments, the foregoing 3'-O-blocking groups have a molecule weight of 100 or less.

In another embodiments, 3'-O-blocking groups of the invention include methyl, 3'-O-(2-nitrobenzyl), allyl, amine, azidomethyl, tert-butoxy ethoxy, or propargyl.

In further particular embodiment, "3'O modified nucleotide" refers to a nucleotide triphosphate having a terminator effector modifying group such as those described in WO2016034807.

Interestingly, the variants of the invention exhibit an increased affinity for modified nucleotides, as compared to wild type TdT, and thereby an increased ability to incorporate such modified nucleotide in a nucleic acid sequence during nucleic acid synthesis. More particularly, the variants of the invention are able to use and incorporate modified 3'O— nucleotides (and more particularly, 3'O-blocked nucleotide) in nucleic acid sequence, which is not possible with wild type TdT (see Knapp et al. Chem. Eur. J., 2011, 17:2903).

According to a particular aspect, the invention relates to variants of TdT able to work with modified nucleotides in a nucleic acids enzymatic synthesis process, particularly with 3'O-modified nucleotides (e.g., 3'O-blocked nucleotide), and having the ability to produce long length nucleic acid molecules or derivative of nucleic acid molecules.

Enzymatic Synthesis of Nucleic Acid

It is the purpose of the present invention to provide variants of TdT that may be used for the synthesis of nucleic acid, such as described in Ybert et al, WO2015/159023; Jensen et al, Biochemistry, 57: 1821-1832 (2018); Hiatt et al, U.S. Pat. No. 5,808,045. More particularly, it is the purpose of the present invention to provide variants of TdT suitable to add modified nucleotides to an initiating nucleic acid strand. The blocking group may be then removed for allowing a new addition of modified nucleotide.

According to the invention, by use of a variant of the invention, it is possible to implement successive cycles comprising additions and deprotections. This process will therefore allow by multiple cycles of addition of a reversible modified nucleotide and further removal of the blocking group to allow the controlled extension of an initiating nucleic acid strand into a defined sequence.

The present invention contemplates the use of modified TdT according to the present invention in any enzymatic nucleic acid synthesis process.

It is thus an object of the present invention to provide a method of synthesizing a polynucleotide having a predetermined sequence, comprising the steps of:
  a) providing an initiator having a 3'-terminal nucleotide having a free 3'-hydroxyl;
  b) repeating cycles of (i) contacting under elongation conditions the initiator or elongated fragments having free 3'-O-hydroxyls with a 3'-O-blocked nucleoside triphosphate and a TdT variant of the present invention, so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until the polynucleotide is formed.

It is also the purpose of the present invention to provide a process for synthesizing a nucleic acid molecule without template, comprising a step of contacting a nucleic acid primer with both at least one nucleotide, such as at least one 3'O-modified nucleotide, and a variant of the invention.

The present invention contemplates the concept of enzymatic nucleic acids synthesis process. In such process, nucleic acids molecules are de novo synthesized in absence of any template strand. Accordingly, ordered sequence of nucleotides are coupled to an initiator nucleic acid fragment with the help of the variant of the invention. It will be understood that quantitative coupling and more generally high coupling efficiency of each nucleotide to the growing nucleic acid chain is of great importance. It will also be understood that non-terminator nucleotides, such as natural nucleotides or permanent labeled nucleotides, will not permit any control over the sequence synthesized and will result, for example, in uncontrolled and undesired poly-additions.

In some embodiments, the method of synthesizing a polynucleotide comprises the steps of (a) providing an initiator having a free 3'-hydroxyl; (b) reacting under extension conditions the initiator or an extension intermediate having a free 3'-hydroxyl with a variant TdT of the invention in the presence of a 3'-O-blocked nucleoside triphosphate to produce a 3'-O-blocked extension intermediate; (c) deblocking the extension intermediate to produce an extension intermediate with a free 3'-hydroxyl; and (d) repeating steps (b) and (c) until the polynucleotide is synthesized.

In some embodiments, the method of synthesizing a polynucleotide comprises the steps of (a) providing an initiator attached to a solid support, the intiator being an oligonucleotide having a free 3'-hydroxyl; (b) reacting under extension conditions the initiator or an extension intermediate having a free 3'-hydroxyl with a variant TdT of the invention in the presence of a 3'-O-blocked nucleoside triphosphate to produce a 3'-O-blocked extension intermediate; (c) washing the solid support to remove unincorporated 3'-O-blocked nucleoside triphosphate; (d) deblocking the extension intermediate by exposing the solid support to a deblocking agent to produce an extension intermediate having a free 3'-hydroxyl; and (e) repeating steps (b) and (d) until the polynucleotide is synthesized. The method may include a further step of cleaving the completed polynucleotide from the solid support.

In some embodiments, for TdT catalyzed addition reactions, the enzymatic conditions may contain from about 0.20 and about 200 µM of the nucleotide having the removable blocking moiety protecting the 3'-hydroxyl and from about 0.20 to 200 µM of free and unmodified 3'-hydroxyls derived from the initiating substrate. In some embodiments, the reaction buffer contains from about 10 to about 500 mM potassium cacodylate buffer (pH between 6.5 and 7.5). and from about 0.01 to about 10 mM of a divalent cation (e.g. $CoCl_2$ or $MnCl_2$). Other buffer compositions and components may be suitable for particular desired embodiment of the present invention.

In the context of the invention, the expression "cleaving reaction" refers to any action of substance or physical conditions, which is able to cleave the additional group previously described on reversible modified nucleotides. A person skilled in the art is able to determine a cleaving reaction for any previously listed group.

In one embodiment, the cleaving agent is a chemical cleaving agent. In an alternative embodiment, the cleaving agent is an enzymatic cleaving agent.

It will be understood by the person skilled in the art that the selection of cleaving agent is dependent on the type of 3'-nucleotide blocking group used. For example, tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiment, the cleaving reaction is involving: TCEP, a palladium complex or sodium nitrite.

In particular embodiments, the cleaving reaction is performed in the presence of additional components such as denaturant (urea, guanidinium chloride, formamide or betaine for example). In a further embodiment, the cleavage reaction is performed with one or more buffers. It will be understood by the person skilled in the art that the choice of buffer is dependent on the exact mechanism of reaction.

The present invention relates to variants of TdT with the capacity to incorporate, in a quantitative way, modified nucleotides. By "quantitative way" or "quantitative reaction", it is meant a reaction that goes to completion, i.e. in which reactants are totally converted into the product. Polymerase that incorporates in a quantitative way reversible modified nucleotide is a polymerase able to elongate every fragment of nucleic acid with all the nucleotides available leading to the conversion of all the initiating fragments of length n, to fragments of length n+1.

As used herein, "initiating fragment" refers to a short oligonucleotide sequence with a free 3'-end, which can be further elongated. In one embodiment, the initiating fragment is a DNA initiating fragment. In an alternative embodiment, the initiating fragment is an RNA initiating fragment.

In one embodiment, the initiating fragment possesses between 3 and 100 nucleotides, in particular between 3 and 20 nucleotides.

In one embodiment, the initiating fragment is single-stranded. In an alternative embodiment, the initiating fragment is double-stranded.

In one embodiment, the initiating fragment is immobilized on a solid support. The initiating fragment may be attached with various method to a solid support resulting in a stable under the various enzymatic or synthesis reaction conditions that the fragment will undergo.

In one embodiment, the initiating fragment is immobilized on a solid support via a reversible interacting moiety, such as a chemically-cleavable linker, an antibody/immunogenic epitope, a biotin/biotin-binding protein or gluta-thione-GST tag. In a further embodiment, the initiating fragment is immobilized on a solid support via a chemically-cleavable linker, such as a disulfide, allyl, or azide-masked hemiaminal ether linker.

In an initiating fragment, the immobilized part contains at least one restriction site. The use of restriction enzymes and restriction sites to selectively hydrolyze nucleic acids chain at a specific site is describe in the literature. Any skilled person will be able to choose the appropriate restriction enzyme that will match the initiating fragment cleaving site sequence.

In an alternative embodiment, the initiating fragment contains at least one uridine. Treatment with uracil-DNA glycosylase (UDG) generates an abasic site. Treatment on an appropriate substrate with an apurinic/apyrimidinic (AP) site endonuclease will extract the nucleic acid strand.

Applications

Described herein is the use of variants of TdT to be used for nucleic acid synthesis, oligonucleotide synthesis, probe synthesis, tagging, nucleic acid amplification, aptamers, therapeutic nucleic acid molecules, drug target discovery and validation, disease diagnosis, metabolic engineering, data storage, crops improvement, library design, sequencing pools, nucleic acid labeling or attachment or any other application that is involving nucleic acid molecules.

Production of Variant TdTs

Variants of the invention may be produced by mutating known reference or wild type TdT-coding polynucleotides, then expressing it using conventional molecular biology techniques.

For example, the mouse TdT gene (SEQ ID NO:1) may be assembled from synthetic fragments using conventional molecular biology techniques, e.g. using protocols described by Stemmer et al, Gene, 164: 49-53 (1995); Kodumal et al, Proc. Natl. Acad. Sci., 101: 15573-15578 (2004); or the like, or it may be directly cloned from mouse cells using protocols described by Boule et al, Mol. Biotechnology, 10: 199-208 (1998), or Bentolila et al, EMBO J., 14: 4221-4229 (1995); or the like.

For example, an isolated TdT gene may be inserted into an expression vector, such as pET32 (Novagen) to give a vector pCTdT which then may be used to make and express variant TdT proteins using conventional protocols. Vectors with the correct sequence may be transformed in E. coli producer strains.

Transformed strains are cultured using conventional techniques to pellets from which TdT protein is extracted. For example, previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1h to 1h30 at 10,000 rpm. Centrifugate is pass through a 0.2 µm filter to remove any debris before column purification.

TdT protein may be purified from the centrifugate in a one-step affinity procedure. For example, Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH4]2SO4). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDSPAGE gels.

Kits, Enzyme and Nucleotide Composition

A particular aspect of the invention is relative to the composition and the use of kits comprising a variant of TdT according to the invention, or to any particular aspect of the present invention, with optionally any combination of one or more components selected from: an initiating fragment, one or more reversible terminator nucleotides, additional enzyme and reagents used in a cleaving reaction. Said kits can be used in a method of enzymatic nucleic acid synthesis.

The present invention covers the composition of matter comprising variants of TdT according to the invention, or to any particular aspect of the present invention, with reversible modified nucleotide in a mix with appropriate buffer and ratio concentration.

EXAMPLES

Example 1—Generation, Expression and Purification of Variants of TdT According to the Invention Expression Strain Generation The TdT mouse gene has been generated from the pET28 plasmid described in [Boulé et al., 1998, Mol. Biotechnol. 10, 199-208]. Sequence SEQ ID No 4 (Tag TdT) has been amplified by using the following primers:

```
T7-pro:
                                     (SEQ ID NO: 5)
TAATACGACTCACTATAGGG T7-ter:
                                     (SEQ ID NO: 6)
GCTAGTTATTGCTCAGCGG
``` through standard molecular biology techniques. The sequence is then cloned into plasmid pET32 backbone to give the new pCTdT plasmid.

After sequencing pCTdT is transformed into commercial E. coli cells, BL21 (DE3, from Novagen). Growing colonies on plate with kanamycin are isolated and named Ec-CTdT.

Polymerase Variants Generation

The pCTdT vector is used as starting vector. Specific primers comprising one or several point mutations have been generated from Agilent online software (http://www.genomics.agilent.com:80/primerDesignProgram.jsp). The commercially available kit QuickChange II (Agilent) has been used to generate the desired modified polymerase comprising the targeted mutations. Experimental procedure has followed the supplier's protocol. After generation of the different vectors, each of them have been sequenced. Vectors with the correct sequence have been transformed in E. coli producer strains, as described before. Clones able to grow on kanamycin LB-agar plates are isolated.

Expression

The Ec-CTdT and Ec-DSi or Ec-DSi' strains have been used for inoculating 250 mL erlens with 50 mL of LB media supplemented with appropriate amount of kanamycin. After overnight growth at 37° C., appropriate volumes of these pre-cultures have been used to inoculate 5 L erlens with 2 L LB media with kanamycin. The initial OD for the 5 L cultures is chosen to be 0.01. The erlens are put at 37° C. under strong agitation and the OD of the different cultures are regularly checked. After reaching an OD comprised between 0.6 and 0.9 each erlen is supplemented by the addition of mL of 1M IPTG (Isopropyl β-D-1-thiogalactopyranoside, Sigma). The erlens are put back to agitation under a controlled temperature of 37° C. After overnight expression, the cells are harvested in several pellets. Pellets expressing the same variants are pooled and stored at −20° C., eventually for several months.

Extraction

Previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1h to 1h30 at 10,000 rpm. Centrifugate is pass through a 0.2 µm filter to remove any debris before column purification.

Purification

A one-step affinity procedure is used to purify the produced and extracted polymerase enzymes. A Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH$_4$]$_2$SO$_4$). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDS-PAGE gels.

Results are presented by FIG. 1. The gel shows, for each TdT (both variants and wild-type), the column flowthrough (FT) and the different fractions F1 to F4, corresponding to the elution peaks. A molecular weight marker (M) was also loaded in the gel. FIG. 1 shows that the variants of TdT according to the invention present a high purity level (about 90%) and a good expression as compared to TdT wild-type (see columns F2 and/or F3).

Example 2—Evaluation of the Activity of Variants of TdT with Fluorescent Primers Activity Test Elongation performance of TdT variants of SEQ ID NO: 2: DS11 (M63R+L131P+C173R+R207L+R325P+E328N) DS29 (M63R+L131P+C173R+R207N+R325P+E328N), DS173 (M63R+C173R+R207L+R325P+E328N), DS659 (L131P+C173R+R207L+R325P+E328N), DS874 (C173G+R207L+R325P+E328L) generated, expressed and purified according to example 1 is evaluated through the following assay. All the results are compared with each other and with the wild type TdT enzyme (SEQ ID No 1) and to a control tube lacking any polymerase enzyme.

TABLE 7

| Activity test | | |
|---|---|---|
| Reagent | Concentration | Volume |
| H$_2$O | — | 12 µL |
| Activity Buffer | 10× | 2 µL |
| dNTP | 250 µM | 2 µL |
| Purified enzyme | 20 µM | 2 µL |
| Fluorescent primer DNA | 500 nM | 2 µL |

The Activity buffer comprises, for example, TdT reaction buffer (available from New England Biolabs) supplemented with CoCl$_2$. Primer used is the following:

(SEQ ID NO: 7)
5'-AAAAAAAAAAAAAAGGGG-3'

The primer has also an ATTO fluorescent dye on the 5' extremity.

Nucleotides used (noted as dNTP in table 7) are 3'-O-amino-2',3'-dideoxynucleotides-5'-triphosphate (ONH$_2$, Firebird Biosciences) such as 3'-O-amino-2',3'-dideoxyadenosine-5'-triphosphate for example.

For each different variant tested, one tube is used for the reaction. The reagents are added in the tube, starting from water, and then in the order of Table 7. After 30 min at 37° C. the reaction is stopped by addition of formamide (Sigma).

Analysis

The analysis is involving polyacrylamide gel analysis. Samples from activity test are analyzed through polyacrylamide 16% (biorad) denaturing gel. Gels are made just before the analysis by pouring polyacrylamide inside glass plates and let it polymerize. The gel inside the glass plates is mounted on an adapted tank filed with TBE buffer (Sigma) for the electrophoresis step. The samples to be analyzed are loaded on the top of the gel. A tension of 500 to 2,000V is applied between the top and bottom of the gel for 3 to 6h at room temperature. Once migrated according to the sample target size, system is dismounted, and gel fluorescence is scanned through the use of Typhoon instrument (GE Life Sciences). After image acquisition, ImageJ software (imagej.nih.gov/ij/) is used to analyze the percentage of incorporation of the modified nucleotides.

Figure 2:
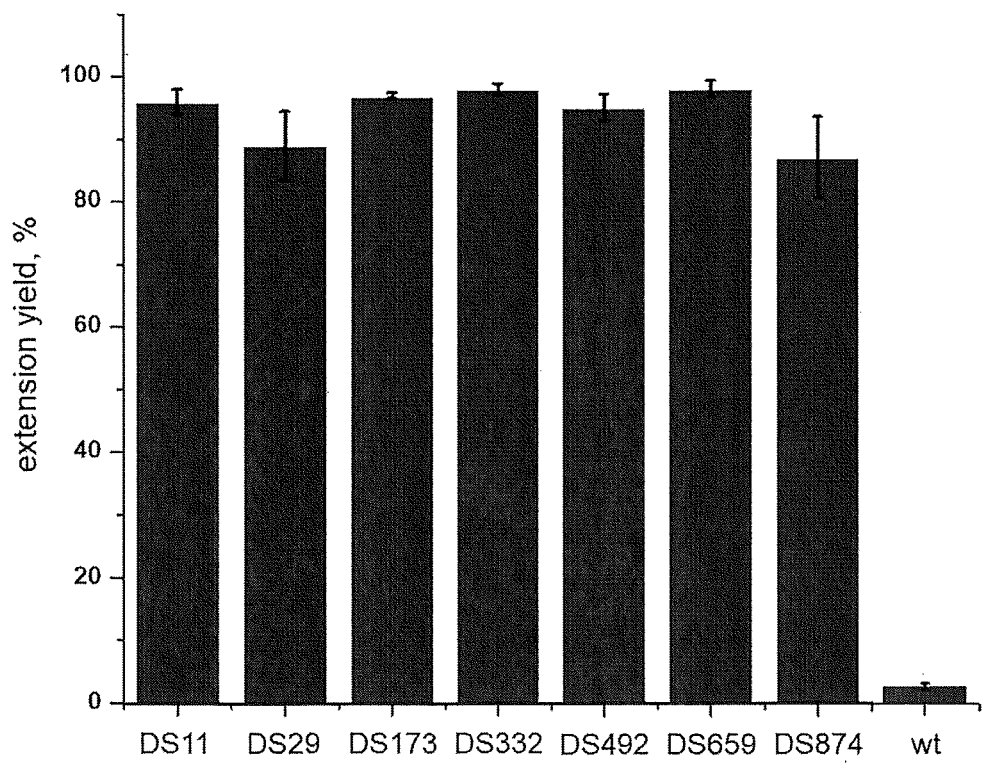
FIG. 2: Comparative results of performances for an elongation assay using wt TdT and TdT variants of the invention. The assay involves fluorescent labeled primers and 3'-O-amino reversible terminator modified nucleotides. The results represent mean value of n=3 experiments for each enzyme.

Results are showed on FIG. 2. For each variant, on the x-axis, the extension percentage has been evaluated as the quantity of expected elongated product over the total quantity of DNA loaded on the gel. Each experiment has been performed in triplicates. The bar height, y-axis, corresponds to the mean value of those three experiments. All the variants according to the invention show more than a 10-fold increase of activity compared to the wt enzyme, confirming the possibility of developing a nucleic acid synthesis technology with these variants.

Example 3—Evaluation of the Activity of Variants of TdT with Unlabeled Primer

Activity Test

Elongation performance of variants of SEQ ID NO: 2: DS928 (R207L+R325P+E328L) and DS950 (R207N+R325A+E328N) generated, expressed and purified according to example 1 was evaluated through the following assay. All the results are compared with a reference variant (SEQ ID No 9) obtained from previous research and to a control tube lacking any polymerase enzyme.

TABLE 8

Activity test

| Reagent | Concentration | Volume |
| --- | --- | --- |
| H$_2$O | — | 12 μL |
| Activity Buffer | 10× | 2 μL |
| dNTP | 250 μM | 2 μL |
| Purified enzyme | 20 μM | 2 μL |
| Fluorescent primer DNA | 500 nM | 2 μL |

Primer used is the following:

(SEQ ID NO: 8)
5'-TTTTTTTTTTTTAAATAAGG-3'

Nucleotides used (noted as dNTP in table 8) were 3'-O-amino-2',3'-dideoxynucleotides-5'-triphosphate (ONH2, Firebird Biosciences) such as 3'-O-amino-2',3'-dideoxyadenosine-5'-triphosphate for example.

For each variant tested one tube was used for the reaction. The reagents were added in the tube starting from the water and then in the order of Table 8. After 30 min at 37° C. the reaction was stopped by addition of formamide (Sigma).

Analysis

The analysis used liquid chromatography and mass spectrometer detection and quantification (LC/MS). Samples from activity test were analyzed through LC/MS. Samples were loaded into the LC/MS instrument and a standard oligonucleotide separation method was performed. Acquisition of data was followed by deconvolution and spectrum calculation.

Figure 3:
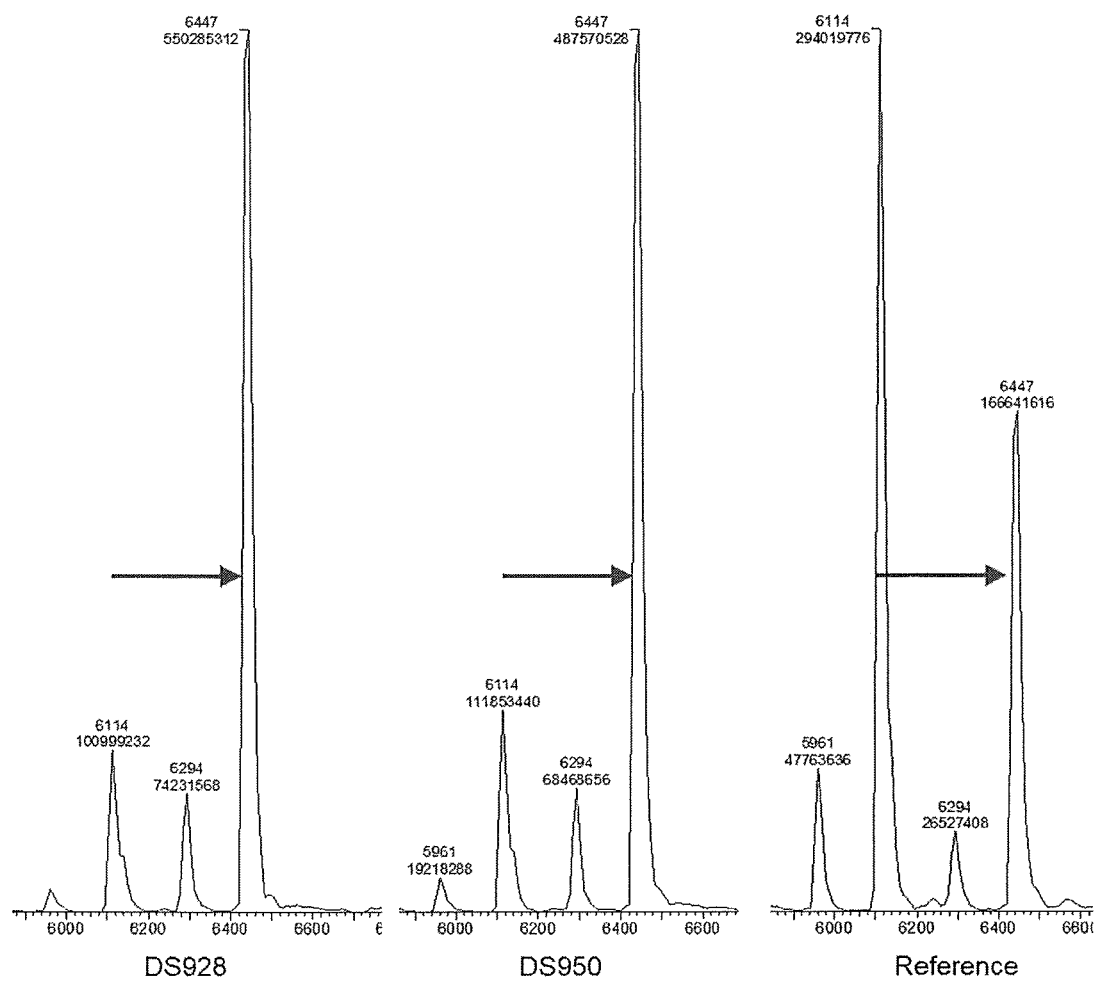
FIG. 3: Mass spectrum analysis of the results obtained for the elongation assay with different TdT variants of the invention. Only the relevant part of the mass spectrum is shown. The arrow shows the peak (mass) for the expected elongated primer.

Results are showed on FIG. 3. The spectrums correspond to the extension analysis of variants DS928, DS950 and references respectively. Initial primer mass is around 6114 and the expected extended product mass is around 6447 (emphasized by the arrows). The intensity of the signal (i.e., the height of the peaks) may be directly correlated to the quantity of material. Both variants DS928, DS950 show significant improvement in the elongation of the starting primer as compared to the reference variant. These results confirm that the new variants according to the invention bring indisputable improvement over the TdT of the prior art.

The invention claimed is:

1. A method of synthesizing a polynucleotide having a predetermined sequence, the method comprising the steps of:
   a) providing an initiator having a 3'-terminal nucleotide having a free 3'-hydroxyl;
   b) repeating cycles of:
      (i) contacting under elongation conditions the initiator or elongated fragments having free 3'-O-hydroxyls with a 3'-O-blocked nucleoside triphosphate and a terminal deoxynucleotidyl transferase (TdT) variant such that the initiator or elongated fragments are elongated by incorporation of a 3'-O-blocked nucleoside triphosphate to form 3'-O-blocked elongated fragments
      wherein the TdT variant comprises an amino acid sequence at least 90% identical to SEQ ID NO:2, SEQ ID NO:11, SEQ ID NO:13, SEQ ID NO:17, SEQ ID NO:19, SEQ ID NO:21, SEQ ID NO:29, or SEQ ID NO:31 with an amino acid substitution of cysteine at position 173, wherein the TdT variant (i) is capable of synthesizing a nucleic acid fragment without a template and (ii) is capable of incorporating a modified nucleotide into the nucleic acid fragment, and
      (ii) deblocking the elongated fragments to form elongated fragments having free 3'-hydroxyls, until the polynucleotide is synthesized.

2. The method of claim 1, wherein said 3'-O-blocked nucleoside triphosphate is a 3'-O—NH$_2$-nucleoside triphosphate, a 3'-O-azidomethyl-nucleoside triphosphate, a 3'-O-allyl-nucleoside triphosphate, or a 3'-O-(2-nitrobenzyl)-nucleoside triphosphate.

3. The method of claim 1, wherein the modified nucleotide is incorporated onto a free 3'-hydroxyl of a nucleic acid fragment.

4. The method of claim 1, wherein the TdT variant incorporates the modified nucleotide at a rate greater than that of a wild type TdT.

5. The method of claim 1, wherein the TdT variant further comprises a substitution of methionine at position 63 with respect to SEQ ID NO:2, SEQ ID NO:11, SEQ ID NO:13, SEQ ID NO:17, SEQ ID NO:19, or SEQ ID NO:29.

6. The method of claim 1, wherein the TdT variant further comprises a substitution of arginine at position 207 with respect to SEQ ID NO:2, SEQ ID NO:11, SEQ ID NO:13, SEQ ID NO:17, SEQ ID NO:19, SEQ ID NO:29 of SEQ ID NO:31.

7. The method of claim 6, wherein the substitution of the arginine is N, L, K, H, G, D, A or P.

8. The method of claim 1, wherein the TdT variant further comprises a substitution of arginine at position 208 with respect to SEQ ID NO:21.

9. The method of claim 1, wherein the TdT variant further comprises a substitution of arginine at position 324 with respect to SEQ ID NO:11 or SEQ ID NO:13.

10. The method of claim 1, wherein the TdT variant further comprises a substitution of arginine at position 331 with respect to SEQ ID NO:17.

11. The method of claim 1, wherein the TdT variant further comprises a substitution of arginine at position 325 with respect to SEQ ID NO:2, SEQ ID NO:19 or SEQ ID NO:31.

12. The method of claim 1, wherein the TdT variant further comprises a substitution of arginine at position 328 with respect to SEQ ID NO: 29.

13. The method of claim 1, wherein the TdT variant further comprises a substitution of glutamic acid at position 327 with respect to SEQ ID NO:11 or SEQ ID NO:13.

14. The method of claim 13, wherein the substitution of the glutamic acid is N, L, T or S.

15. The method of claim 1, wherein the TdT variant further comprises a substitution of glutamic acid at position 334 with respect to SEQ ID NO: 17 or SEQ ID NO:21.

16. The method of claim 1, wherein the TdT variant further comprises a substitution of glutamic acid at position 331 with respect to SEQ ID NO:29.

17. The method of claim 1, wherein the TdT variant further comprises a substitution of glutamic acid at position 328 with respect to SEQ ID NO:2, SEQ ID NO:19, or SEQ ID NO:31.

18. The method of claim 1, wherein the TdT variant further comprises of the cysteine is G, R, P, A, V, S, N, Q or D.

19. The method of claim 1, wherein the substitution of said methionine is R, Q, G, A, V, D, N, H or E.

20. The method of claim 1, wherein the amino acid sequence is at least 95% identical to SEQ ID NO:2, SEQ ID NO:11, SEQ ID NO:13, SEQ ID NO:17, SEQ ID NO:19, SEQ ID NO:21, SEQ ID NO:29, or SEQ ID NO:31.

21. The method of claim 1, wherein the amino acid sequence is at least 97% identical to SEQ ID NO:2, SEQ ID NO:11, SEQ ID NO:13, SEQ ID NO:17, SEQ ID NO:19, SEQ ID NO:21, SEQ ID NO:29, or SEQ ID NO:31.

22. A kit for performing a nucleotide incorporation reaction comprising
   a terminal deoxynucleotidyl transferase (TdT) variant comprising an amino acid sequence at least 90% identical to SEQ ID NO:2, SEQ ID NO:11, SEQ ID NO:13, SEQ ID NO:17, SEQ ID NO:19, SEQ ID NO:21, SEQ ID NO:29, or SEQ ID NO:31 with an amino acid substitution of cysteine at position 173, wherein the TdT variant (i) is capable of synthesizing a nucleic acid fragment without a template and (ii) is capable of incorporating a modified nucleotide into the nucleic acid fragment,
   one or more nucleotides, and
   a nucleic acid primer.

* * * * *

UNITED STATES PATENT AND TRADEMARK OFFICE
CERTIFICATE OF CORRECTION

| | | |
|---|---|---|
| PATENT NO. | : 11,208,637 B2 | Page 1 of 1 |
| APPLICATION NO. | : 16/925785 | |
| DATED | : December 28, 2021 | |
| INVENTOR(S) | : Elise Champion et al. | |

It is certified that error appears in the above-identified patent and that said Letters Patent is hereby corrected as shown below:

In the Specification

In Column 4, Line 41, please change "R336IJN" to ---R336L/N---.

In Column 4, Line 41 and 42, please change "E457N/IJT/S" to ---E457N/L/T/S---.

In Column 54, Line 19, please change "G284US" to ---G284L/S---.

In Column 69, Line 50, please change "intiator" to ---initiator---.

Signed and Sealed this
Eighth Day of February, 2022

Drew Hirshfeld
*Performing the Functions and Duties of the
Under Secretary of Commerce for Intellectual Property and
Director of the United States Patent and Trademark Office*